US011179462B2

(12) United States Patent
Alcolea Alcolea et al.

(10) Patent No.: US 11,179,462 B2
(45) Date of Patent: *Nov. 23, 2021

(54) MOLECULAR ADJUVANT AND VACCINE

(71) Applicants: CONSEJO SUPERIOR DE INVESTIGACIONES CIENTÍFICAS, Madrid (ES); CZ VETERINARIA, S.A., Porriño (ES)

(72) Inventors: Pedro José Alcolea Alcolea, Madrid (ES); Ana María Alonso Ayala, Madrid (ES); Vicente Emilio Larraga Rodríguez De Vera, Madrid (ES)

(73) Assignees: CONSEJO SUPERIOR DE INVESTIGACIONES CIENTÍFICAS, Madrid (ES); CZ VETERINARIA S.A., Porriño (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/745,268

(22) Filed: Jan. 16, 2020

(65) Prior Publication Data

US 2020/0360512 A1    Nov. 19, 2020

Related U.S. Application Data

(63) Continuation of application No. 15/575,910, filed as application No. PCT/EP2016/061621 on May 23, 2016, now Pat. No. 10,568,960.

(30) Foreign Application Priority Data

May 22, 2015   (EP) .................................... 15382273

(51) Int. Cl.
| A61K 39/39 | (2006.01) |
| A61P 33/02 | (2006.01) |
| A61K 39/008 | (2006.01) |
| A61K 39/00 | (2006.01) |

(52) U.S. Cl.
CPC ............ *A61K 39/39* (2013.01); *A61K 39/008* (2013.01); *A61P 33/02* (2018.01); *A61K 2039/53* (2013.01); *A61K 2039/552* (2013.01); *A61K 2039/55561* (2013.01)

(58) Field of Classification Search
None
See application file for complete search history.

(56) References Cited

U.S. PATENT DOCUMENTS

| 8,883,464 B2 | 11/2014 | Lynch et al. |
| 2005/0112713 A1 | 5/2005 | DeWolf, Jr. et al. |

FOREIGN PATENT DOCUMENTS

| WO | 99/37800 A1 | 7/1999 | |
| WO | WO-02077183 A2 * | 10/2002 | ........... C07K 14/212 |

OTHER PUBLICATIONS

El-Attar et al. 2012 (A pestivirus DNA vaccine based on a non-antibiotic resistance *Escherichia coli* essential gene marker; Vaccine 30: 1702-1709) (Year: 2012).*
Alvar et al., "Canine Leishmaniasis," *Advances in Parasitology* 57, 2004. (88 pages).
El-Attar et al., "A pestivirus DNA vaccine based on a non-antibiotic resistance *Escherichia coli* essential gene marker," *Vaccine* 30:1702-1709, 2012.
Gomes et al., "Intranasal delivery of naked DNA encoding the LACK antigen leads to protective immunity against visceral leishmaniasis in mice," *Vaccine* 25:2168-2172, 2007.
Pinto et al., "Intranasal Vaccination against Cutaneous Leishmaniasis with a Particulated Leishmanial Antigen or DNA Encoding LACK," *Infection and Immunity* 72(8):4521-4527, 2004.
Ramiro et al., "Protection in dogs against visceral leishmaniasis caused by Leishmania infantum is achieved by immunization with a heterologous prime-boost regime using DNA and vaccinia recombinant vectors expressing LACK," *Vaccine* 27:2474-2484, 2003.
Ribeiro-de-Jesus et al., "Cytokine profile and pathology in human leishmaniasis," *Braz. J. Med. Biol. Res.* 31(1):143-148, 1998, (9 pages).
Evans et al., "Development of Vaccines against Visceral Leishmaniasis," *Journal of Tropical Medicine* 2012 (892817): 1-14, 2011.
Ribeiro-de-Jesus et al., "Cytokine profile and pathology in human leishmaniasis," *Brazilian Journal of Medical and Biologcal Research* 31: 143-148, 1998.

* cited by examiner

*Primary Examiner* — Mary Maille Lyons
(74) *Attorney, Agent, or Firm* — Seed Intellectual Property Law Group LLP

(57) ABSTRACT

The invention relates to the fields of vaccines and vaccine adjuvants, and generally relates to polynucleotide adjuvants, polynucleotide vaccines and vaccine compositions. More specifically, the invention relates to said polynucleotides and vaccine compositions for use in inducing or enhancing a prophylactic or therapeutic immune response in a mammalian subject. Furthermore, it relates to said polynucleotides and vaccine compositions for use in the prophylactic or therapeutic treatment of an infectious disease, such as in the prophylactic or therapeutic treatment of leishmaniasis.

15 Claims, 25 Drawing Sheets

Specification includes a Sequence Listing.

A)

B)

Select lower limits: %GC=59, ObsCpG/ExpCpG=0.65, Length=200, Distance=100
CpG island 1 start=708, end=917, %GC=59.5, ObsCpG/ExpCpG=1.129, Length=210

MOLECULAR ADJUVANT AND VACCINE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 210238_401C1_SEQUENCE_LISTING.txt. The text file is 34.1 KB, was created on Apr. 30, 2020, and is being submitted electronically via EFS-Web.

FIELD OF INVENTION

The invention relates to the fields of vaccines and vaccine adjuvants, and generally relates to polynucleotide adjuvants, polynucleotide vaccines and vaccine compositions. More specifically, the invention relates to said polynucleotides and vaccine compositions for use in inducing or enhancing a prophylactic or therapeutic immune response in a mammalian subject. Furthermore, it relates to said polynucleotides and vaccine compositions for use in the prophylactic or therapeutic treatment of an infectious disease, such as in the prophylactic or therapeutic treatment of leishmaniasis.

BACKGROUND OF THE INVENTION

Leishmaniasis is a group of diseases caused by parasite protozoa of the genus *Leishmania* belonging to the family of the Trypanosomatids (Killick-Kendrick, R., Med Vet Entomol 1990, 4(1): 1-24). It is transmitted by the bite of bloodsucking sand flies, grouped into the subfamily Phlebotominae, of which 30 species capable of transmitting the disease are known. There are basically three clinical presentations depending on the species involved and the host immune response, cutaneous, mucocutaneous and visceral. The latter is produced by *L. infantum* and is fatal without treatment. It is an endemic disease that affects 15 million people, with 2 million new cases a year in 88 countries in tropical and temperate areas (90% of them in developing countries), Desjeux, P., Clin Dermatol 1996, 14(5): 417-423.

Due to its increased prevalence in recent years it has been declared as an emerging disease by the World Health Organization and it has been described as an opportunistic parasite in immunosuppressed people, mainly in AIDS patients (Pasquau, F., et al. Eur J Clin Microbiol Infect Dis 2005, 24(6): 411-418). It is a disease that is endemic in the Mediterranean basin and in Spain visceral leishmaniasis is considered a public health problem, the dog being the reservoir of the disease; there are about 7 million animals registered in the country, and the infestation rates in this host vary between 10 and 25 percent, with higher incidence areas of up to 34% (Amela, C., et al., Eur J Epidemiol 1995, 11(2): 157-161).

Due to the limited effectiveness of treatments currently used against the disease, the toxicity of the drugs and the emergence of resistance, as well as the occurrence of recurrence, the development of an effective vaccine against leishmaniasis is necessary. In particular, the development of an effective vaccine against canine leishmaniasis will not only control the progression of the disease, but the decrease in the parasite load will interrupt the cycle of transmission between vector and humans.

From a commercial point of view, there are currently only three vaccines on the market against canine leishmaniasis: two of them sold exclusively in Brazil: Leishmune® (Fort Dodge/Pfizer), inactivated and sub-unit vaccine (purified glycoprotein fraction, mannose-fucose ligand) from *Leishmania donovani* (Nogueira, F. S., et al., Vaccine 2005, 23(40): 4805-10) and LeishTec® (Hertape Calier Saúde Animal S.A) protein sub-units vaccine (recombinant protein A2-HIS) against visceral leishmaniasis. In Europe, the European Medicines Agency (EMEA) has recently approved the vaccine Cani Leish® (Laboratoires Bio Veto Test, Groupe Virbac), protein sub-unit inactivated vaccine (purified antigen obtained from *L. infantum* promastigotes) against visceral leishmaniasis, the marketing of which was initiated in 2012 (Moreno, J., et al., PLoS Negl Trop Dis 2012, 6(6): e1683). Efficacy results with these vaccines are however limited. See for instance the report prepared by the EMEA on the scientific discussion for the approval of CaniLeish® wherein it is pointed out that it has shown very limited protection of vaccinated dogs (i.e., protection is lower than 20% according to the decrease in parasite load that it induces in vaccinated animals). None of these vaccines is a DNA vaccine.

The use of the DNA vaccine pCI-neo-LACK in dogs against visceral leishmaniasis has been disclosed by Ramiro et al. (Vaccine 2003, 21(19-20): 2474-84); and Ramos, I., et al. (Vaccine 2008, 26(3): 333-44). Said vaccine was produced by cloning the sequence encoding the activated protein kinase C (LACK) antigen of *Leishmania infantum*. Pinto E. F. et al. (Infection and immunity 2004, 72(8), 4521-4527) disclose the intranasal vaccination of mice with pCI-neo-LACK, which reports that LACK DNA but not empty DNA promoted protective immunity. More recently, antibiotic resistance free plasmid DNA expressing LACK protein (the pORT-LACK plasmid constructed from pCI-neo-LACK by removing ampicillin and neomycin resistance genes and introducing a lac operator sequence as selectable marker) and its use against *Leishmania infantum* infection in an heterologous prime-boost pORT-LACK/MVA-LACK vaccination was also described (Ramos, I., et al., Vaccine 2009, 27(48): 6695-6703).

Vaccination with DNA-LACK vaccines has previously shown to be effective against *L. major* in the murine model (Gurunathan, S., et al., The Journal of experimental medicine, 1997, 186(7): 1137-47; Gurunathan, S. et al., Nat Med 1998, 4(12): 1409-15 and Stobie, L. et. al., Proc Natl Acad Sci 2000, 97(15): 8427-32).

There are a number of advantages of DNA vaccination relative to traditional vaccination techniques. First, it is predicted that because the proteins which are encoded by the DNA sequence are synthesised in the host, the structure or conformation of the protein will be similar to the native protein associated with the disease state. It is also likely that DNA vaccination will offer protection against different strains of a virus, by generating cytotoxic T lymphocyte response that recognise epitopes from conserved proteins. Furthermore, because the plasmids are taken up by the host cells where antigenic protein can be produced, a long-lasting immune response will be elicited. The technology also offers the possibility of combining diverse immunogens into a single preparation to facilitate simultaneous immunisation in relation to a number of disease states (see also Box 1 Saade et al., Expert Rev Vaccines 2012, 11(2):189-209).

There is a need however to improve immunogenicity of DNA vaccines, especially in humans, when compared with traditional protein-based vaccines. Many strategies have been attempted to improve DNA vaccine potency including use of more efficient promoters and codon optimization, addition of traditional or genetic adjuvants, electroporation, intradermal delivery and various prime-boost strategies, see Saade et al., Expert Rev Vaccines 2012, 11(2):189-209.

One approach is the use of traditional adjuvants which act as immune stimulators, as antigen delivery systems, or both. Traditional adjuvant approaches using for instance alum or lipopolysaccharide (LPS) have been mostly superseded in DNA vaccines by use of plasmid-encoded molecular adjuvants.

Despite many strategies having been attempted to improve DNA vaccine potency, there is an on-going need for research into strategies to further enhance DNA vaccines immunogenicity.

FabI gene encodes enoyl-acyl carrier protein (ACP) reductase, an enzyme which is essential for bacterial fatty acid synthesis and sensitive to triclosan which has been reported as a selection marker for molecular cloning (see for instance, Goh et al. 2008, BMC Biotechnology, 8:61). El-attar Laila M R et al. (Vaccine 2011, 30(9) 1702-1709) discloses the use of FabI from *E. coli* as a non-antibiotic selection marker in a DNA vaccine against a pestivirus.

SUMMARY OF THE INVENTION

The authors of the invention have now discovered that FabI gene (SEQ ID NO: 3), or an antigenic fragment thereof (e.g. SEQ ID NO: 1), boosts immunogenicity of DNA vaccines when co-administered as a molecular adjuvant with an antigen of interest. More specifically, it has been shown by the inventors that co-administration of SEQ ID NO: 3 (which comprises SEQ ID NO: 1) with LACK gene (SEQ ID NO: 5), in particular in a DNA plasmid such as pPAL-LACK (SEQ ID NO: 23), obtains similar levels of immunogenicity in a homologous prime-boost administration regime when compared with the heterologous prime-boost regime consisting of pCIneo-LACK and MVA-LACK. An heterologous immunization regime is a well-known strategy to increase immunogenicity and would have been expected to provide higher immunogenicity than the homologous immunization (see, Ramiro, M. J., et al., Vaccine 2003, 21(19-20): 2474-84 and McConkey et al., Nat Med. 2003, 9(6):729-35).

Furthermore, the homologous vaccination eliminates the need to use a virus and therefore simplifies storage, transportation and vaccine handling conditions, with the consequent reduction of costs for health care systems, as storage and handling errors can cost thousands of dollars in wasted vaccine and revaccination.

Moreover, when comparing the efficacy of the pPAL-LACK vaccine with the commercial vaccine CaniLeish® (groups E and F of Example 5, respectively) it has been shown that the parasite burden is lower in dogs vaccinated with pPAL-LACK not only with respect to the infected, non-vaccinated control group (A) but also with respect to CaniLeish®, supporting an increased protection against *Leishmania.*

Thus, in accordance with the particular findings of the present invention, there is provided:

A first aspect of the invention relates to a polynucleotide sequence comprising:

a. a nucleic acid sequence consisting of SEQ ID NO: 1 or a sequence with at least 85% identity to the nucleic acid sequence of SEQ ID NO: 1; or
b. a nucleic acid sequence encoding an amino acid sequence consisting of SEQ ID NO: 2 or an amino acid sequence with at least 90% identity to SEQ ID NO: 2, for use as a vaccine adjuvant.

A second aspect of the invention relates to a polynucleotide sequence comprising:

a. a nucleic acid sequence consisting of SEQ ID NO: 1 or a sequence with at least 85% identity to the nucleic acid sequence of SEQ ID NO: 1; or
b. a nucleic acid sequence encoding an amino acid sequence consisting of SEQ ID NO: 2 or an amino acid sequence with at least 90% identity to SEQ ID NO: 2; and
c. a nucleic acid sequence encoding one or more antigens;

for use as a medicament.

A third aspect of the invention relates to a polynucleotide sequence comprising:

a. a nucleic acid sequence consisting of SEQ ID NO: 1 or a sequence with at least 85% identity to the nucleic acid sequence of SEQ ID NO: 1; or
b. a nucleic acid sequence encoding an amino acid sequence consisting of SEQ ID NO: 2 or an amino acid sequence with at least 90% identity to SEQ ID NO: 2; and
c. a nucleic acid sequence encoding one or more antigens of one or more infectious agents;

for use in the prophylactic or therapeutic treatment of an infectious disease.

A fourth aspect of the invention relates to a polynucleotide sequence comprising:

a. a nucleic acid sequence consisting of SEQ ID NO: 1 or a sequence with at least 85% identity to the nucleic acid sequence of SEQ ID NO: 1; or
b. a nucleic acid sequence encoding an amino acid sequence consisting of SEQ ID NO: 2 or an amino acid sequence with at least 90% identity to SEQ ID NO: 2;

and c. a nucleic acid sequence consisting of SEQ ID NO: 5 or a sequence with at least 85% identity to the nucleic acid sequence of SEQ ID NO:5; or
d. a nucleic acid sequence encoding an amino acid sequence consisting of SEQ ID NO: 6 or an amino acid sequence with at least 90% identity to SEQ ID NO: 6.

A fifth aspect of the invention relates to a polynucleotide sequence comprising:

a. a nucleic acid sequence consisting of SEQ ID NO: 1 or a sequence with at least 85% identity to the nucleic acid sequence of SEQ ID NO: 1; or
b. a nucleic acid sequence encoding an amino acid sequence consisting of SEQ ID NO: 2 or an amino acid sequence with at least 90% identity to SEQ ID NO: 2;

and c. a nucleic acid sequence consisting of SEQ ID NO: 5 or a sequence with at least 85% identity to the nucleic acid sequence of SEQ ID NO:5; or
d. a nucleic acid sequence encoding an amino acid sequence consisting of SEQ ID NO: 6 or an amino acid sequence with at least 90% identity to SEQ ID NO: 6, for use as a medicament.

A sixth aspect of the invention relates to a polynucleotide sequence comprising:

a. a nucleic acid sequence consisting of SEQ ID NO: 1 or a sequence with at least 85% identity to the nucleic acid sequence of SEQ ID NO: 1; or
b. a nucleic acid sequence encoding an amino acid sequence consisting of SEQ ID NO: 2 or an amino acid sequence with at least 90% identity to SEQ ID NO: 2;

and c. a nucleic acid sequence consisting of SEQ ID NO: 5 or a sequence with at least 85% identity to the nucleic acid sequence of SEQ ID NO:5; or d. a nucleic acid sequence encoding an amino acid sequence consisting of SEQ ID NO: 6 or an amino acid sequence with at least 90% identity to SEQ ID NO: 6, for use in the prophylactic or therapeutic treatment of an infectious disease.

A seventh aspect of the invention relates to a pharmaceutical composition comprising a polynucleotide sequence as defined in the first aspect of the invention, further comprising a polynucleotide sequence encoding one or more antigens, and a pharmaceutically acceptable carrier, additive or excipient.

An eight aspect of the invention relates to a pharmaceutical composition comprising a polynucleotide sequence as defined in the second and subsequent aspects of the invention and further comprising a pharmaceutically acceptable carrier, additive or excipient.

An ninth aspect of the invention relates to an antibody or fragment thereof, obtained or obtainable after immunization of a mammal with the polynucleotide as defined in the second and subsequent aspects of the invention, and the pharmaceutical composition according to the seventh or eighth aspects of the invention, wherein said antibody or fragment thereof is suitable for the prophylactic or therapeutic treatment of a mammalian subject.

DETAILED DESCRIPTION OF THE INVENTION

Definitions

Figure 1:
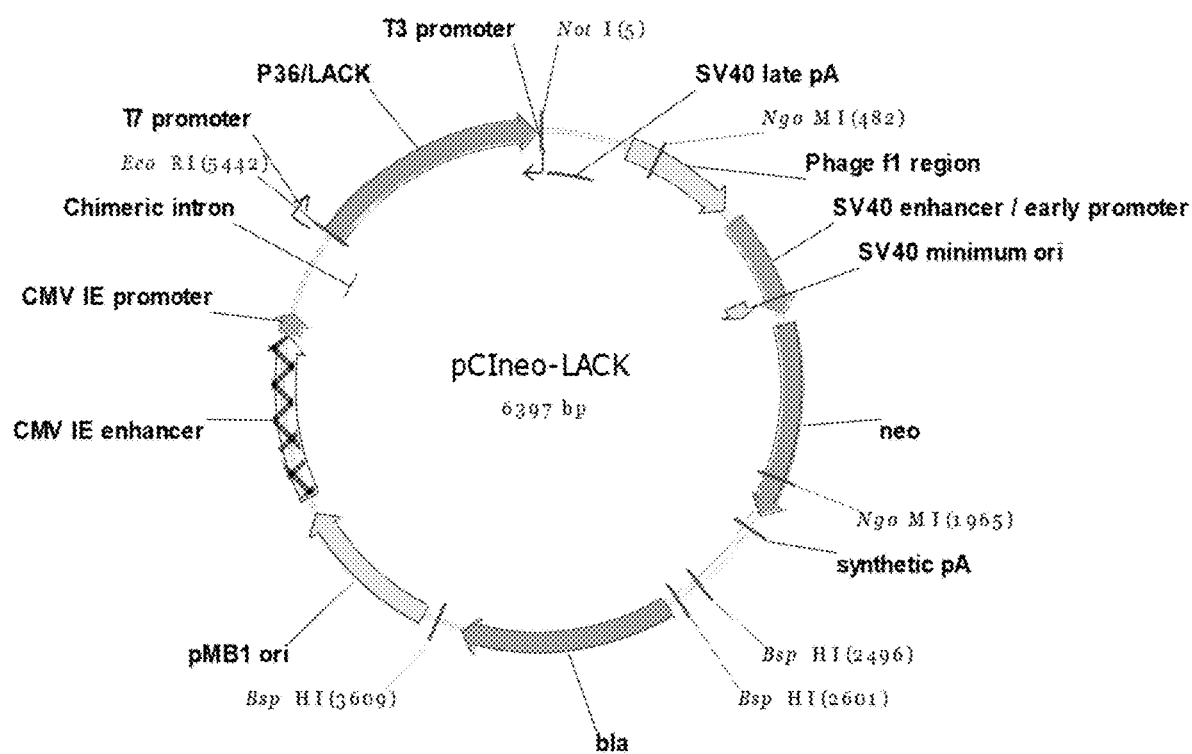
FIG. 1. Schematic representation of the plasmid pCI-neo-LACK.

A "polynucleotide" or "nucleic acid" sequence as used herein refers to a DNA or RNA sequence, preferably to a DNA sequence. The term captures sequences that include any of the known base analogs of DNA and RNA such as, but not limited to 4-acetylcytosine, 8-hydroxy-N6-methyl-adenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

A "coding sequence" or a sequence which "encodes" a gene product as used herein, refers to a nucleic acid sequence which is transcribed (in the case of DNA) and translated (in the case of mRNA), in vitro or in vivo when placed under the control of appropriate regulatory sequences.

The term "identity" as used herein refers to an exact nucleotide-to-nucleotide or amino acid to amino acid correspondence of two polynucleotides or polypeptide sequences, respectively. Two or more sequences (polynucleotide or amino acid) can be compared by determining their "percent identity. The "percent identity" of two sequences, whether nucleic acid or amino acid sequences, is the number of exact matches between two aligned sequences divided by the length of the shorter sequence and multiplied by 100. Suitable programs for calculating the percent identity or similarity between sequences are well known in the art, such as the NCBI BLAST program, used for example with default parameters (http://www.ncbi.nlm.gov/cgi-bin/BLAST).

The terms DNA "control sequences" and "control elements" as used herein, refer collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences/elements need always be present so long as the selected coding sequence is capable of being replicated, transcribed and translated in an appropriate host cell.

"Operably linked" as used herein refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "promoter" as used herein refers to a region of DNA that initiates transcription of a particular coding sequence. Promoters are located near the transcription start sites of genes, on the same strand and upstream on the DNA (towards the 5' region of the sense strand). Promoters can be about 100-1000 base pairs long. An "eukaryotic promoter" includes cis-acting elements such as binding sites for activating protein-1 (AP-1), nuclear factor κB (NF-κB), CArG binding factor A (CBF-A), nuclear factor Y (NF-Y) and others, in addition to the TATA box sequence.

The expression "pharmaceutically acceptable carrier, additive or excipient" is intended to include a formulation, or substance used to stabilize, solubilize and otherwise be mixed with active ingredients to be administered to living animals, including humans. This includes any and all solvents, dispersion media, coatings, antibacterial and antifungal agents, isotonic and absorption delaying agents, and the like, compatible with pharmaceutical administration. Except insofar as any conventional media or agent is incompatible with the active compound, such use in the compositions is contemplated.

The term "vaccine" as used herein refers to a biological preparation that improves immunity to a particular disease. A vaccine typically contains an agent that resembles a disease-causing microorganism, and is often made from weakened or killed forms of the microbe, its toxins or one of its surface proteins.

The term "DNA vaccine" or "DNA-based immunization" as used herein refer to the injection of a DNA vector (typically a bacterial plasmid) which induces an immune response to the antigen encoded by said DNA vector. Once the DNA construct is administered the host cells take up the foreign DNA, expressing the viral gene and producing the corresponding protein inside the cell. This form of antigen presentation and processing induces both MHC and class I and class II restricted cellular and humoral immune responses (Encke, J. et al., 1999, Intervirology, 42:117-124). DNA vaccines usually consist of a bacterial plasmid operably linked to a strong eukaryotic promoter, the gene of interest which encodes for an antigenic peptide and a polyadenylation/transcriptional termination sequences.

The term "adjuvant" or "vaccine adjuvant" as used herein refers to any substance or combination of substances which non-specifically enhances the immune response to an antigen. The term "molecular adjuvant" or "molecular vaccine adjuvant" as used herein refers to a nucleic acid sequence or the expression product thereof which non-specifically enhances the immune response to an antigen expressed from a polynucleotide, such that expression of an antigen from the polynucleotide results in an increased in vivo immune response. Included in this definition are substances which may act as facilitators of in vivo cellular gene delivery, thereby increasing the amount of plasmid DNA delivered to cells that can express the intended antigen. Substances which may enhance delivery of plasmid DNA would include those which do not substantially interact with the plasmid DNA in the formulation and substances which do interact with the plasmid DNA, forming tightly bound or weakly bound complexes between the adjuvant and the plasmid DNA, either in vitro or in vivo.

The term "disease" as used herein is intended to be generally synonymous, and is used interchangeably with, the terms "disorder" and "condition" (as in medical condition), in that all reflect an abnormal condition of the body or of one of its parts that impairs normal functioning and is typically manifested by distinguishing signs and symptoms.

The term "therapeutic treatment" as used herein refers to bringing a body from a pathological state or disease back to its normal, healthy state. For instance, wherein said disease is an infection, after infection or after the clinical manifestation of the disease caused by the infection. It is noted that, this term as used herein is not understood to include the term "prophylactic treatment" as defined herein.

The term "prophylactic treatment" as used herein refers to preventing a pathological state. For instance, wherein said disease is an infection, before the infection. It is noted that this term as used herein is not understood to include the term "therapeutic treatment" as defined above.

The term "mammalian subject" or "mammal" as used herein refers to any of the endothermic vertebrates belonging to class Mammalia.

The term "leishmaniasis" as used herein refers to the major vector-borne disease caused by obligate intramacrophage protozoa of the genus *Leishmania*, and transmitted by the bite of phlebotomine female sand flies of the genera *Phlebotomus* and Lutzomyia, in the old and new worlds, respectively. There are 20 well-recognized *Leishmania* species known to infect humans, which include agents of visceral, cutaneous, and mucocutaneous forms of the disease (see Dawit et al. 2013, J Bacteriol Parasitol, 4:166).

The term "passive immunization" as used herein refers to the administration of antibodies or fragments thereof to a mammalian subject with the intent of conferring immunity to said mammalian subject.

The term "therapeutically effective amount" or "immunologically effective amount" as used herein refers to an amount that is effective, upon single or multiple dose administration to a mammalian subject (such as a human patient) in the prophylactic or therapeutic treatment of a given disease.

The term "infectious agent" as used herein refers to agents that cause an infectious disease. Infectious agents belong to four main groups: viruses, bacteria, fungi, and parasites. Said infectious agents can be extracellular or intracellular.

The term "infectious disease" as used herein refers to diseases caused by infectious agents such as bacteria, viruses, parasites or fungi. Infectious diseases can be spread, directly or indirectly (through a vector and/or reservoir), from one person to another. Zoonotic diseases are infectious diseases of animals that can cause disease when transmitted to humans.

The term "antigen" as used herein refers to an amino acid sequence which elicits an immunological response. An antigen, as used herein, includes a full-length sequence of a protein, analogs thereof, or immunogenic fragments thereof. The term "immunogenic fragment" refers to a fragment of a protein which includes one or more epitopes and thus elicits an immunological response. Such fragments can be identified using any number of epitope mapping techniques, well known in the art. See, e.g. Epitope Mapping Protocols in Methods in Molecular Biology, Vol. 66 (Glenn E. Morris. Ed., Humana Press 1996, Totowa, N.J.). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., Proc. Natl. Acad. Sci. USA 1984, 81:3998-4002; Geysen et al., Molec. Immunol. 1986, 23:709-715. Similarly, conformational epitopes are readily identified by determining spatial conformation of amino acids such as by, e.g. X-ray crystallography and 2-dimensional nuclear magnetic resonance. Synthetic antigens are also included within the definition, for example, polyepitopes, flanking epitopes, and other recombinant or synthetically derived antigens. See, e.g., Bergmann et al., Eur. J. Immunol. 1993, 23:2777-2781; Bergmann et al., J. Immunol. 1996, 157:3242-3249; Suhrbier, A., Immunol, and Cell Biol. 1997, 75:402-408.

Polynucleotide for Use as an Adjuvant

A first aspect of the invention relates to a polynucleotide sequence comprising:
  a. a nucleic acid sequence consisting of SEQ ID NO: 1 or a sequence with at least 85% identity to the nucleic acid sequence of SEQ ID NO: 1; or
  b. a nucleic acid sequence encoding an amino acid sequence consisting of SEQ ID NO: 2 or an amino acid sequence with at least 90% identity to SEQ ID NO: 2,
for use as a vaccine adjuvant, preferably as a molecular adjuvant.

It further relates to said polynucleotide sequence for use as a vaccine adjuvant in the therapeutic or prophylactic treatment of a disease, for use as a vaccine adjuvant in enhancing or inducing a prophylactic or therapeutic immune response in a mammalian subject and to a method of therapeutic or prophylactic treatment wherein such treatment comprises administering to a mammalian subject an immunologically effective amount of said adjuvant polynucleotide.

SEQ ID NO: 1 corresponds to positions 700 to 909 of the fabI gene of *EColi* BL21 (DE3) strain and has the following sequence:

```
700 aaaagcttgccgctccatgct 721 gaatccgggttctgccctgctgacccttcctaccttggcgctgag
    cgcgctatcccgaa 781 ctacaacgttatgggtctggcaaaagcgtctctggaagcgaacgtg
    cgctatatggcgaa 841 cgcgatgggtccggaaggtgtgcgtgttaacgccatctctgctggt
    ccgatccgtactct 901 ggcggcttc.
```

In a particular embodiment, said sequence with at least 85% identity to SEQ ID NO: 1 has at least 90% identity, preferably 95% identity, more preferably 96%, 97%, 98% or 99% identity.

SEQ ID NO: 2 is the polypeptide encoded within SEQ ID NO: 1 and has the following sequence:
KACRSMLNPGSALLTLSYLGAERAIPNYNVMGLAKASLEANVRYMANAMG

PEGVRVNAISAGPIRTLAA.

In a particular embodiment, said sequence with at least 90% identity to SEQ ID NO: 2 has at least 95% identity, more preferably 96%, 97%, 98% or 99% identity. SEQ ID NO: 1 corresponds to a sequence with 59% of G+C in the fabI gene of EColi BL21 (DE3) strain. Such a sequence was predicted to be a CpG island using the CpG Island Searcher software (Takai and Jones, 2002, PNAS 99(6):3740-5), as described in Example 4. Since the amount of antigen expressed in DNA vaccines is often in the order of nanograms to pictograms, immunogenicity is typically dependent upon help from CpG motifs in the polynucleotide (e.g. the plasmid backbone) which play a role of adjuvants promoting the induction of T-cell responses (Dalpke et al. 2001, Immunobiology, 204(5):667-76; Klinman et al. 1997, Immunol., 158(8):3635-9; Krieg, et al. 1995 Nature, 374(6522):546-9).

In a preferred embodiment, said polynucleotide sequence comprises:

a. a nucleic acid sequence consisting of SEQ ID NO:3 or a sequence with at least 85% identity to the nucleic acid sequence of SEQ ID NO: 3; or b. a nucleic acid sequence encoding an amino acid sequence consisting of SEQ ID NO: 4 or an amino acid sequence with at least 90% identity to SEQ ID NO: 4.

SEQ ID NO: 3 corresponds to the fabI gene of EColi BL21 (DE3) strain and has the following sequence:

```
  1 atgggttttc tttccggtaa gcgcattctg gtaaccggtg
    ttgccagcaa actatccatc 61 gcctacggta tcgctcaggc gatgcaccgc gaaggagctg
    aactggcatt cacctaccag 121 aacgacaaac tgaaggccg cgtagaagaa tttgccgctc
    aattgggttc tgacatcgtt 181 ctgcagtgcg atgttgcaga agatgccagc atcgacacca
    tgttcgctga actggggaaa 241 gtttggccga aatttgacgg tttcgtacac tctattggtt
    ttgcacctgg cgatcagctg 301 gatggtgact atgttaacgc cgttacccgt gaaggcttca
    aaattgccca cgacatcagc 361 tcctacagct tcgttgcaat ggcaaaagct tgccgctcca
    tgctgaatcc gggttctgcc 421 ctgctgaccc tttcctacct tggcgctgag cgcgctatcc
    cgaactacaa cgttatgggt 481 ctggcaaaag cgtctctgga agcgaacgtg cgctatatgg
    cgaacgcgat gggtccggaa 541 ggtgtgcgtg ttaacgccat ctctgctggt ccgatccgta
    ctctggcggc ttccggtatc 601 aaagacttcc gcaaaatgct ggctcattgc gaagccgtta
    ccccgattcg ccgtaccgtt 661 actattgaag atgtgggtaa ctctgcggca ttcctgtgct
    ccgatctctc tgccggtatc 721 tccggtgaag tagtccacgt tgacggcggt ttcagcatcg
    ctgcaatgaa cgaactcgaa.
```

In a particular embodiment, said sequence with at least 85% identity to SEQ ID NO: 3 has at least 90% identity, preferably 95% identity, more preferably 96%, 97%, 98% or 99% identity.

FabI gene (SEQ ID NO:3) encodes an enoyl-acyl carrier protein (ACP) reductase which has the following sequence (SEQ ID NO: 4):

```
MGFLSGKRILVTGVASKLSIAYGIAQAMHREGAELAFTYQNDKLKGRVEEF
AAQLGSDIVLQCDVAEDASIDTMFAELGKVWPKFDGFVHSIGFAPGDQLDG
DYVNAVTREGFKIAHDISSYSFVAMAKACRSMLNPGSALLTLSYLGAERAI
PNYNVMGLAKASLEANVRYMANAMGPEGVRVNAISAGPIRTLAASGIKDFR
KMLAHCEAVTPIRRTVTIEDVGNSAAFLCSDLSAGISGEVVHVDGGFSIAA
MNELELK.
```

In a particular embodiment, said sequence with at least 90% identity to SEQ ID NO: 4 has at least 95% identity, more preferably 96%, 97%, 98% or 99% identity, including for instance fabI392(ts) (Bergler, H et al., J. Gen. Microbiol., 1992, 138 2093-100), fabIG93S or fabIS241F variants of the fabI gene expression product.

Enoyl-acyl carrier protein (ACP) reductase is an enzyme which is essential for bacterial fatty acid synthesis and sensitive to triclosan (5-chloro-2-(2,4-dichlorophenoxy) phenol) which was previously known as a selection marker for molecular cloning (see for instance, Goh et al. 2008, BMC Biotechnology, 8:61). The presence of triclosan affects the growth of the bacteria and is lethal beyond a certain concentration in the medium. The selection mechanism in this case is not based on the existence of a gene for resistance to the selection agent, but on increasing the concentration of the enoyl-ACP reductase protein in the cytoplasm in those clones which acquire the foreign DNA. Thus, bacteria acquiring said polynucleotide, recombinant or not, will be able to express the fab I gene at much higher levels than non-transformants, for example, as up to about 50 enoyl-ACP reductase molecules per cell can coexist. When the triclosan:enoyl-ACP reductase binding occurs equivalent to equivalent, there will be a range of concentrations of triclosan in which transformant bacteria survive, and non-transformants will not survive. Therefore, this system acts as a selection marker without being necessary the presence of an antibiotic resistance gene.

In a particular embodiment, said polynucleotide sequence comprises one of said nucleic acid sequences (a) or (b) above operably linked to control sequences. Preferably, said nucleic acid sequences (a) or (b) are operably linked to at least one promoter, preferably to a eukaryotic promoter, i.e., which enables the expression of the inserted coding sequence in eukaryotic cells, for instance, in mammalian cells.

Preferably said promoter is a strong constitutive promoter which will ensure high expression levels of the coding sequence, such as for instance viral promoters, including cytomegalovirus immediate early (CMV-IE) promoter, the simian virus 40 (SV40) promoter, the Rous sarcoma virus long terminal repeat (RSV-LTR), Moloney murine leukaemia virus (MoMLV) LTR, and other retroviral LTR promoters; and non-viral promoters such as muscle-specific muscle creatine kinase (MCK), ubiquitin C (UBC) and elongation factor 1a (EF1a) promoters, PGK1 promoter (see, Papadakis et al., Current Gene Therapy 2004, 4, 89-113). Preferably, said promoter is the promoter of the FabI gene (SEQ ID NO: 7):

```
  1 GTGCTGGAGA ATATTCGGCA AGGTCTGAAC CGTCCCAGCC
    ATCGCCATGA AAGGGTTAGG

61 GGCTGTATGA GCCTGTTTGT TGCTGGGGTA ACAATATTTG
    CACAATACGG TCCCCTCGCC
```

```
121 CCTCTGGGGA GAGGGTTAGG GTGAGGGGAA AAGCGCCCC
    CCTGCCGCAG CCTGCTCCGG

181 TCGGACCTGG CAACTATAGC TACTCACAGC CAGGTTGATT
    ATAATAACCG TTTATCTGTT

241 CGTACTGTTT ACTAAAACGA CGAATCGCCT GATTTTCAGG
    CACAACAAGC ATCAACAATA

301 AGGATTAAAG CT.
```

The underlined sequences are key elements of the promoter: the −35 and the −10 boxes followed by the transcription factor (TF)-binding site.

In a particular embodiment, said polynucleotide is a vector. By "vector" is meant any genetic element, such as a plasmid, phage, transposon, cosmid, chromosome, virus, virion, etc., which is capable of replication when associated with the proper control elements and which can transfer gene sequences between cells.

Said vector might be a viral vector. A number of viral based systems have been used for gene delivery. Many gene therapy clinical trials rely on retroviruses or adenoviruses to deliver the desired gene. Other viruses used as vectors include adeno-associated viruses, lentiviruses, pox viruses, alphaviruses, and herpes viruses. These viruses differ in how well they transfer genes to the cells they recognize and are able to infect, and whether they alter the cell's DNA permanently or temporarily. A comparison of different viral vectors in use for gene therapy together with an overview of their advantages and disadvantages is provided in http://www.genetherapynet.com/viral-vectors.html. Preferably, said vector is a plasmid, wherein said plasmid is a circular or linear bacterial DNA.

In a preferred embodiment, the above described polynucleotide consists of a bacterial plasmid wherein one of said nucleic acid sequences (a) or (b) above is operably linked at least to a eukaryotic promoter (preferably, a strong promoter) and to a polyadenylation/transcriptional termination sequences. The bacterial plasmid can be grown in bacteria, such as for example *E. coli* and then isolated and prepared in an appropriate formulation (according to the intended route of administration) before being administered to the host. Following administration the plasmid is taken up by cells of the host where the encoded peptide(s) are produced.

More preferably, said polynucleotide further comprises one or more, preferably all, of the following elements:
  i) a multiple cloning site (MCS) or polylinker, which is an artificial sequence present in virtually all cloning vectors consisting of a conglomerate of specific targets for different restriction enzymes allowing cloning of most of the DNA fragments of interest, an example of MCS is the one in the pCIneo plasmid (Promega, GenBank: U47120);
  ii) polyadenylation and transcription termination signals. Examples of transcription termination signals include, but are not limited to, polyA, SV40polyA, human growth hormone (HGH)polyA, and bovine growth hormone polyA;
  iii) a sequence for plasmid encapsidation in phages, such as the f1 origin; and
  iv) a bacterial replication origin, such as the replication origin derived from ColE1.

The above polynucleotide may contain one or more antibiotic resistance genes, such as the neomycin phosphotransferase gene (npt or neo$^R$) or the β-lactamase gene (bla or amp$^R$). Preferably, said polynucleotide sequence is characterized by the absence of antibiotic resistance genes.

The polynucleotide sequence as defined above is preferably co-administered with a nucleic acid sequence encoding one or more antigens (also referred as "antigen coding sequence"). The antigen coding sequence could be found either in the same polynucleotide sequence comprising the nucleic acid sequences a) or b) as defined above or in a different polynucleotide. When said antigen coding sequence is part of a different polynucleotide, said antigen encoding polynucleotide and the polynucleotide sequence comprising the nucleic acid sequences a) or b) as defined above can be part of the same or a different composition. In the latter case, administration can be simultaneous or consecutive, preferably the polynucleotide sequence comprising the nucleic acid sequences a) or b) as defined above is administered shortly before or after administration of the composition containing said antigen encoding polynucleotide. In a preferred embodiment, the adjuvant of the invention and the antigen coding sequence form part of the same polynucleotide, it might be desirable that both the antigen coding sequence and the adjuvant coding sequence are under the control of the same promoter.

The Polynucleotide of the Invention for Use as a Medicament

A second aspect of the invention relates to a polynucleotide sequence comprising:
  a. a nucleic acid sequence consisting of SEQ ID NO: 1 or a sequence with at least 85% identity to the nucleic acid sequence of SEQ ID NO: 1; or
  b. a nucleic acid sequence encoding an amino acid sequence consisting of SEQ ID NO: 2 or an amino acid sequence with at least 90% identity to SEQ ID NO: 2; and
  c. a nucleic acid sequence encoding one or more antigens;
  for use as a medicament, preferably for use as a vaccine.

In a particular embodiment, it relates to a polynucleotide sequence comprising:
  a. a nucleic acid sequence consisting of SEQ ID NO: 1 or a sequence with at least 85% identity to the nucleic acid sequence of SEQ ID NO: 1; or
  b. a nucleic acid sequence encoding an amino acid sequence consisting of SEQ ID NO: 2 or an amino acid sequence with at least 90% identity to SEQ ID NO: 2, for use as a vaccine adjuvant, as described under the first aspect of the invention, which further comprises a nucleic acid sequence encoding one or more antigens.

Preferably, said antigens are known to elicit an immune response for the prophylactic or therapeutic treatment of a particular disease. Typically, said one or more antigen coding sequences are operably linked to a promoter as defined above. More preferably, the sequence according to a) or b) above and the nucleic acid sequence encoding one or more antigens are under the control of the same promoter.

It further relates to the polynucleotide sequence as described herein for use in the therapeutic or prophylactic treatment of a disease, for use in enhancing or inducing a prophylactic or therapeutic immune response in a mammalian subject and to a method of therapeutic or prophylactic treatment wherein such treatment comprises administering to a mammalian subject a therapeutically effective amount of said polynucleotide.

In a preferred embodiment, said polynucleotide sequence according to the above comprises:
  a. a nucleic acid sequence consisting of SEQ ID NO:3 or a sequence with at least 85% identity to the nucleic acid sequence of SEQ ID NO: 3; or b. a nucleic acid sequence encoding an amino acid sequence consisting of SEQ ID NO: 4 or an amino acid sequence with at least 90% identity to SEQ ID NO: 4 as described above.

In a particular embodiment, said polynucleotide sequence comprises one of said nucleic acid sequences (a) or (b) above operably linked to control sequences. Preferably, said nucleic acid sequences (a) or (b) are operably linked to at least one promoter as defined above.

Figure 3:
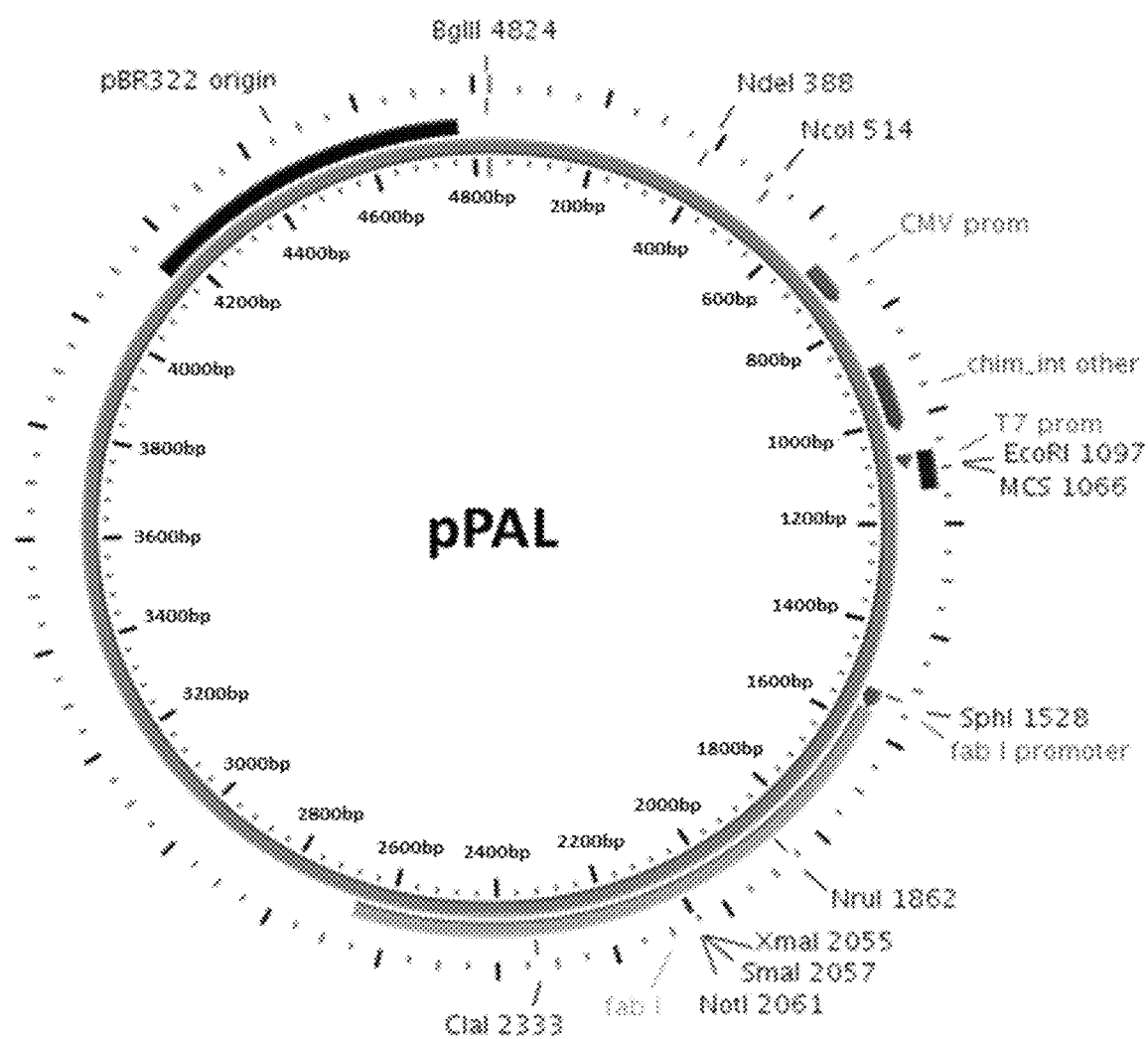
FIG. 3. Schematic representation of the plasmid pPAL (SEQ ID NO: 24).

In a preferred embodiment, said polynucleotide consists of the pPAL vector (SEQ ID NO: 24), which consists of the elements shown in FIG. 3.

Further details and preferred embodiments of said polynucleotide have been provided under the first aspect of the invention.

Second and Further Medical Uses

A third aspect of the invention relates to a polynucleotide sequence comprising:
  a. a nucleic acid sequence consisting of SEQ ID NO: 1 or a sequence with at least 85% identity to the nucleic acid sequence of SEQ ID NO: 1; or
  b. a nucleic acid sequence encoding an amino acid sequence consisting of SEQ ID NO: 2 or an amino acid sequence with at least 90% identity to SEQ ID NO: 2; and
  c. a nucleic acid sequence encoding one or more antigens of one or more infectious agents;
  for use in the prophylactic or therapeutic treatment of an infectious disease.

In a particular embodiment, it relates to a polynucleotide sequence comprising:
  a. a nucleic acid sequence consisting of SEQ ID NO: 1 or a sequence with at least 85% identity to the nucleic acid sequence of SEQ ID NO: 1; or
  b. a nucleic acid sequence encoding an amino acid sequence consisting of SEQ ID NO: 2 or an amino acid sequence with at least 90% identity to SEQ ID NO: 2,
  for use as a vaccine adjuvant, as described under the first aspect of the invention, which further comprises a nucleic acid sequence encoding one or more antigens of one or more infectious agents.

In a particular embodiment, said one or more antigens are antigens of parasites (including protozoa and helminths). Therefore, according to a preferred embodiment said one or more antigens are helminth and/or protozoa antigens. In another particular embodiment, said infectious disease is a disease caused by an intracellular infectious agent (such as viruses or intracellular parasites) and said one or more antigens are antigens from of one or more intracellular infectious agent. Examples of such diseases are those caused by obligatory intracellular parasites which include *Plasmodium* sp, *Trypanosoma cruzi, Toxoplasma gondii* and *Leishmania* sp. More preferably said disease is leishmaniasis and said one or more antigens are leishmaniasis antigens. Examples of commercial antigens with prophylactic use against leishmaniasis are: LiESP/QA-21 (CaniLeish® vaccine); A2 antigen (LeishTec® Vaccine); fucose-manose ligand (Leishmune® vaccine).

In a preferred embodiment, the invention relates to said polynucleotide sequence for use in the therapeutic or prophylactic treatment of leishmaniasis, preferably for use in the therapeutic or prophylactic treatment of canine leishmaniasis.

A person skilled in the art will know how to assess the protective effect against Leishmaniasis, which is typically shown by a decrease of the parasite burden. The determination of cytokine levels such as IFNgamma, IL-10 or TNFalpha and quantification of the immunoglobulin levels (e.g. total IgG, IgG1 and/or IgG2) may be also used in the evaluation of the effectiveness of the immunisation method. In particular, an enhancement of the pro-inflammatory cytokine IFNgamma is characteristic of a predominant cellular Th1 response which has been associated to resistance to Leishmaniasis, whereas an increase of the humoral response has been described to be a marker of susceptibility to the disease.

The parasite load may be determined from any biological sample which may contain the parasite. Typical biological samples are the blood, lymphoid tissues and organs (e.g. the lymph nodes) or target organs, such as the bone marrow, spleen or liver. Methods for determining the parasite load are well known in the art and this may include the determination of *Leishmania* genomic DNA. Generally, primers are complementary to the kinetoplast minicircle conserved region of parasite DNA, allowing the detection of several *Leishmania* species (see for instance, Mary et al., J Clin Microbiol 2004, 42(11): 5249-5255; Lachaud et al., J Clin Microbiol 2001, 39:613-617). Other methods known in the art are the direct agglutination test (see for instance, Ramiro et al. Vaccine 2003, 21(19-20): 2474-84), the limiting dilution assay (see for instance, Gomes et al., Vaccine 2007, 25(12):2168-2172) and the quantification of GFP-expressing parasites (see for instance, Pinto E. F. et al., Infection and immunity 2004, 72(8), 4521-4527)

Determination of cytokine or immunoglobuline levels may be also carried out by any method known in the art for the quantification of target mRNA or polypeptide expression levels. These methods are well known in the art and illustrative, non-limiting methods are described in the examples.

The cytokine and/or immunoglobulin levels can be determined from any biological sample which may contain thereof. These include biological fluids, such as whole blood, serum, plasma, synovial fluid, cerebrospinal fluid, bronchial lavage, ascites fluid, bone marrow aspirate, pleural effusion, urine, as well as any tissue or any other bodily constituent that could contain antibodies or cytokines. Preferably, said biological sample is blood, serum or plasma, more preferably serum.

Molecular biology methods for measuring quantities of target nucleic acid sequences are well known in the art. These methods include but are not limited to end point PCR, competitive PCR, reverse transcriptase-PCR (RT-PCR), real time or quantitative PCR (qPCR), reverse transcriptase qPCR (RT-qPCR), PCR-pyrosequencing, PCR-ELISA, DNA microarrays, in situ hybridization assays such as dot-blot or Fluorescence In Situ Hybridization assay (FISH), branched DNA (Nolte, Adv. Clin. Chem. 1998, 33:201-235) and to multiplex versions of said methods (see for instance, Andoh et al., Current Pharmaceutical Design, 2009; 15, 2066-2073). Preferably, said nucleic acid determination assay is qPCR or RT-qPCR.

Various types of immunoassays are known to one skilled in the art for the quantitation of proteins of interest. These methods are based on the use of affinity reagents, which may be any antibody or ligand specifically binding to the target protein, which is preferably labeled.

For example, western blotting or immunoblotting techniques allow comparison of relative abundance of proteins separated by an electrophoretic gel (e.g., native proteins by 3-D structure or denatured proteins by the length of the polypeptide). Immunoblotting techniques use antibodies (or other specific ligands in related techniques) to identify target proteins among a number of unrelated protein species. They involve identification of protein target via antigen-antibody (or protein-ligand) specific reactions. Proteins are typically separated by electrophoresis and transferred onto a sheet of polymeric material (generally nitrocellulose, nylon, or polyvinylidene difluoride). Dot and slot blots are simplified procedures in which protein samples are not separated by electrophoresis but immobilized directly onto a membrane.

Traditionally, quantification of proteins in solution has been carried out by immunoassays on a solid support. Said immunoassay may be for example an enzyme-linked immunosorbent assay (ELISA), a fluorescent immunosorbent assay (FIA), a chemiluminescence immunoassay (CIA), or a radioimmunoassay (RIA), an enzyme multiplied immunoassay, a solid phase radioimmunoassay (SPROA), a fluorescence polarization (FP) assay, a fluorescence resonance energy transfer (FRET) assay, a time-resolved fluorescence resonance energy transfer (TR-FRET) assay, a surface plasmon resonance (SPR) assay. Multiplex and any next generation versions of any of the above, such as bead-based flow-cytometry immunoassays (e.g., based on the Luminex xMAP technology) are specifically encompassed. Preferably, said immunoassay is an ELISA assay or any multiplex version thereof.

Other methods that can be used for quantification of proteins are techniques based on mass spectrometry (MS) such as liquid chromatography coupled to mass spectrometry (LC/MS), described for example in US2010/0173786, or tandem LC-MS/MS (WO2012/155019, US2011/0039287, M. Rauh, J Chromatogr B Analyt Technol Biomed Life Sci 2012 Feb. 1, 883-884. 59-67) and the use of arrays of peptides, proteins or antibodies and multiplex versions of the above techniques, as well as the next generation of such techniques and combinations thereof.

The term leishmaniasis encompasses a disease caused from over 25 *Leishmania* species, including among others *L. infantum, L. donovani, L. major, L. aethiopica, L. mexicana, L. amazonensis, L. venezuelensis, L. braziliensis* and *L. peruviana*. There are 3 main forms of the disease:

Visceral leishmaniasis (VL also known as kala-azar) is fatal if left untreated. It is characterized by irregular bouts of fever, weight loss, enlargement of the spleen and liver, and anaemia. *L. donovani* and *L. infantum* are the main causative agents.

Cutaneous leishmaniasis (CL) is the most common form of leishmaniasis and causes skin lesions, mainly ulcers, on exposed parts of the body, leaving life-long scars and serious disability. *L. major* (Old World) and *L. mexicana* and *L. amazonensis* (New World) are the main etiological agents.

Mucocutaneous leishmaniasis leads to partial or total destruction of mucous membranes of the nose, mouth and throat. *L. braziliensis* is the main species responsible for this form of the disease.

More information on the disease, diagnosis and treatment can be found for instance through http://www.cdc.gov/parasites/leishmaniasis/health_professionals/index.html or http://www.who.int/leishmaniasis/resources/en/.

Preferably, leishmaniasis is visceral leishmaniasis. The general term visceral leishmaniasis encompasses a broad spectrum of severity and manifestations. The onset can be chronic, subacute, or acute. Although the incubation period generally ranges from weeks to months, asymptomatic infection can become clinically manifest years to decades after the exposure in people who become immunocompromised for other medical reasons (such as HIV/AIDS). Visceral leishmaniasis usually is caused by the species *L. donovani* and *L. infantum* (*L. chagasi* generally is considered synonymous with *L. infantum*) and affects internal organs (particularly, spleen, liver, and bone marrow).

It further relates to a method of therapeutic or prophylactic treatment against the above diseases wherein such treatment comprises administering to a mammalian subject a therapeutically effective amount of said polynucleotide.

For example, said mammalian subject is selected from a human, companion animal, non-domestic livestock or zoo animal. For example, the subject may be selected from a human, dog, cat, cow, pig, sheep, horse, bear, and so on. In a preferred embodiment, said mammalian subject is an animal which is known to be a host affected by *Leishmania*, such as for instance hyraxes, canids, rodents, equids and humans. In a more preferred embodiment, said mammalian subject is a dog (main reservoir for *L.infantum*) or a human.

Further details and preferred embodiments of said polynucleotide have been provided under the previous aspects of the invention.

Polynucleotide Sequence of the Invention Comprising the Lack Gene and Medical Uses Thereof A fourth aspect of the invention relates to a polynucleotide sequence comprising:
a. a nucleic acid sequence consisting of SEQ ID NO: 1 or a sequence with at least 85% identity to the nucleic acid sequence of SEQ ID NO: 1; or
b. a nucleic acid sequence encoding an amino acid sequence consisting of SEQ ID NO: 2 or an amino acid sequence with at least 90% identity to SEQ ID NO: 2; and
c. a nucleic acid sequence consisting of SEQ ID NO: 5 or a sequence with at least 85% identity to the nucleic acid sequence of SEQ ID NO:5; or
d. a nucleic acid sequence encoding an amino acid sequence consisting of SEQ ID NO: 6 or an amino acid sequence with at least 90% identity to SEQ ID NO: 6.

SEQ ID NO: 5 corresponds to the *Leishmania infantum* activated protein kinase C receptor homolog (p36Li) mRNA, complete cds (LACK gene) with GenBank accession number: U49695.1. In a particular embodiment, said sequence with at least 85% identity to SEQ ID NO: 5 has at least 90% identity, preferably 95% identity, more preferably 96%, 97%, 98% or 99% identity. SEQ ID NO: 6 (LACK antigen) is the polypeptide encoded within SEQ ID NO:5 and has the following sequence:

```
MNYEGHLKGHRGWVTSLACPQQAGSYIKVVSTSRDGTAISWKANPDRHSVD

SDYGLPSHRLEGHTGFVSCVSLAHATDYALTASWDRSIRMWDLRNGQCQRK

FLKHTKDVLAVAFSPDDRLIVSAGRDNVIRVWNVAGECMHEFLRDGHEDWV

SSICFSPSLEHPIVVSGSWDNTIKVWNVNGGKCERTLKGHSNYVSTVTVSP

DGSLCASGGKDGAALLWDLSTGEQLFKINVESPINQIAFSPNRFWMCVATE

RSLSVYDLESKAVIAELTPDGAKPSECISIAWSADGNTLYSGHKDNLIRVW

SISDAE.
```

In a particular embodiment, said sequence with at least 90% identity to SEQ ID NO: 6 has at least 95% identity, more preferably 96%, 97%, 98% or 99% identity.

LACK antigen is an analog in *Leishmania* of the receptor for activated protein kinase C in mammals (RACK) according to its amino acid sequence.

In a preferred embodiment, said polynucleotide sequence according to the above comprises:

a. a nucleic acid sequence consisting of SEQ ID NO:3 or a sequence with at least 85% identity to the nucleic acid sequence of SEQ ID NO: 3; or
b. a nucleic acid sequence encoding an amino acid sequence consisting of SEQ ID NO: 4 or an amino acid sequence with at least 90% identity to SEQ ID NO: 4 as described above.

In a more preferred embodiment, said polynucleotide comprises one or more, preferably all, of the following elements:
i) a nucleic acid sequence as defined above consisting of SEQ ID NO:1 or a sequence with at least 85% identity to the nucleic acid sequence of SEQ ID NO: 1; or SEQ ID NO:3 or a sequence with at least 85% identity to the nucleic acid sequence of SEQ ID NO: 3; or encoding an amino acid sequence consisting of SEQ ID NO: 2 or an amino acid sequence with at least 90% identity to SEQ ID NO: 2; or an amino acid sequence consisting of SEQ ID NO: 4 or an amino acid sequence with at least 90% identity to SEQ ID NO: 4;
i) the cytomegalovirus (CMV) enhancer/promoter;
ii) the pCIneo plasmid (Promega, GenBank: U47120) multiple cloning site (MCS);
iii) a nucleic acid sequence as defined above consisting of SEQ ID NO: 5 or a sequence with at least 85% identity to the nucleic acid sequence of SEQ ID NO:5; or encoding an amino acid sequence consisting of SEQ ID NO: 6 or an amino acid sequence with at least 90% identity to SEQ ID NO: 6;
iv) the SV40 polyadenylation and transcription termination signals;
v) the f1 origin for plasmid encapsidation in phages;
vi) the replication origin derived from ColE1.

Figure 2:
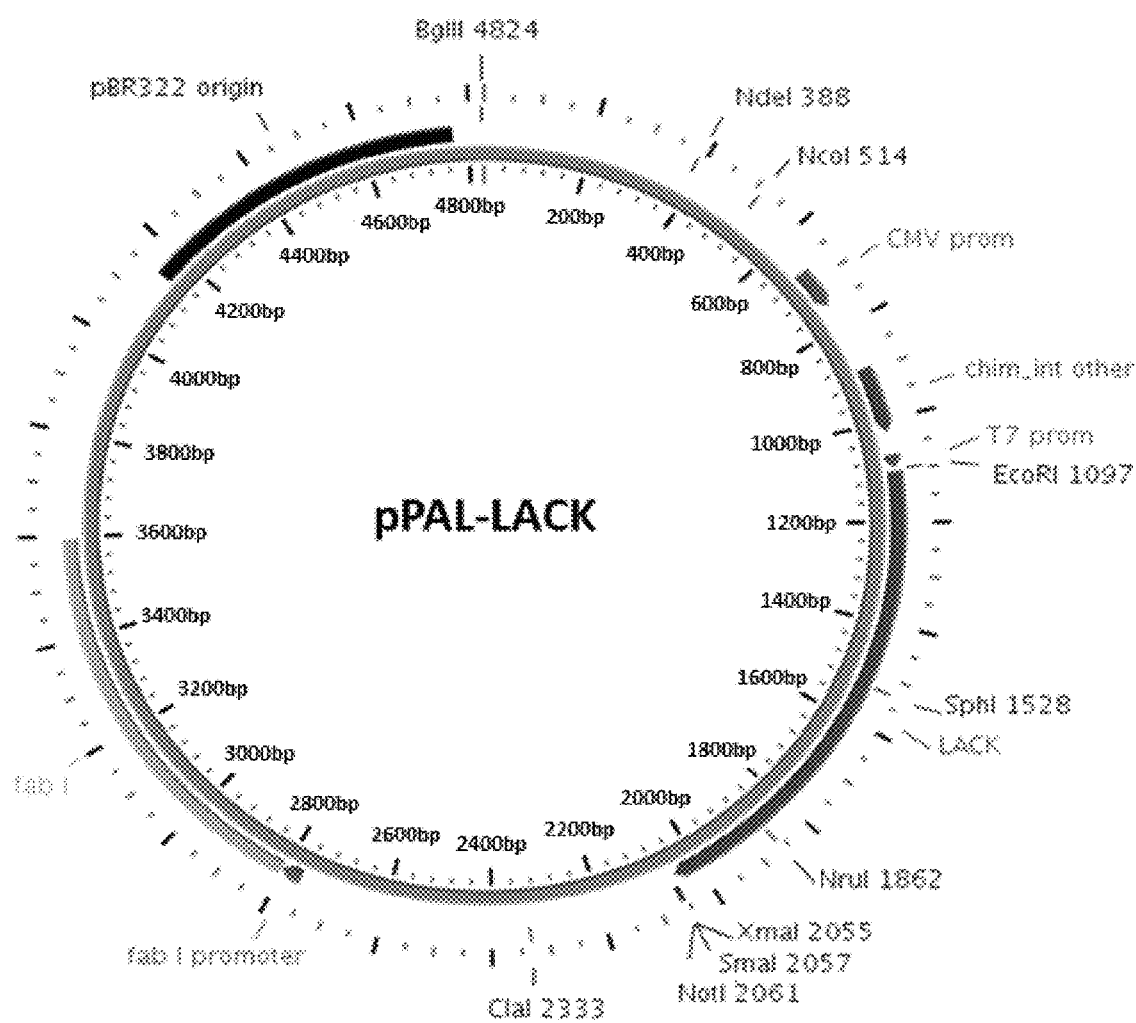
FIG. 2. Schematic representation of the plasmid pPAL-LACK (SEQ ID NO: 23).

In a preferred embodiment, said polynucleotide consists of the pPAL-LACK vector (SEQ ID NO: 23), which consists of the elements shown in FIG. 2.

For instance, the pPAL-LACK vector is generated from the pCI-neo-LACK plasmid by a two steps process, wherein first there is a removal of the npt gene, secondly there is an insertion of the fabI gene and the fabI gene promoter into the pCI-bla-LACK vector to obtain pCI-bla-LACK-fabI and finally the bla gene is removed, as detailed in Example 1. A fifth aspect of the invention relates to a polynucleotide sequence comprising:
a. a nucleic acid sequence consisting of SEQ ID NO: 1 or a sequence with at least 85% identity to the nucleic acid sequence of SEQ ID NO: 1; or
b. a nucleic acid sequence encoding an amino acid sequence consisting of SEQ ID NO: 2 or an amino acid sequence with at least 90% identity to SEQ ID NO: 2; and
c. a nucleic acid sequence consisting of SEQ ID NO: 5 or a sequence with at least 85% identity to the nucleic acid sequence of SEQ ID NO:5; or
d. a nucleic acid sequence encoding an amino acid sequence consisting of SEQ ID NO: 6 or an amino acid sequence with at least 90% identity to SEQ ID NO: 6, for use as a medicament.

It further relates to said polynucleotide sequence for use in the therapeutic or prophylactic treatment of a disease, for use in enhancing or inducing a prophylactic or therapeutic immune response in a mammalian subject and to a method of therapeutic or prophylactic treatment wherein such treatment comprises administering to a mammalian subject a therapeutically effective amount of said polynucleotide.

Further details and preferred embodiments of said polynucleotide and its medical use have been provided under the previous aspects of the invention.

A sixth aspect of the invention relates to a polynucleotide sequence comprising:
a. a nucleic acid sequence consisting of SEQ ID NO: 1 or a sequence with at least 85% identity to the nucleic acid sequence of SEQ ID NO: 1; or
b. a nucleic acid sequence encoding an amino acid sequence consisting of SEQ ID NO: 2 or an amino acid sequence with at least 90% identity to SEQ ID NO: 2; and
c. a nucleic acid sequence consisting of SEQ ID NO: 5 or a sequence with at least 85% identity to the nucleic acid sequence of SEQ ID NO:5; or
d. a nucleic acid sequence encoding an amino acid sequence consisting of SEQ ID NO: 6 or an amino acid sequence with at least 90% identity to SEQ ID NO: 6, for use in the prophylactic or therapeutic treatment of an infectious disease.

It further relates to a method of therapeutic or prophylactic treatment against an infectious disease wherein such treatment comprises administering to a mammalian subject a therapeutically effective amount of said polynucleotide.

In a preferred embodiment, the invention relates to said polynucleotide sequence for use in the therapeutic or prophylactic treatment of leishmaniasis, preferably for use in the therapeutic or prophylactic treatment of canine leishmaniasis.

In another preferred embodiment, the invention relates to said polynucleotide sequence for use in a therapeutic or prophylactic treatment inducing or enhancing a mammalian subject immune response.

Further details and preferred embodiments of said polynucleotide and its medical uses have been provided under the previous aspects of the invention.

Polynucleotide of the Invention and Protective Th1 Response

In a similar way to other intracellular infectious agents, immunity against *Leishmania* requires the development of an effective cellular immune response. Preferably, the polynucleotide of the invention induces or enhances a specific adaptive cellular response when administered to a mammalian subject. This induction of an effective cellular response is known to be a desirable feature for prophylactic vaccines against leishmaniasis, notably against canine leishmaniasis.

Vaccination strategies are based on the current understanding of the characteristics of an effective anti-*Leishmania* immune response. Murine model studies have provided important knowledge about the role of cellular immunity to control *Leishmania major* infection (Sacks et al., 2002, Nature Reviews 2(11):845-58). Thus, without willing to be bound by theory, resistance to leishmaniasis is related with a predominant T helper 1 (Th1) response, characterized by a high production of IFN-γ_ from the antigen-specific CD4+ T lymphocyte population. Then, these cells are effective in promoting macrophage activation, and the intracellular *Leishmania* are killed in a nitric oxide-dependent manner. On the other hand, T helper 2 (Th2) responses, with production of IL-4 and IL-10 cytokines, are associated with susceptibility and exacerbation of the disease (Heinzel et al., The Journal of Experimental Medicine 1989, 169 (1):59-72; Heinzel et al., Proceedings of the National Academy of Sciences of the United States of America 1991, 88, (16): 7011-5; Muller et al., Immunological Reviews 1989, 112: 95-113.

In the case of canine leishmaniasis, although both types of phenotypic T cells are generally generated, there is increasing evidence for the existence of a correlation between Th1 and Th2 responses and control and progression of the disease, respectively being the balance between both types of responses determinant for the final outcome (Brachelente et al., Veterinary Pathology 2005, 42(2):166-75; Chamizo C. et al., Veterinary Immunology and Immunopathology 2005, 103 (1-2):67-75; Pinelli E et al., European Journal of Immunology 1995, 25(6):1594-600; Pinelli E et al., Infection and Immunity 1994, 62(1):229-35; Quinnell R J et al., The Journal of Infectious Diseases 2001, 183(9):1421-4; Ramos I et al., Vaccine 2008, 26(3):333-44; Ramos, I., et al., Vaccine 2009, 27(48): 6695-6703).

In a preferred embodiment, the invention relates to said polynucleotide for use in the induction or enhancement of an immune response in the prophylactic or therapeutic treatment of an infectious disease, preferably leishmaniasis, in a mammalian subject. Said immune response is preferably a cellular response characterized by a predominance of CD4+ T helper (Th) lymphocytes Th1 subpopulation versus the Th2 subpopulation. More preferably, the polynucleotide of the invention as described herein provides a protective Th1 response against *Leishmania* infection, in particular against *L. infantum* infection.

Further details and preferred embodiments of said polynucleotide and its medical uses have been provided under the previous aspects of the invention.

Pharmaceutical Composition Comprising a Polynucleotide Sequence

A seventh aspect of the invention relates to a pharmaceutical composition comprising a polynucleotide sequence as defined in the first aspect of the invention, further comprising a polynucleotide sequence encoding one or more antigens, and a pharmaceutically acceptable carrier, additive or excipient.

An eight aspect of the invention relates to a pharmaceutical composition comprising a polynucleotide sequence as defined in the second and subsequent aspects of the invention and further comprising a pharmaceutically acceptable carrier, additive or excipient.

Pharmaceutically acceptable excipients include, but are not limited to, liquids such as water, saline, polyethyleneglycol, hyaluronic acid, glycerol and ethanol.

Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. It is also preferred, that the preparation will contain a pharmaceutically acceptable excipient that serves as a stabilizer, particularly for peptide, protein or other like molecules if they are to be included in the vaccine composition. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, starch, cellulose, sodium or calcium phosphates, citric acid, tartaric acid, glycine, high molecular weight polyethylene glycols (PEGs), and combination thereof. A thorough discussion of pharmaceutically acceptable excipients, additives and carriers is available in Remington's Pharmaceutical Sciences ($22^{nd}$ edition, 2012).

Certain facilitators of polynucleotide molecules uptake and/or expression ("transfection facilitating agents") can also be included in, e. g, non-viral vector compositions, for example, facilitators such as bupivacaine, cardiotoxin and sucrose, and transfection facilitating vehicles such as liposomal or lipid preparations that are routinely used to deliver nucleic acid molecules. Anionic and neutral liposomes are widely available and well known for delivering nucleic acid molecules (see, e. g. Liposomes: A Practical Approach, (1990) RPC New Ed, IRL Press).

Cationic lipid preparations are also well known vehicles for use in delivery of polynucleotide molecules. Suitable lipid preparations include DOTMA (N-[1-(2,3dioleyloxy) propyl]-N, N, N-trimethylammonium chloride), available under the trade name Lipofectin, and DOTAP (1, 2-bis (oleyloxy)-3 (trimethylammonio) propane). These cationic lipids may preferably be used in association with a neutral lipid, for example DOPE (dioleyl phosphatidylethanolamine).

Alternatively, the polynucleotide sequences of the present invention may be encapsulated, adsorbed to, or associated with, particulate carriers. Examples of particulate carriers include those derived from polymethyl methacrylate polymers, as well as microparticles derived from poly(lactides) and poly(lactide-co-glycolides-), known as PLG. Other particulate systems and polymers can also be used, for example, polymers such as polylysine, polyarginine, polyornithine, spermine, spermidine, as well as conjugates of these molecules.

In a particular embodiment, said pharmaceutical composition is a vaccine, with or without addition of an adjuvant substance or composition.

In a particular embodiment, said pharmaceutical composition comprises at least a further adjuvant, as defined above. Preferred adjuvants include any substance that enhances the immune response of a subject to the antigens encoded by the polynucleotide of the invention. They may enhance the immune response by affecting any number of pathways, for example, by stabilizing the antigen/MHC complex, by causing more antigen/MHC complex to be present on the cell surface, by enhancing maturation of antigen presenting cells (APCs), or by prolonging the life of APCs.

Said adjuvant can be a traditional adjuvant such as killed bacteria, bacterial components, aluminum salts, oil emulsions, polysaccharide particles and biopolymers. Preferably, said adjuvant is a molecular adjuvant. Molecular adjuvants are nucleic acid sequences coding for peptides known to stimulate, modify or modulate a host's immune system. Examples of molecular adjuvants for boosting the immunogenicity of DNA vaccines can be plasmids encoding cytokines (e.g., IL-2, IL-12, IFN-γ, GM-CSF or IL-15) as natural immune stimulators. Chemokine-encoding plasmids have also been evaluated for their ability to enhance DNA vaccines. More recently, costimulatory molecules of the TNF ligand/receptor superfamily and signalling molecules have also been investigated as DNA vaccine adjuvants (Saade et al., Expert Rev Vaccines 2012, 11(2): 189-209).

Administration Route and Dosing Schedule

Said polynucleotide and pharmaceutical composition as defined and according to the previous aspects of the invention is formulated to be compatible with its intended route of administration. Methods to accomplish the administration are known to those of ordinary skill in the art. This includes, for example, injections, by parenteral routes such as intravenous, intravascular, intraarterial, subcutaneous, intramuscular, intraperitoneal, intraventricular, intraepidural, or others as well as oral, nasal, ophthalmic, rectal, or topical. Sustained release administration is also specifically contemplated, by such means as depot injections or erodible implants. A preferred route of administration is subcutaneous or intramuscular injection. Another preferred route of administration is intranasal administration.

The dose will be selected according to the administration route, treatment regime and/or administration schedule, having regard to the existing toxicity and effectiveness data.

Vaccination strategies based on prime-boost regimens can be used. These are known to enhance responses against difficult pathogens. These strategies typically involve the priming of the immune responses by using an antigen expressed first by a vector, typically a plasmid DNA, followed by one ore more boosts with administration of the same antigen in a different vector, typically a recombinant virus. This strategy is known as heterologous prime-boost regime. Alternatively, an homologous prime-boost regime can be used wherein the same antigen encoding vector is used for the priming and boosting steps. Preferably, said antigen encoding vector is a plasmid DNA.

Accordingly, a preferred administration regime for said polynucleotide or pharmaceutical composition is a homologous prime-boost regime, preferably wherein said polynucleotide is a bacterial plasmid polynucleotide, more preferably said polynucleotide is the pPAL-LACK vector.

A suitable unit dose for vaccination is 5-20 µg DNA-encoding antigen/per kg of body weight, and such dose is preferably administered 1, 2 or 3 times (preferably in an homologous regime) and with an interval of 1-3 weeks. For instance, priming is carried out at day −60 and boost at day −30 or −45 before the infection or day of planned exposure to the infectious agent.

In a particular embodiment, said polynucleotide as defined and according to the previous aspects of the invention is used with other drugs to provide a combination prophylactic or therapeutic treatment. The other drugs, may form part of the same composition, or be provided as a separate composition for administration at the same time or at different time.

Further details and preferred embodiments of said pharmaceutical composition and its medical uses have been provided under the previous aspects of the invention.

The Polynucleotide of the Invention for Immunization of a Mammal

A ninth aspect of the invention relates to an antibody, including a fragment thereof, preferably selected from the list consisting of Fab, Fab', Fab'-SH, Fv, scFv, F(ab')2, Vhh, nanobody and diabody, obtained or obtainable after immunization of a mammal with the polynucleotide as defined in the first and second aspects of the invention, the polynucleotide according to the forth, fifth or sixth aspects of the invention or a pharmaceutical composition comprising thereof, wherein said antibody or fragment thereof is suitable for the prophylactic or therapeutic treatment of a mammalian subject, preferably for use in passive immunization.

In a related aspect, the invention refers to a method for the obtaining of antibodies comprising the immunization of a mammal, with the polynucleotide as defined in the first and second aspects of the invention, the polynucleotide according to the forth to sixth aspects of the invention or a pharmaceutical composition comprising thereof Said mammal may be a human or a non-human mammal.

In a particular embodiment, it relates to a method for the obtaining of antibodies comprising the immunization of a mammal, preferably a non-human mammal, with the polynucleotide according to the forth aspect of the invention, or a pharmaceutical composition comprising thereof.

Said method may further comprise the isolation and/or purification of the obtained antibodies. Methods for polypeptide isolation and/or purification are well known in the art (see for instance, Isolation and Purification of Proteins, Feb. 5, 2003 by CRC Press, ISBN 9780824707262). Generally, antibody purification comprises a clarification step and once a clarified solution containing the polypeptide of interest has been obtained, its separation from the other proteins produced is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. Affinity chromatography, which exploits a specific interaction between the protein to be purified and an immobilized capture agent, may also be an option for some polypeptides. Preferably, the antibody purification comprises a step of affinity chromatography, more preferably Protein A chromatography.

The term "antibody" is used in the broadest sense and includes fully assembled antibodies, monoclonal antibodies, polyclonal antibodies, multispecific antibodies (e.g., bispecific antibodies), antigen-binding antibody fragments (e.g., Fab, Fab', F (ab')2, Fv, single chain antibodies, diabodies), camelbodies and recombinant peptides comprising the forgoing as long as they exhibit the desired biological activity.

An "antibody fragment" or "antigen-binding antibody fragment" of an antibody hereby is defined as a fragment of an antibody (e.g., a variable region of an IgG) that is sufficient to confer specific antigen binding to the polypeptide, as long as the antibody retains the desired biological activity. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs.

Nonlimiting examples of antibody fragments include Fab, Fab', F(ab')2, Fv, domain antibody (dAb), complementarity determining region (CDR) fragments, single-chain antibodies (scFv), single chain antibody fragments, diabodies, triabodies, tetrabodies, minibodies, linear antibodies [Johnson G, Wu T T. (2000) Kabat database and its applications: 30 years after the first variability plot. Nucleic Acids Res. 28:214-218]; chelating recombinant antibodies, tribodies or bibodies, intrabodies, nanobodies, small modular immunopharmaceuticals (SMI Ps), an antigen-binding-domain immunoglobulin fusion protein, a camelized antibody, a VHH containing antibody, or muteins or derivatives thereof; and multispecific antibodies formed from antibody fragments [Chothia C, Lesk A M. (1987)

Plasmid Sequences

Legend:

Bold Multiple cloning site (MCS) or PacI restriction site

Underline LACK gene

Double underline FabI gene including promoter (key elements −35 box, −10 box and TF-binding site—in italics).

Capital letters FabI promoter within this sequence of the *E. coli* genome pCI-bla-fab1-LACK (SEQ ID NO: 22)

```
   1 tcaatattgg ccattagcca tattattcat tggttatata gcataaatca atattggcta
  61 ttggccattg catacgttgt atctatatca taatatgtac atttatattg gctcatgtcc
 121 aatatgaccg ccatgttggc attgattatt gactagttat taatagtaat caattacggg
 181 gtcattagtt catagcccat atatggagtt ccgcgttaca taacttacgg taaatggccc
 241 gcctggctga ccgcccaacg accccgccc attgacgtca ataatgacgt atgttcccat
 301 agtaacgcca atagggactt tccattgacg tcaatgggtg gagtatttac ggtaaactgc
 361 ccacttggca gtacatcaag tgtatcatat gccaagtccg cccctattg acgtcaatga
 421 cggtaaatgg cccgcctggc attatgccca gtacatgacc ttacgggact ttcctacttg
 481 gcagtacatc tacgtattag tcatcgctat taccatggtg atgcggtttt ggcagtacac
 541 caatgggcgt ggatagcggt ttgactcacg ggatttcca gtctccacc ccattgacgt
 601 caatgggagt ttgttttggc accaaaatca acgggacttt ccaaaatgtc gtaacaactg
 661 cgatcgcccg ccccgttgac gcaaatgggc ggtaggcgtg tacggtggga ggtctatata
 721 agcagagctc gtttagtgaa ccgtcagatc actagaagct ttattgcggt agtttatcac
 781 agttaaattg ctaacgcagt cagtgcttct gacacaacag tctcgaactt aagctgcagt
 841 gactctctta aggtagcctt gcagaagttg gtcgtgaggc actgggcagg taagtatcaa
 901 ggttacaaga caggtttaag gagaccaata gaaactgggc ttgtcgagac agagaagact
 961 cttgcgtttc tgataggcac ctattggtct tactgacatc cactttgcct ttctctccac
1021 aggtgtccac tcccagttca attacagctc ttaaggctag agtacttaat acgactcact
1081 ataggctagc ctcgagaatt caccatgaac tacgagggtc acctgaaggg ccaccgcgga
1141 tgggtcacct ccctggcctg cccgcagcag gcgggtcgt acatcaaggt ggtgtcgacg
1201 tcgcgcgatg gcacggccat ctcgtggaaa gccaaccccg accgccacag cgtggacagc
1261 gactacggtc tgccgagcca ccgcctcgag ggccacaccg gcttcgtgtc gtgtgtgtcg
1321 ctggcccacg ccaccgacta cgcgctgacc gcgtcctggg accgctccat ccgcatgtgg
1381 gacctgcgca atggccagtg ccagcgcaag ttcctgaagc acaccaagga cgtgctcgcc
1441 gtcgccttct cgccggacga ccgcctgatc gtgtccgcgg gccgcgacaa cgtgatccgc
1501 gtgtggaacg tggcgggcga gtgcatgcac gagttcctgc gcgacggcca cgaggactgg
1561 gtgagcagca tctgtttctc gccgtcgctg gagcatccga tcgtggtgtc cggcagctgg
1621 gacaacacca tcaaggtatg gaacgtgaac gggggcaagt gtgagcgcac gctcaagggc
1681 cacagcaact acgtgtccac ggtgacggtg tcgccagacg ggtcgctgtg cgcgtccggc
1741 ggcaaggacg gcgcggcgct gctgtgggac ctgagcaccg gcgagcagct gttcaagatc
1801 aacgtggagt cgcccatcaa ccagatcgcc ttctcgccca accgcttctg gatgtgcgtc
1861 gcgacggaga ggtctctgtc cgtgtacgac ctggagagca aggctgtgat tgcggagctg
1921 acgccggacg gcgcgaagcc gtccgagtgc atctccattg cctggtccgc cgacggcaac
1981 actctgtact ccggtcacaa ggacaacctg atccgcgtgt ggtccatctc cgacgccgag
2041 taactagagt cgacccgggc ggccgcttcc ctttagtgag ggttaatgct tcgagcagac
2101 atgataagat acattgatga gtttggacaa accacaacta gaatgcagtg aaaaaaatgc
2161 tttatttgtg aaatttgtga tgctattgct ttatttgtaa ccattataag ctgcaataaa
2221 caagttaaca acaacaattg cattcatttt atgtttcagg ttcaggggga gatgtgggag
2281 gttttttaaa gcaagtaaaa cctctacaaa tgtggtaaaa tccgataagg atcgatccgg
2341 gctggcgtaa tagcgaagag gcccgcaccg atcgcccttc ccaacagttg cgcagcctga
```

-continued

```
2401 atggcgaatg gacgcgccct gtagcggcgc attaagcgcg gcgggtgtgg tggttacgcg
2461 cagcgtgacc gctacacttg ccagcgttaa ttaaGTGCTG GAGAATATTC GGCAAGGTCT
2521 GAACCGTCCC AGCCATCGCC ATGAAAGGGT TAGGGCTGT ATGAGCCTGT TGTTGCTGG
2581 GGTAACAATA TTTGCACAAT ACGGTCCCCT CGCCCCTCTG GGGAGAGGGT TAGGGTGAGG
2641 GGAAAAGCGC CCCCCCTGCC GCAGCCTGCT CCGGTCGGAC CTGGCAACTA TAGCTACTCA
2701 CAGCCAGGTT GATTATAATA ACCGTTTATC TGTTCGTACT GTTTACTAAA CGACGAATC
2761 GCCTGATTTT CAGGCACAAC AAGCATCAAC AATAAGGATT AAAGCTatgg gttttctttc
2821 cggtaagcgc attctggtaa ccggtgttgc cagcaaacta tccatcgcct acggtatcgc
2881 tcaggcgatg caccgcgaag gagctgaact ggcattcacc taccagaacg acaaactgaa
2941 aggccgcgta gaagaatttg ccgctcaatt gggttctgac atcgttctgc agtgcgatgt
3001 tgcagaagat gccagcatcg acaccatgtt cgctgaactg gggaaagttt ggccgaaatt
3061 tgacggtttc gtacactcta ttggttttgc acctggcgat cagctggatg gtgactatgt
3121 taacgccgtt acccgtgaag gcttcaaaat tgcccacgac atcagctcct acagcttcgt
3181 tgcaatggca aaagcttgcc gctccatgct gaatccgggt tctgccctgc tgaccctttc
3241 ctaccttggc gctgagcgcg ctatcccgaa ctacaacgtt atgggtctgg caaaagcgtc
3301 tctggaagcg aacgtgcgct atatggcgaa cgcgatgggt ccggaaggtg tgcgtgttaa
3361 cgccatctct gctggtccga tccgtactct ggcggcttcc ggtatcaaag acttccgcaa
3421 aatgctggct cattgcgaag ccgttacccc gattcgccgt accgttacta ttgaagatgt
3481 gggtaactct gcggcattcc tgtgctccga tctctctgcc ggtatctccg gtgaagtagt
3541 ccacgttgac ggcggtttca gcatcgctgc aatgaacgaa ctcgaactga aataattaat
3601 taaccgcgta ccgcgtatgg tgcactctca gtacaatctg ctctgatgcc gcatagttaa
3661 gccagcccg acacccgcca cacccgctg acgcgccctg acgggcttgt ctgctcccgg
3721 catccgctta cagacaagct gtgaccgtct ccgggagctg catgtgtcag aggttttcac
3781 cgtcatcacc gaaacgcgcg agacgaaagg gcctcgtgat acgcctattt ttataggtta
3841 atgtcatgat aataatggtt tcttagacgt caggtggcac ttttcgggga atgtgcgcg
3901 gaaccctat tgtttattt tctaaatac attcaaatat gtatccgctc atgagacaat
3961 aaccctgata atgcttcaa taatattgaa aaggaagag tatgagtatt caacatttcc
4021 gtgtcgccct tattcccttt tttgcggcat tttgccttcc tgtttttgct cacccagaaa
4081 cgctggtgaa agtaaaagat gctgaagatc agttgggtgc acgagtggg tacatcgaac
4141 tggatctcaa cagcggtaag atccttgaga gttttcgccc cgaagaacgt tttccaatga
4201 tgagcacttt taaagttctg ctatgtggcg cggtattatc ccgtattgac gccgggcaag
4261 agcaactcgg tcgccgcata cactattctc agaatgactt ggttgagtac tcaccagtca
4321 cagaaaagca tcttacggat ggcatgacag taagagaatt atgcagtgct gccataacca
4381 tgagtgataa cactgcggcc aacttacttc tgacaacgat cggaggaccg aaggagctaa
4441 ccgctttttt gcacaacatg ggggatcatg taactcgcct tgatcgttgg gaaccggagc
4501 tgaatgaagc cataccaaac gacgagcgtg acaccacgat gcctgtagca atggcaacaa
4561 cgttgcgcaa actattaact ggcgaactac ttactctagc ttcccggcaa caattaatag
4621 actggatgga ggcggataaa gttgcaggac cacttctgcg ctcggccctt ccggctggct
4681 ggtttattgc tgataaatct ggagccggtg agcgtgggtc tcgcggtatc attgcagcac
4741 tggggccaga tggtaagccc tcccgtatcg tagttatcta cacgacgggg agtcaggcaa
```

-continued

```
4801 ctatggatga acgaaataga cagatcgctg agataggtgc ctcactgatt aagcattggt
4861 aactgtcaga ccaagtttac tcatatatac tttagattga tttaaaactt cattttaat
4921 ttaaaaggat ctaggtgaag atccttttg ataatctcat gaccaaaatc ccttaacgtg
4981 agttttcgtt ccactgagcg tcagacccg tagaaaagat caaaggatct tcttgagatc
5041 cttttttct gcgcgtaatc tgctgcttgc aaacaaaaaa accaccgcta ccagcggtgg
5101 tttgtttgcc ggatcaagag ctaccaactc tttttccgaa ggtaactggc ttcagcagag
5161 cgcagatacc aaatactgtc cttctagtgt agccgtagtt aggccaccac ttcaagaact
5221 ctgtagcacc gcctacatac ctcgctctgc taatcctgtt accagtggct gctgccagtg
5281 gcgataagtc gtgtcttacc gggttggact caagacgata gttaccggat aaggcgcagc
5341 ggtcgggctg aacggggggt tcgtgcacac agcccagctt ggagcgaacg acctacaccg
5401 aactgagata cctacagcgt gagctatgag aaagcgccac gcttcccgaa gggagaaagg
5461 cggacaggta tccggtaagc ggcagggtcg gaacaggaga gcgcacgagg gagcttccag
5521 ggggaaacgc ctggtatctt tatagtcctg tcgggtttcg ccacctctga cttgagcgtc
5581 gatttttgtg atgctcgtca gggggcgga gcctatggaa aaacgccagc aacgcggcct
5641 ttttacggtt cctggccttt tgctggcctt ttgctcacat ggctcgacag atct
``` pPAL-LACK
(SEQ ID NO: 23)

```
   1 tcaatattgg ccattagcca tattattcat tggttatata gcataaatca atattggcta
  61 ttggccattg catacgttgt atctatatca taatatgtac atttatattg gctcatgtcc
 121 aatatgaccg ccatgttggc attgattatt gactagttat taatagtaat caattacggg
 181 gtcattagtt catagcccat atatggagtt ccgcgttaca acttacgg taaatggccc
 241 gcctggctga ccgcccaacg accccgccc attgacgtca ataatgacgt atgttcccat
 301 agtaacgcca atagggactt tccattgacg tcaatgggtg gagtatttac ggtaaactgc
 361 ccacttggca gtacatcaag tgtatcatat gccaagtccg cccctattg acgtcaatga
 421 cggtaaatgg cccgcctggc attatgccca gtacatgacc ttacgggact ttcctacttg
 481 gcagtacatc tacgtattag tcatcgctat taccatggtg atgcggtttt ggcagtacac
 541 caatgggcgt ggatagcggt ttgactcacg gggatttcca agtctccacc ccattgacgt
 601 caatgggagt ttgttttggc accaaaatca acgggacttt ccaaaatgtc gtaacaactg
 661 cgatcgcccg ccccgttgac gcaaatgggc ggtaggcgtg tacggtggga ggtctatata
 721 agcagagctc gtttagtgaa ccgtcagatc actagaagct ttattgcggt agtttatcac
 781 agttaaattg ctaacgcagt cagtgcttct gacacaacag tctcgaactt aagctgcagt
 841 gactctctta aggtagcctt gcagaagttg gtcgtgaggc actgggcagg taagtatcaa
 901 ggttacaaga caggtttaag gagaccaata gaaactgggc ttgtcgagac agagaagact
 961 cttgcgtttc tgataggcac ctattggtct tactgacatc cactttgcct ttctctccac
1021 aggtgtccac tcccagttca attacagctc ttaaggctag agtacttaat acgactcact
1081 ataggctagc ctcgagaatt caccatgaac tacgaggtc acctgaaggg ccaccgcgga
1141 tgggtcacct ccctggcctg cccgcagcag gcggggtcgt acatcaaggt ggtgtcgacg
1201 tcgcgcgatg gcacggccat ctcgtggaaa gccaacccg accgccacag cgtggacagc
1261 gactacggtc tgccgagcca ccgcctcgag ggccacaccg gcttcgtgtc gtgtgtgtcg
1321 ctggcccacg ccaccgacta cgcgctgacc gcgtcctggg accgctccat ccgcatgtgg
1381 gacctgcgca atggccagtg ccagcgcaag ttcctgaagc acaccaagga cgtgctcgcc
1441 gtcgccttct cgccggacga ccgcctgatc gtgtccgcgg gccgcgacaa cgtgatccgc
```

-continued

```
1501 gtgtggaacg tggcgggcga gtgcatgcac gagttcctgc gcgacggcca cgaggactgg
1561 gtgagcagca tctgtttctc gccgtcgctg gagcatccga tcgtggtgtc cggcagctgg
1621 gacaacacca tcaaggtatg gaacgtgaac gggggcaagt gtgagcgcac gctcaagggc
1681 cacagcaact acgtgtccac ggtgacggtg tcgccagacg ggtcgctgtg cgcgtccgc
1741 ggcaaggacg gcgcggcgct gctgtgggac ctgagcaccg gcgagcagct gttcaagatc
1801 aacgtggagt cgcccatcaa ccagatcgcc ttctcgccca accgcttctg gatgtgcgtc
1861 gcgacggaga ggtctctgtc cgtgtacgac ctggagagca aggctgtgat tgcggagctg
1921 acgccggacg gcgcgaagcc gtccgagtgc atctccattg cctggtccgc cgacggcaac
1981 actctgtact ccggtcacaa ggacaacctg atccgcgtgt ggtccatctc cgacgccgag
2041 taactagagt cgacccgggc ggccgcttcc ctttagtgag ggttaatgct tcgagcagac
2101 atgataagat acattgatga gtttggacaa accacaacta gaatgcagtg aaaaaaatgc
2161 tttatttgtg aaatttgtga tgctattgct ttatttgtaa ccattataag ctgcaataaa
2221 caagttaaca acaacaattg cattcatttt atgtttcagg ttcagggga gatgtgggag
2281 gttttttaaa gcaagtaaaa cctctacaaa tgtggtaaaa tccgataagg atcgatccgg
2341 gctggcgtaa tagcgaagag gcccgcaccg atcgcccttc ccaacagttg cgcagcctga
2401 atggcgaatg gacgcgccct gtagcggcgc attaagcgcg gcgggtgtgg tggttacgcg
2461 cagcgtgacc gctacacttg ccagcgttaa ttaaGTGCTG GAGAATATTC GGCAAGGTCT
2521 GAACCGTCCC AGCCATCGCC ATGAAAGGGT TAGGGGCTGT ATGAGCCTGT TTGTTGCTGG
2581 GGTAACAATA TTTGCACAAT ACGGTCCCCT CGCCCCTCTG GGGAGAGGGT TAGGGTGAGG
2641 GGAAAAGCGC CCCCCCTGCC GCAGCCTGCT CCGGTCGGAC CTGGCAACTA TAGCTACTCA
2701 CAGCCAGGTT GATTATAATA ACCGTTTATC TGTTCGTACT GTTTACTAAA ACGACGAATC
2761 GCCTGATTTT CAGGCACAAC AAGCATCAAC AATAAGGATT AAAGCTatgg gttttcttc
2821 cggtaagcgc attctggtaa ccggtgttgc cagcaaacta tccatcgcct acgtatcgc
2881 tcaggcgatg caccgcgaag gagctgaact ggcattcacc taccagaacg acaaactgaa
2941 aggccgcgta gaagaatttg ccgctcaatt gggttctgac atcgttctgc agtgcgatgt
3001 tgcagaagat gccagcatcg acaccatgtt cgctgaactg gggaaagttt ggccgaaatt
3061 tgacggtttc gtacactcta ttggttttgc acctggcgat cagctggatg gtgactatgt
3121 taacgccgtt acccgtgaag gcttcaaaat tgcccacgac atcagctcct acagcttcgt
3181 tgcaatggca aaagcttgcc gctccatgct gaatccggt tctgccctgc tgaccctttc
3241 ctaccttggc gctgagcgcg ctatcccgaa ctacaacgtt atgggtctgg caaaagcgtc
3301 tctggaagcg aacgtgcgct atatggcgaa cgcgatgggt ccggaaggtg tgcgtgttaa
3361 cgccatctct gctggtccga tccgtactct ggcggcttcc ggtatcaaag acttccgcaa
3421 aatgctggct cattgcgaag ccgttacccc gattcgccgt accgttacta ttgaagatgt
3481 gggtaactct gcggcattcc tgtgctccga tctctctgcc ggtatctccg gtgaagtagt
3541 ccacgttgac ggcggtttca gcatcgctgc aatgaacgaa ctcgaactga aataattaat
3601 taaccgcgta tggtgcactc tcagtacaat ctgctctgat gccgcatagt taagccagcc
3661 ccgacacccg ccaacacccg ctgacgcgcc ctgacgggct tgtctgctcc cggcatccgc
3721 ttacagacaa gctgtgaccg tctccgggag ctcatgtgtc agaggttttc acaagttgca
3781 ggaccacttc tgcgctcggc ccttccggct ggctggttta ttgctgataa atctggagcc
3841 ggtgagcgtg gtctctcgcgg tatcattgca gcactggggc cagatggtaa gccctcccgt
```

-continued

```
3901 atcgtagtta tctacacgac ggggagtcag gcaactatgg atgaacgaaa tagacagatc 3961 gctgagatag gtgcctcact gattaagcat tggtaactgt cagaccaagt ttactcatat 4021 atactttaga ttgatttaaa acttcatttt taatttaaaa ggatctaggt gaagatcctt 4081 tttgataatc tcatgaccaa atcccttaa cgtgagtttt cgttccactg agcgtcagac 4141 cccgtagaaa agatcaaagg atcttcttga gatcctttt ttctgcgcgt aatctgctgc 4201 ttgcaaacaa aaaaccacc gctaccagcg gtggtttgtt tgccggatca agagctacca 4261 actcttttc gaaggtaac tggcttcagc agagcgcaga taccaaatac tgtccttcta 4321 gtgtagccgt agttaggcca ccacttcaag aactctgtag caccgcctac atacctcgct 4381 ctgctaatcc tgttaccagt ggctgctgcc agtggcgata agtcgtgtct taccgggttg 4441 gactcaagac gatagttacc ggataaggcg cagcggtcgg gctgaacggg gggttcgtgc 4501 acacagccca gcttggagcg aacgacctac accgaactga gatacctaca gcgtgagcta 4561 tgagaaagcg ccacgcttcc cgaagggaga aaggcggaca ggtatccggt aagcggcagg 4621 gtcggaacag gagagcgcac gagggagctt ccaggggggaa acgcctggta tctttatagt 4681 cctgtcgggt ttcgccacct ctgacttgag cgtcgatttt tgtgatgctc gtcaggggg 4741 cggagcctat ggaaaaacgc cagcaacgcg ccttttttac ggttcctggc cttttgctgg 4801 cctttttgctc acatggctcg acagatct
``` pPAL (SEQ ID NO: 24)

```
   1 tcaatattgg ccattagcca tattattcat tggttatata gcataaatca atattggcta 61 ttggccattg catacgttgt atctatatca taatatgtac atttatattg gctcatgtcc 121 aatatgaccg ccatgttggc attgattatt gactagttat taatagtaat caattacggg 181 gtcattagtt catagcccat atatggagtt ccgcgttaca taacttacgg taaatggccc 241 gcctggctga ccgcccaacg accccgccc attgacgtca ataatgacgt atgttcccat 301 agtaacgcca atagggactt tccattgacg tcaatgggtg gagtatttac ggtaaactgc 361 ccacttggca gtacatcaag tgtatcatat gccaagtccg cccctattg acgtcaatga 421 cggtaaatgg cccgcctggc attatgccca gtacatgacc ttacgggact ttcctacttg 481 gcagtacatc tacgtattag tcatcgctat taccatggtg atgcggtttt ggcagtacac 541 caatgggcgt ggatagcggt ttgactcacg gggatttcca gtctccacc ccattgacgt 601 caatgggagt ttgttttggc accaaaatca acgggacttt ccaaaatgtc gtaacaactg 661 cgatcgcccg ccccgttgac gcaaatgggc ggtaggcgtg tacggtggga ggtctatata 721 agcagagctc gtttagtgaa ccgtcagatc actagaagct ttattgcggt agtttatcac 781 agttaaattg ctaacgcagt cagtgcttct gacacaacag tctcgaactt aagctgcagt 841 gactctctta aggtagcctt gcagaagttg gtcgtgaggc actgggcagg taagtatcaa 901 ggttacaaga caggtttaag gagaccaata gaaactgggc ttgtcgagac agagaagact 961 cttgcgtttc tgataggcac ctattggtct tactgacatc cactttgcct ttctctccac 1021 aggtgtccac tcccagttca attacagctc ttaaggctag agtacttaat acgactcact

1081 ataggctagc ctcgagaatt cacgcgtggt acctctagag tcgacccggg cggccgcttc 1141 cctttagtga gggttaatgc ttcgagcaga catgataaga tacattgatg agtttggaca 1201 aaccacaact agaatgcagt gaaaaaaatg ctttatttgt gaaatttgtg atgctattgc 1261 tttatttgta accattataa gctgcaataa acaagttaac aacaacaatt gcattcattt 1321 tatgtttcag gttcaggggg agatgtggga ggtttttttaa agcaagtaaa acctctacaa 1381 atgtggtaaa atccgataag gatcgatccg gctggcgta atagcgaaga ggcccgcacc
```

-continued

```
1441 gatcgccctt cccaacagtt gcgcagcctg aatggcgaat ggacgcgccc tgtagcggcg
1501 cattaagcgc ggcgggtgtg gtggttacgc gcagcgtgac cgctacactt gccagcgtta
1561 attaaGTGCT GGAGAATATT CGGCAAGGTC TGAACCGTCC CAGCCATCGC CATGAAAGGG
1621 TTAGGGGCTG TATGAGCCTG TTTGTTGCTG GGGTAACAAT ATTTGCACAA TACGGTCCCC
1681 TCGCCCCTCT GGGGAGAGGG TTAGGGTGAG GGGAAAAGCG CCCCCCCTGC CGCAGCCTGC
1741 TCCGGTCGGA CCTGGCAACT ATAGCTACTC ACAGCCAGGT TGATTATAAT AACCGTTTAT
1801 CTGTTCGTAC TGTTTACTAA AACGACGAAT CGCCTGATTT TCAGGCACAA CAAGCATCAA
1861 CAATAAGGAT TAAAGCTatg ggttttcttt ccggtaagcg cattctggta accggtgttg
1921 ccagcaaact atccatcgcc tacggtatcg ctcaggcgat gcaccgcgaa ggagctgaac
1981 tggcattcac ctaccagaac gacaaactga aaggccgcgt agaagaattt gccgctcaat
2041 tgggttctga catcgttctg cagtgcgatg ttgcagaaga tgccagcatc gacaccatgt
2101 tcgctgaact ggggaaagtt tggccgaaat ttgacggttt cgtacactct attggttttg
2161 cacctggcga tcagctggat ggtgactatg ttaacgccgt tacccgtgaa ggcttcaaaa
2221 ttgcccacga catcagctcc tacagcttcg ttgcaatggc aaaagcttgc cgctccatgc
2281 tgaatccggg ttctgccctg ctgacccttt cctaccttgg cgctgagcgc gctatcccga
2341 actacaacgt tatgggtctg gcaaaagcgt ctctggaagc gaacgtgcgc tatatggcga
2401 acgcgatggg tccggaaggt gtgcgtgtta acgccatctc tgctggtccg atccgtactc
2461 tggcggcttc cggtatcaaa gacttccgca aaatgctggc tcattgcgaa gccgttaccc
2521 cgattcgccg taccgttact attgaagatg tgggtaactc tgcggcattc ctgtgctccg
2581 atctctctgc cggtatctcc ggtgaagtag tccacgttga cggcggtttc agcatcgctg
2641 caatgaacga actcgaactg aaataattaa ttaaccgcgt atggtgcact ctcagtacaa
2701 tctgctctga tgccgcatag ttaagccagc cccgacaccc gccaacaccc gctgacgcgc
2761 cctgacgggc ttgtctgctc ccggcatccg cttacagaca agctgtgacc gtctccggga
2821 gctcatgtgt cagaggtttt cacaagttgc aggaccactt ctgcgctcgg cccttccggc
2881 tggctggttt attgctgata atctggagc cggtgagcgt gggtctcgcg gtatcattgc
2941 agcactgggg ccagatggta agccctcccg tatcgtagtt atctacacga cggggagtca
3001 ggcaactatg gatgaacgaa atagacagat cgctgagata ggtgcctcac tgattaagca
3061 ttggtaactg tcagaccaag tttactcata tatactttag attgatttaa aacttcattt
3121 ttaatttaaa aggatctagg tgaagatcct ttttgataat ctcatgacca aaatccctta
3181 acgtgagttt tcgttccact gagcgtcaga ccccgtagaa aagatcaaag gatcttcttg
3241 agatcctttt tttctgcgcg taatctgctg cttgcaaaca aaaaaaccac cgctaccagc
3301 ggtggtttgt ttgccggatc aagagctacc aactctttt ccgaaggtaa ctggcttcag
3361 cagagcgcag ataccaaata ctgtccttct agtgtagccg tagttaggcc accacttcaa
3421 gaactctgta gcaccgccta catacctcgc tctgctaatc ctgttaccag tggctgctgc
3481 cagtggcgat aagtcgtgtc ttaccgggtt ggactcaaga cgatagttac cggataaggc
3541 gcagcggtcg ggctgaacgg ggggttcgtg cacacagccc agcttggagc gaacgaccta
3601 caccgaactg agatacctac agcgtgagct atgagaaagc gccacgcttc ccgaagggag
3661 aaaggcggac aggtatccgg taagcggcag ggtcggaaca ggagagcgca cgagggagct
```

```
-continued
3721 tccaggggga aacgcctggt atctttatag tcctgtcggg tttcgccacc tctgacttga 3781 gcgtcgattt ttgtgatgct cgtcaggggg gcggagccta tggaaaaacg ccagcaacgc 3841 ggccttttta cggttcctgg ccttttgctg gccttttgct cacatggctc gacagatct
```

It will be understood that particular embodiments described in the Examples are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijessen, ed.); Fundamental Virology, 2nd Edition, vol. I & II (B. N. Fields and D. M. Knipe, eds.).

The use of the word "a" or "an" may mean "one," but it is also consistent with the meaning of "one or more", "at least one," and "one or more than one."

Throughout this application, the term "about" means the indicated value ±5% of its value, preferably the indicated value ±2% of its value, most preferably the term "about" means exactly the indicated value (±0%).

EXAMPLES

Example 1.—Material and Methods

1. Generation of the pPAL-LACK Vector
1.1. Obtaining the Fab I Gene and its Promoter from *E. Coli* Genomic DNA by PCR

*E. coli* Genomic DNA Extraction

From an *E. coli* colony culture of the strain BL21 (DE3) strain (New England Biolabs, genotype fhuA2[lon] ompT gal (λ DE3) [dcm] ΔhsdS; main features: deficient in Lon and ompT proteases, resistant to phage T1) in a flask in 10 ml of Luria Bertani (LB) at 37° C. kept under stirring overnight (150 rpm) and to an Optical Density (OD) of 0.1 (at 550 nm), it was scaled to a total volume of 25 ml. It was allowed to grow to an OD of 0.5 (at 550 nm) and collected by centrifugation at 15,000 g 5' at room temperature. The cell pellet was washed with 50 ml of TES buffer (50 mM NaCl, 50 mM TrisHCl pH=8.0, 5 mM EDTA), centrifuged again and resuspended in 100 µl of lysis buffer (25% sucrose, 40 µg/ml RNase A, 1 mg/ml lysozyme, 0.1M NaCl, 50 mM TrisHCl pH=8.0, 10 mm EDTA). Lysis was allowed for a maximum of 20 minutes and then 100 µl of 2% SDS were added. It was mixed by vortex for 3 minutes and frozen and thawed four times quickly in liquid nitrogen. Subsequently, proteinase k was added at a final concentration of 10 µg/ml and incubated for 30 minutes at 30° C. After this time, phenolization was carried out. First, the above mixture was brought to a volume of 500 µl by adding the necessary amount of milliQ water. Next, 1 volume of a 25:24:1 phenol:chloroform:isoamyl alcohol mixture was added and it was emulsified by vigorous shaking for 20". It was centrifuged at 15,000 g for 5' at room temperature and the aqueous phase (upper) was carefully recovered by drawing slowly from the meniscus to avoid contamination with the contents of the interface. Next, 1 volume of 24:1 chloroform:isoamyl alcohol was added to the recovered aqueous phase and the phases were re-emulsified and separated as described. Finally, DNA precipitation was carried out by adding 0.1 volume of 3 M sodium acetate pH 5.2 and 2.5 volumes of absolute ethanol pre-cooled at −20° C. The sample was allowed to precipitate at −20° C. for at least 30'. Next, it was centrifuged at 15,000 g at 4° C. for 20', the supernatant was carefully discarded, washing was performed with 500 µl of 70% ethanol and the pellet was allowed to air dry at room temperature after discarding the supernatant. To conclude, the pellet was resuspended in 350 µl of TE buffer (Tris HCl pH=8.0, EDTA).

Amplification of the Fab I Gene and its Promoter by Polymerase Chain Reaction (PCR) Oligonucleotide primers were designed for amplification of the promoter of the fab I gene followed by said gene from genomic DNA of the BL21 strain of *E. coli*. Said oligonucleotides contain the target of the restriction endonuclease Pac I at position 5 min, in addition to any short nucleotide sequence to enable enzyme catalysis, since it needs a minimum substrate on which make the cut. Taking into account these requirements, the primers that were obtained were as follows:

```
(PacI-fabI-promoter-Fw):
                                          SEQ ID NO: 8
5'TACTGGATTAATTAAGTGCTGGAGAATATTCG 3'

(PacI-fabI-Rv):
                                          SEQ ID NO: 9
5' TACTGGATTAATTAATTATTTCAGTTCGAGTTCGTTC 3'
```

In order to carry out the reaction, first, the following was mixed at 4° C. in this order: milliQ water necessary to complete the final volume of the reaction (25 µl), *E. coli* BL21 genomic DNA at 0.2 ng/µl, HiFi buffer (KAPA Biosystems) at 1× (initial concentration–$i_c$–5×), dNTPs mix (dATP, dGTP, dCTP and dTTP) (Invitrogen) at 0.3 mM each ($i_c$=10 mM each), 0.3 µM PacI-fabI-promoter-Fw primer and 0.3 µM PacI-fabI-Rv primer. All these reagents were stored at −20° C. Next, The amplification reaction was performed with the following thermal cycling profile programmed in the Verity thermocycler (Applied Biosystems): 95° C., 5'; 25×[98° C., 20"; 48° C., 15"; 72° C., 30"]; 72° C. 5'. The reaction was performed in octuplicate.

Verification of the PCR Product by Agarose Gel Electrophoresis

In order to analyze the results of the previous amplification reaction, 1 µl of PCR product (4% of the total) was mixed with 4 µl of milliQ water and 1 µl of loading buffer for DNA (30% v/v glycerol, 10 mM EDTA pH 8.0, 0.1% v/v xylene cyanol, 0.1% v/v bromophenol blue in water). On the other hand, a 1% w/v agarose gel (Pronadisa) was prepared in 1×TAE buffer (diluted from 50×TAE: 2 M Tris base, 5.7% v/v glacial acetic acid and 50 mM EDTA pH 8.0) adding the Gel Red dye (initial concentration 10,000×) (Biotium) and the samples were electrophoretically separated in a Mini-SubCell GT (BioRad) system applying a current of 5 V/cm with a Power Pac Basic Power Supply (BioRad) power source for 75 min. 1 Kb Molecular Weight Marker (NEB) was used as size marker. The result was visualized using a Gel Doc XR (BioRad) UV lamp system with the software Quantity One (BioRad).

Purification of the PCR Product

Once the effectiveness of the amplification was checked, the remaining volumes (96%) of the various tubes were the reaction was carried out which had a positive result were mixed and, next, the DNA was purified using the following extraction procedure with organic solvents.

First, the previous mixture was taken to a volume of 500 µl by adding the necessary amount of milliQ water. Next, 1 volume of a mixture of 25:24:1 phenol:chloroform:isoamyl alcohol was added and it was emulsified by vigorous shaking for 20". It was centrifuged at 15,000 g for 5' at room temperature and the aqueous phase (upper) was carefully recovered by drawing slowly from the meniscus to avoid contamination with the contents of the interface. Next, 1 volume of 24:1 chloroform:isoamyl alcohol was added to the recovered aqueous phase and the phases were re-emulsified and separated as described. Finally, DNA precipitation was carried out by adding 0.1 volume of 3 M sodium acetate pH 5.2 and 2.5 volumes of absolute ethanol pre-cooled at −20° C. The sample was allowed to precipitate at −20° C. for at least 30'. Next, it was centrifuged at 15,000 g at 4° C. for 20', the supernatant was carefully discarded, washing was performed with 500 µl of 70% ethanol and the pellet was allowed to air dry at room temperature after discarding the supernatant. To conclude, the pellet was resuspended in 20 µl of milliQ water.

After quantifying the PCR product purified by UV absorption spectrophotometry, which meant further loss of 4.8% of it, digestion with the enzyme Pac I was carried out.

Digestion of the Insert with the Enzyme Pac I

Half the available volume of the purified PCR product (insert) was mixed at a final concentration of 24 ng/µl with the following and in this order: water needed to complete the final volume (total of 20 µl), NEB1 buffer at 1× (initial concentration 10×) (NEB), 0.1 mg/ml bovine serum albumin (BSA; initial concentration, 10 mg/ml) (NEB) and Pac I 0.4 U/µl (initial concentration 10 U/µl) (NEB). The mixture was incubated for 2 hrs at 37° C.

Isolation of the Insert Separated by Agarose Gel Electrophoresis and Purification of the Product from the Gel Electrophoresis on 1% agarose gel was performed as described above of the entire volume of purified PCR product which was subsequently digested with Pac I in order to check its integrity and purify it again after digestion. For the latter purpose, once the electrophoresis was finished, the gel was visualized and the agarose fragment containing the band corresponding to the PCR product was cut with a scalpel. Next, said agarose fragment was weighed and the DNA was purified using the QiaQuick Gel Extraction Kit (Qiagen) following the manufacturer's instructions. Finally, the resulting product was concentrated drying and settling the DNA in a Speed Vac (Savant) vacuum centrifuge and then resuspending it in a volume of 11 µl.

1.2. Preparation of the pPAL-LACK Vector from pCI-Neo-LACK 1.2.1. Purification of the Recombinant Vaccine pCI-Neo-LACK In order to obtain recombinant plasmid pCI-neo-LACK, the E. coli clone of the strain XL10 that contained it (Ramiro, M. J., et al., Vaccine 2003, 21(19-20): 2474-84, obtained from pCIneo plasmid (Promega, GenBank: U47120) was cultured in LB liquid medium (tryptone peptone 10 g/l, yeast extract 5 g/l, NaCl 10 g/l; sterilized in autoclave at 120° C. for 20 min at 1.05 Kg/cm$^2$) with ampicillin at 100 µg/ml at 37° C. for 16 hrs. Next, said plasmid was purified by the method of small scale preparation or miniprep with the High Pure Plasmid Isolation Kit (Roche) following the manufacturer's instructions.

1.2.2. Preparation of the pCI-bla-LACK Vector: Removal of the pCI-Neo-LACK Npt Gene by PCR In order to exclude the npt gene from the pCI-neo-LACK (FIG. 1), and in turn amplifying the fragment of interest, PCR was used again. Said fragment of interest was designated pCIbla-LACK, which acts as a vector in the cloning process, since it includes the replication origin. The bla gene was not removed at this stage because the process was set out in two stages to ensure the viability of the process. Thus, in the first stage the bla gene would be used as selection system to introduce the fab I gene with its promoter, and in the second stage the bla gene would be removed, using the fab I gene as a selection system, thus avoiding using the one that was being introduced as selection system.

Amplification of the pCIbla-LACK fragment was carried out with the following primers, which exclude the sequence of the npt gene but not that of bla and its promoter:

```
(Pac1-pCIbla-1):
                                          SEQ ID NO: 10
5'TACTGGATTAATTAACCGCGTATGGTGCACTCTCA3'

(Pac1-pCIbla-2):
                                          SEQ ID NO: 11
5' TACTGGATTAATTAACGCTGGCAAGTGTAGCGGT 3'
```

The conditions of the amplification reaction were as described in section 1.1., with the following exceptions: the primers described above were used, the purified plasmid as described in section 1.2.1. at a final concentration of 40 µg/µl, hybridization temperature 60° C. instead of 48° C. and extension time at 72° C. of 2' instead of 30".

Analysis and purification of the PCR product of the pCIbla-LACK vector were carried out as it has been detailed in section 1.1. Digestion of the remaining PCR product (91.2%) and purification of the PCR product was performed under the same conditions described in section 1.1. but in a final volume of 100 µl with a concentration of enzyme Pac I of 0.8 U/µl.

Ligation Reaction of the Insert (fabI Gene and its Promoter) with the pCI-bla-LACK Vector to Obtain pCI-bla-LACK-fabI The insert (fabI gene and its promoter) has the following sequence (SEQ ID NO: 21):

```
1 gtgctggaga atattcggca aggtctgaac cgtcccagcc
  atcgccatga aagggttagg
```

-continued

```
  61 ggctgtatga gcctgtttgt tgctggggta acaatatttg
     cacaatacgg tcccctcgcc 121 cctctgggga gagggttagg gtgaggggaa aagcgccccc
     cctgccgcag cctgctccgg 181 tcggacctgg caactatagc tactcacagc caggttgatt
     ataataaccg tttatctgtt 241 cgtactgttt actaaaacga cgaatcgcct gattttcagg
     cacaacaagc atcaacaata 301 aggattaaag ctatgggttt tctttccggt aagcgcattc
     tggtaaccgg tgttgccagc 361 aaactatcca tcgcctacgg tatcgctcag gcgatgcacc
     gcgaaggagc tgaactggca 421 ttcacctacc agaacgacaa actgaaaggc cgcgtagaag
     aatttgccgc tcaattgggt 481 tctgacatcg ttctgcagtg cgatgttgca gaagatgcca
     gcatcgacac catgttcgct 541 gaactgggga aagtttggcc gaaatttgac ggtttcgtac
     actctattgg ttttgcacct 601 ggcgatcagc tggatggtga ctatgttaac gccgttaccc
     gtgaaggctt caaaattgcc 661 cacgacatca gctcctacgg cttcgttgca atggcaaaag
     cttgccgctc catgctgaat 721 ccgggttctg ccctgctgac cctttcctac cttggcgctg
     agcgcgctat cccgaactac 781 aacgttatgg gtctggcaaa agcgtctctg gaagcgaacg
     tgcgctatat ggcgaacgcg 841 atgggtccgg aaggtgtgcg tgttaacgcc atctctgctg
     gtccgatccg tactctggcg 901 gcttccggta tcaaagactt ccgcaaaatg ctggctcatt
     gcgaagccgt taccccgatt 961 cgccgtaccg ttactattga agatgtgggt aactctgcgg
     cattcctgtg ctccgatctc 1021 tctgccggta tctccggtga agtagtccac gttgacggcg
     gtttcagcat cgctgcaatg 1081 aacgaactcg aactgaaata a
```

Before proceeding with the ligation reaction, the insert and the vector were dialyzed using filters (Millipore). Next, quantification of 1 μl of insert and vector was performed by densitometry after performing the corresponding electrophoretic separation on 1% agarose gel as it has been described in section 1.1. For this purpose, after obtaining the image of the gel in the Gel DocXR (BioRad) system, the total loaded amount was calculated using the software Quantity One (BioRad) using the bands resulting from the electrophoretic separation of the size and molecular weight marker 1 Kb Molecular Weight Marker (NEB) as standards. In this manner, the insert and the vector were simultaneously quantified.

In order to perform the ligation reaction, first the following mixture was performed in a final volume of 15 μl in the following order: milliQ water necessary to complete the final volume, 13.3 ng/μl of insert digested and purified (fab I gene and its promoter), digested and purified vector (pCI-bla-LACK), T4 DNA ligase buffer at 1× (initial concentration 10×) (NEB) and 26.7 U Weiss/μl of T4 DNA ligase (initial concentration 400 U Weiss/μl) (NEB). The amount of vector added is defined by an insert:vector equimolar ratio of 5:1. Therefore its calculation is performed using the following expression:

$$ng \text{ vector} = \frac{ng \text{ insert} \cdot bp \text{ vector}}{5 \cdot bp \text{ insert}}$$

Once the reaction mixture was prepared, it was incubated at 16° C. for 16 hrs. The LACK gene was cloned into the Xba I and EcoR I targets (hence having eliminated the target for Mlu I, located between the two in the pCIneo plasmid MCS.

Preparation of Electrocompetent Bacteria and Transformation by Electroporation

For the preparation of electrocompetent bacteria start from a plate preculture of a colony of E. coli DH5a in 20 ml of LB at 37° C. kept under stirring overnight (150 rpm). It is scaled to a 600 ml culture at 37° C. and allowed to grow to an OD of 0.5-0.7 (at 550 nm). Subsequently, the culture is maintained on ice for 30 minutes and centrifuged for 10 minutes at 4,000 rpm at 4° C. The supernatant is removed and dried well with a capillary. It is subsequently resuspended in 25 ml 1 mM Hepes at pH=7 cold (it can also be resuspended in milliQ water). The wash is repeated two additional times and after the last centrifugation the supernatant is discarded and it is resuspended in a total of 24 ml of 10% glycerol.

In order to perform the transformation by electroporation, a 20 ml aliquot of electrocompetent bacteria was initially mixed at 4° C. with 2 ml (100 ng-200 ng) of DNA and it was taken to a sterile electroporation cuvette with a separation of 1 mm between electrodes (Cell Projects) cooled at 4° C. In order to be able to apply all available DNA in such a small volume, its precipitation was performed previously as it has been described in section 2.1.4. In this manner, preventing surge when the electric pulse is applied would be achieved. A pulse of 1.8 kV was applied for 5.4-5.8 ms in a Micropulser™ (Bio-Rad) electroporator, 1 ml of SOC medium (tryptone peptone 2%, yeast extract 0.5%, 10 mM NaCl, 2.5 mM KCl, 10 mM $MgCl_2$; sterilized in autoclave at 120° C. for 20 min at 1.05 $Kg/cm^2$) was quickly added and incubated at 37° C. for one hour with orbital stirring at 220 rpm. Finally, cells were plated on LB-agar (LB medium with 15 g/l agar; sterilized in autoclave at 120° C. for 20 min at 1.05 $Kg/cm^2$) with 100 mg/ml ampicillin and incubated at 37° C. for 16 hrs. The remaining mixture was stored at −80° C., having previously added sterile 20% glycerol Selection of pCI-bla-fabI-LACK Recombinant Clones With the purpose of selecting clones containing inserts fab I, 20 colonies were randomly picked and propagated in LB liquid culture medium in the presence of ampicillin 100 mg/ml. Next, the corresponding plasmids were purified following the procedure described in 2.1.7. and both aliquots were analysed by agarose gel electrophoresis as described in section 2.1.3. Only those clones which were positive were selected to be sequenced using the primers described in section 2.1.2. Therefore, the presence or absence of the insert fab I was analysed by the Sanger sequencing method. To this end, plasmids and primers were sent to the DNA sequencing service Secugen, at the Biological Research Center. The obtained sequence of pCI-bla-fabI-LACK is provided as SEQ ID NO: 22.

1.2.3. Removal of the bla Gene from pCI-bla-fabI-LACK (SEQ ID NO: 22) Obtaining the Recombinant Vaccine pPAL-LACK (SEQ ID NO: 23)

One of the pCIbla-fabI-LACK recombinant clones was selected, it was propagated in culture and the corresponding recombinant plasmid was purified according to the procedure described in section 1.2.1. In order to remove the bla gene from this construct, it was excluded by PCR using suitable primers, while at the same time the amplification of the fragment of interest in the reaction was performed. The primers used were as follows:

```
(BamH1-pCI-Δbla-1):
                                    SEQ ID NO: 12
5' GTACAGGATCCCATGTGTCAGAGGTTTTCAC 3'

(BamH1-pCI-Δbla-2):
                                    SEQ ID NO: 13
5' GTACAGGATCCGCAGAAGTGGTCCTGCAACTT 3'
```

The PCR amplification reaction was performed as it has been detailed in section 1.2.2., with the following exceptions: the primers and template DNA used are the ones detailed in this section; the hybridization temperature was 58° C. instead of 60° C.; and the extension time was 2' 30" instead of 2'.

Finally, after carrying out the appropriate purification, as described in section 1.2.2. for the vector, the ligation reaction of the linear molecule with itself was carried out, i.e. its recircularization, using the conditions described in section 1.2.2. but with the following differences: only the plasmid molecule to be recircularized is present, with a final concentration of 32 ng/ml in a final reaction volume of 10 µl.

Transformation of Competent Bacteria by Heat Shock

Finally, competent bacteria of the SURE strain of *E. coli* (Agilent Technologies) were transformed by heat shock following the manufacturer's instructions. This strain ensures genetic stability of the construction because it has been genetically modified to be negative to transposition and recombination activities, thus avoiding unwanted rearrangements between plasmid and chromosomal DNA. For this reason it was used to maintain the final construct that forms the recombinant vaccine free of antibiotic resistance genes pPAL-LACK.

After the process was completed, complete sequencing of pPAL-LACK was carried out as described in section 1.2.2. to verify the integrity of all the component elements using, in addition to the primers described above, the following:

```
(pCIseq1):
                                    SEQ ID NO: 14
5' TCAATATTGGCCATTAGCCAT 3'

(106-LACK-pCIseq):
                                    SEQ ID NO: 15
5' CCACGAGATGGCCGTGCCATC 3'

(LACK-Fw):
                                    SEQ ID NO: 16
5' ATGAACTACGAGGGTCACCT 3'

(LACK-Rv):
                                    SEQ ID NO: 17
5' TTACTCGGCGTCGGAGATG 3'

(pCIseq2):
                                    SEQ ID NO: 18
5' GTTAAGGGATTTTGGTCATGA 3'

(pCIseq3):
                                    SEQ ID NO: 19
5' TCATGACCAAAATCCCTTAAC 3'

(XbaI-pCIseq4):
                                    SEQ ID NO: 20
5' TCTAGAGTCGACCCGGGC 3'
```

2. Verification of the LACK Gene Expression in In Vitro Culture of HEK293T Cells HEK 293T cells (ATCC CRL-3216) are cultured until they are semiconfluent (approximately 48 hrs) in a Petri dish at 37° C. in the presence of 5% $CO_2$ in DMEM (Invitrogen) medium supplemented with 10% fetal bovine serum (Lonza) (Heat-inactivated fetal bovine serum (HIFBS) inactivated at 56° C. for 1 hr) and penicillin 100 IU/ml-streptomycin 100 ng/ml, this being the complete medium (CM). The adhered cells are detached by trypsin-versene (Lonza) rapidly inactivating it by adding DMEM medium tempered at 37° C. The cells are centrifuged at 250 g for 10 min, resuspended in CM five times more diluted than at the beginning and plated in 12 well plates in a volume of 1 ml/well, each having a 1 cm radius. They are reincubated and when semi-confluent, they are washed with DMEM medium tempered at 37° C. and then incubated for 5' with a mixture previously prepared as follows: for each of the above wells, 4 ml of JetPei (PolyPlus Transfection) are mixed gently with 46 ml of a sterile 150 mM NaCl solution; on the other hand, 2 mg of the plasmid are mixed, in this case pPAL-LACK and, on the other hand, pCI-neo as negative control and pCI-neo-LACK as positive control, with the same NaCl solution up to a volume of 50 ml (not exceeding 10% of volume of DNA solution with respect to the total); next, the first mixture is added to the second, never the other way around, they are gently mixed and incubated at room temperature for 30'. After carefully adding this mixture to the cells by the wall, and after incubation for 5 min at room temperature, 1 ml of CM is added per well and the cells are incubated in the same way until they reach confluence or are close to it.

To verify that the LACK gene has been expressed, the presence or absence of the protein will be analyzed by Western Blot. For this purpose, first the cells are lysed with a 1% SDS w/v solution in 1×PBS at room temperature for 5 min and electrophoretically separated in discontinuous buffer system in acrylamide gel under denaturing conditions (SDS-PAGE); the concentrating gel is 5% (5% acrylamide-0.14% bisacrylamide, 0.1 M Tris-HCl pH 8.8, 0.1% SDS, 0.036% ammonium persulfate and 2.3 mM NNN'N'-tetramethylethylenediamine (TEMED)) and the separating gel is 10% (10% acrylamide-0.27% bisacrylamide, 376 mM Tris-HCl pH 8.8, 0.1% SDS, 0.034% ammonium persulfate and 5 mM TEMED). The samples were applied to the gel in loading buffer (50 mM Tris-HCl pH 6.8, 100 mM DTT, 2% SDS, 0.1% bromophenol blue) and then, SDS-PAGE was performed in electrophoresis buffer (20 mM Tris-base, 67 mM glycine, 0.1% SDS) at 12 mA for 30 min and then at 120 V at 30 mA for approximately 2 hrs in a MiniProtean® II (BioRad) cell. Electrophoresis was performed in duplicate: i) one gel was stained with Coomassie blue to visualize total protein extracts and ii) the other gel was transferred to a nitrocellulose membrane.

For carrying out the transfer of the proteins from the gel to the membrane (Hybond™-C pure Amersham Life Science), two scourers, two 3M papers (6×9 cm) and one nitrocellulose membrane are immersed in transfer buffer (0.3% Tris-base, 1.44% glycine, 20% methanol). Subsequently they are placed in a holder and in this order: scourer, 3M paper, gel, nitrocellulose membrane, 3M paper and scourer, so that when closing the holder it is placed on the transfer tray towards the black pole (negative pole) thus allowing the transfer of proteins from the gel to the membrane. The holder is placed on the transfer tray with the same buffer in which all the above-mentioned elements have been submerged, carrying out the transfer at 100 volts for 1 hour at 4° C.

Once the transfer of proteins from the gel to the membrane has been carried out, Western blot was performed for verifying the expression of the LACK gene. For this, first the membrane was blocked with 5% skim milk in PBS-Tween for 1 hour stirring at room temperature. Subsequently, 3 washes with PBS-Tween were carried out, one fast, one of 15' and one of 5'. Incubation with the primary antibody (Anti LACK) was immediately performed at a 1:1000 dilution in PBS-Tween for 1 hour stirring at room temperature. Subsequently, 2 washes were carried out in the same way already discussed and incubation with the secondary antibody (peroxidase-labeled goat anti-rabbit) was carried out at a 1:2000 dilution in PBS-Tween. Subsequently the same washes were carried out and the membrane was revealed for analysis of the presence or absence of expression of the LACK protein.

3. Assessment of the Protection Levels of pPAL-LACK Against Experimental Infection with *Leishmania infantum*

3.1. Experimentation Animals

A total of 18 Beagle dogs formed part of the study, housed in the Faculty of Veterinary Medicine, University of Zaragoza. The maintenance of animal welfare and health of the same was guaranteed by qualified veterinarians according to the current Spanish legislation (RD1201/05). Clinical observation procedures were carried out by qualified veterinarians according to RD1201/05. Housing, handling and feeding of animals took place according to the ethological requirements of the animal used in the research. Handling procedures and frequency of sampling were designed to minimize stress and health risks of individuals, according to European legislation (86/609) and Spanish legislation (R.D. 223/1988. R.D. 1021/2005) and current guidelines for the ethical use of animals in research.

The absence of antibodies to *Leishmania* was confirmed by indirect immunofluorescence assays (IFI) and all of them were wormed and received routine vaccines against leptospirosis, distemper, adenovirosis-2, hepatitis, parainfluenza and parvovirus.

3.2. Infectious Inoculum Preparation and Experimental Infection 3.2.1. Infectious Inoculum Preparation Origin of the Infectious Material A polysymptomatic dog, naturally infected and who has not received any treatment will be used. Once euthanized, following the standards of the ethics committee for animal experimentation, we will proceed to remove the spleen, popliteal lymph nodes, femur and several ribs.

Preparation of Culture Media

Two types of culture medium were used:
  Biphasic medium NNN (rabbit blood agar), according to the traditional method
  Liquid medium RPMI 1640 (with L-glutamine and Na $HCO_3$-SIGMA®), supplemented with 10% (v/v) of fetal bovine serum (FBS) and 2% of hemin (SIGMA®)

Both media were added penicillin/streptomycin antibiotic solution (100 IU/ml and 100 mcg/ml, respectively).

Strain Isolation

From the infectious material (spleen, lymph nodes and bone marrow), platings were made in NNN medium and they were incubated at 26-27° C. They were monitored every 24 hours to verify the growth of promastigotes. When optimal growth (fine-elongated promastigotes) was observed, they were grown again in RPMI 1640 medium (described above). When the sufficient and necessary amount of metacyclic promastigotes was obtained, they were washed 3 times in Sterile Saline (SS) and counted to establish a $10^8$ promastigotes/ml solution.

3.2.2. Experimental Infection

Each dog was intravenously inoculated with 1 ml of this suspension.

Experimental infection of all animals in the study, except the negative control, was carried out with $10^8$ promastigotes of *Leishmania infantum*. The vaccination protocol followed is reflected in Table 1.

TABLE 1

Vaccination protocol, and experimental infection.

| | DOG No | pPAL-LACK Day −60/−45 | pClneo-LACK Day −60 | MVA-LACK Day −45 | INFECTION Day 0 |
|---|---|---|---|---|---|
| G1 | 1 | + | − | − | $10^8$ promastigotes |
|    | 2 | + | − | − | $10^8$ promastigotes |
|    | 3 | + | − | − | $10^8$ promastigotes |
|    | 4 | + | − | − | $10^8$ promastigotes |
|    | 5 | + | − | − | $10^8$ promastigotes |
| G2 | 6 | − | + | + | $10^8$ promastigotes |
|    | 7 | − | + | + | $10^8$ promastigotes |
|    | 8 | − | + | + | $10^8$ promastigotes |
|    | 9 | − | + | + | $10^8$ promastigotes |
|    | 10 | − | + | + | $10^8$ promastigotes |
| G3 | 11 | − | − | − | − |
|    | 12 | − | − | − | − |
|    | 13 | − | − | − | − |
| G4 | 14 | − | − | − | $10^8$ promastigotes |
|    | 15 | − | − | − | $10^8$ promastigotes |
|    | 16 | − | − | − | $10^8$ promastigotes |
|    | 17 | − | − | − | $10^8$ promastigotes |
|    | 18 | − | − | − | $10^8$ promastigotes | pfu: plaque forming units;
G1 pPAL-LACK 200 mcg;
G2 pClneo-LACK 100 µg/ml + MVA-LACK ($10^8$);
G3 NEGATIVE CONTROL;
G4 POSITIVE CONTROL.

In order to assess the efficacy of the recombinant vaccine p-PAL-LACK, the immune response against the vaccine was evaluated in all animals of the study by assessing various parameters: symptoms during the test (section 3.3 below), parasite load from bone marrow by real time quantitative RT-PCR (qPCR) (section 3.4 below), humoral immunity (section 3.5 below) and cellular immunity (section 3.6 below).

3.3. Assessment of the Symptomatology

Clinical monitoring was performed throughout the experiment, in which the most common symptoms that occur in canine leishmaniasis were assessed using a system of "numerical evaluation of symptoms" (NES). Notably, the following symptoms were assessed to determine the degree of "leishmaniasis compatible symptomatology". This term as used herein refers to a compendium of symptoms that are characteristic but not exclusive of leishmaniasis:

conjunctivitis and other eye injuries,
presence of skin lesions: ulcers, desquamation, alopecia, depigmentation etc.

presence of lymphadenopathies,
pale mucous membranes,
onychogryphosis (bowing and abnormal nail growth),
muscle atrophy,
weight loss,
splenomegaly (enlarged spleen),
hepatomegaly (enlarged liver).

Said system of "numerical evaluation of symptoms" (NES) was used with the purpose of quantitating both the number of symptoms shown by each animal and the intensity at which these symptoms occurred. In the presence of a clinical sign a value between 1 and 3 was assigned depending on the intensity with which said sign or symptom was expressed, or 0 in case of absence of the same. Thus, NES was the name for the sum of the values assigned to the symptoms analysed.

3.4. Determination of Parasite Load from Bone Marrow by Real Time Quantitative RT-PCR (qPCR)

The parasite load in bone marrow was evaluated by real time quantitative RT-PCR in all the animals of the study throughout the experiment. For this purpose a bone marrow sample was extracted and it was collected in tubes containing EDTA for sample preservation and were kept at 4° C. until further processing.

3.4.1. Extraction of Genomic DNA from Bone Marrow: NucleoSpin 96 Tissue Kit (Macherey-Nagel/Cultek)
i. 20 mg of tissue were prepared in rounded wells plates, Round-well Block.
ii. A 25 µl proteinase K solution (provided in the kit) with 180 of Buffer T1 per sample was prepared and 200 µl of this mixture dispensed in the block of step i.
iii. The block was closed with cap strips and shaked vigorously for 10-15 sec.
iv. The block containing the samples was incubated at 56° C. for 10 min or until noticing that the samples were lysed properly and mixed regularly during this step. A weight was placed on the lid to prevent it from opening due to gas pressure.
v. If necessary, solid residues were removed by centrifugation for 2 min at 5,600 g and then the supernatant transferred to a new block, Round-well Block.
vi. From here, steps iii to xi of procedure 1.1. were carried out, with the following differences:
A NucleoSpin Tissue Binding Plate was used.
One wash was performed with Buffer BW and another one with Buffer B5.
Elution was carried out in 100 µl of Buffer BE preheated at 70° C. by incubating for 1 min at room temperature and centrifuging for 2 min at 5,600 g.

3.4.2. Preparation of the Internal and External Standards
i. *L. infantum* promastigotes were cultured in RPMI medium supplemented with 10% inactivated fetal bovine serum and 100 µg/ml streptomycin-100 IU/ml penicillin.
ii. Once they reached the stationary phase, they were centrifuged at 2,000 g for 10 min, washed three times with PBS and resuspended in PBS.
iii. DNA was purified using the NucleoSpin Blood kit in separate tubes. To do this, 200 µl of pellet resuspended in PBS (step ii) were used and section 1.1. steps were followed, although in separate tubes. The extraction was started using different amounts including a control without sample to subsequently determine the yield.
iv. Known amounts of *L. infantum* genomic DNA were added to dog DNA samples PCR-negative to *Leishmania* sp., so that the amount per standard was finally 10-20 ng in 2 µl.

3.4.3. Quantification of Genomic DNA
Quantification was performed with Qubit, Qubit DNA BR assay kit (Life Technologies). All the components except Qubit DNA BR Buffer ("Component B") were preserved at 4° C.
i. The number of samples were calculated including both standard solutions and one excess.
ii. 199 volumes of "Component B" (Qubit DNA BR Buffer) with 1 volume of reagent "Component A" (Qubit DNA BR Reagent) were mixed.
iii. 180-199 mcl of this mixture was added per tube, depending on the volume of sample measured (between 1 and 20 µl), such that the final volume is 200 µl.
iv. 10 mcl of each standard were added to 190 µl of the previous mixture into the corresponding tubes. In this case, there were two standards: "Component C" (Qubit DNA BR Standard #1), which is the blank, and "Component D" (Qubit DNA BR Standard #2), which has an ssDNA concentration of 20 ng/µl.
v. An adequate volume of sample (1-20 µl) was added.
vi. Mixing by vortexing and a pulse spin in the centrifuge were performed.
vii. The tubes were incubated for 2 min at room temperature.
viii. On the Qubit main screen, "DNA" was selected and then "dsDNA" as type of test. Then the screen showed "Standards".
ix. "Run a new calibration" was selected.
x. The tube containing the Standard #1 was inserted in the slot and "Read" button was pressed. Next, said tube was removed and the operation with the Standard #2 repeated. The calibration result was displayed on the screen.
xi. The above operation was repeated for all samples pressing "Read Next Sample".
xii. The concentration of the sample was calculated as follows:

$$\text{Concentration of sample} = Q \cdot (200/x),$$

wherein Q is the value provided by the Qubit and x the volume of sample that was added to the tube. This concentration value was calculated by the unit by pressing "Calculate Stock Conc." and selecting the volume of sample that had been added in the wheel on the center of the screen.

3.4.4. Real Time Quantitative RT-PCR by the Method of TaqMan Probes
Note: all the mixtures were prepared and reagents kept on ice during the process. The container was decontaminated of DNA and nuclease.
i. In the area of sample handling, 1/5 serial dilutions of genomic DNA were prepared starting from a solution at a concentration of 5-10 ng/µl.
ii. In the clean area for storage and handling of the reagents, the master reaction mix (master mix) was prepared for all the reactions that had to be performed including dilutions and biological and technical replicates plus a suitable remnant according to pipetting losses. Each reaction mix had a final volume of 10 µl and consisted of the following components, excluding the sample:

| | |
|---|---|
| TaqMan Fast Universal PCR Master Mix (2X) | 5.00 µl (1X) |
| Leish-1 and Leish-2 Primers (100 µM each) | 0.09 µl (900 nM each) |
| Leish-P Probe (100 µM) | 0.09 µl (200 nM) |
| Nuclease-free water (Life Technologies) | 2.82 µl |

The primer and probe sequences were:

(Leish-1)
SEQ ID NO: 25
5'AACTTTTCTGGTCCTCCGGGTAG3'

(Leish-2)
SEQ ID NO: 26
5'ACCCCCAGTTTCCCGCC3'

(Leish-P)
SEQ ID NO: 27
5'-6-FAM-AAAAATGGGTGCAGAAAT3' iii. Using the multichannel pipette, 8 μl of master mix per well were added in a 384 well plate, which was prepared in the clean area for storage and handling of reagents.
iv. The plate was moved to the area of sample preparation and 2 μl of sample were added per well.
v. The qPCR reactions were run in a 7900HT Fast Real Time PCR system using the SDS 4.1. software (Life Technologies) following the procedure specified by the manufacturer. The thermal cycling conditions were: 95° C. for 5 min; 40×[95° C. for 30"; 60° C. for 1 min, data acquisition].

3.4.5. Analysis

Note: the whole process was performed with Microsoft Excel. There was a template available to do this, so the Ct values and, once the linear regression had been carried out, the value of the slope of the line was entered in the corresponding boxes, so that once this was done the results were automatically obtained.

i. Calculation of the arithmetic means of the replicates made from each dilution, the quasi-standard deviation or uncertainty (standard deviation, SD) and the coefficient of variation (CV).

$$CV (\%) = (SD_{dilution}/Ct_{dilution\ medium}) \times 100$$

ii. Elimination of the points whose CV is greater than 20% (they were considered as outliers).
iii. Calculation of the amplification efficiency independently for each biological sample and for each triad of primers and probe from the data of the corresponding technical replicates and serial dilutions. The Ct value versus log of the total template mass added to the reaction mixture (μg) was represented and linear regression performed. The value of the regression coefficient ($r^2$) should be as close as possible to 1. The efficiency was be determined by the value of the slope of the line.

Note: the same process with internal and external standards was performed.

iv. Calculation of the efficiency.

$$\text{Efficiency} = 10^{(-1/slope)}$$

v. Calculation of the amount corrected with the efficiency for each of the values.

$$\text{Amount} = \text{Efficiency}^{-Ct}$$

vi. Calculation of the mean and SD of the amount for the technical replicates of a given dilution and condition.
vii. Normalization (by condition and dilution). An amount of 18S rDNA (Eukaryotic 18S rRNA pre-developed TaqMan assay reagent, Life Technologies) was considered.
  a. The amount values for minicircles (mc) were divided by those of the reference gene ("GOR": gene of reference, such as IFNgamma or IL-10).
  b. Calculation of the $SD_{normalized\ amount}$:

$$SD_{normalized\ amount} = \text{Normalized amount} \cdot [(SD_{mc}/\text{Amount}_{mc})^2 + (SD_{GOR}/\text{Amount}_{GOR})^2]^{1/2}$$

viii. Calculation of the number of amastigotes/mg tissue by external and internal standard.
Note: the yield calculated in DNA extraction was applied.
ix. Calculation of the mean of the number of amastigotes/mg tissue obtained with different dilutions and the corresponding SD (calculation of SD of the means).

3.5. Evaluation of Humoral Immunity

Determination of the relative levels of total IgG, IgG1 and IgG2 by enzyme-linked immunoassay (ELISA) technique from blood from all the animals in the study and throughout the experiment. For this purpose, the serum was extracted from all the collected samples and kept at −20° C. until carrying out the ELISA in 96 well plates.

The determination of the relative levels of total IgG, IgG1 and IgG2 was carried out by enzyme-linked immunoassay (ELISA) technique.

3.5.1. Preparation of the Samples

The samples were transported from Zaragoza to Madrid at −20° C. with cold packs inside an expanded polystyrene box. A freezing box was used to organize and store samples and to reduce the risk of contamination.

i. The area of sample extraction was cleaned with ethanol.
ii. The extraction of the 2 ml blood sample was performed using a sterile 21 G needle and a 5 ml syringe.
iii. Immediately, the sample was brought to the sample processing table of the sampling room, the needle removed and the contents of the syringe poured in a serum separation tube (EUROTUBE, Deltalab).
iv. The blood sample was mixed with the granules by gentle inversion 5 times.
v. Samples remained at room temperature for 25-35 minutes for blood to clot properly (in our case, namely 30 min after the last extraction prior to centrifugation).
vi. Centrifugation at a maximum of 1,000 g (1,500 g is the maximum specified by the manufacturer) for 10 min at 24-26° C. as a minimum.
vii. The serum was collected and transferred to a 1.5 ml sterile tube. The tubes were placed in a freezing box.
viii. Samples were shipped within a freezing box from Zaragoza to Madrid at −20° C. inside a polystyrene box with ice packs.
ix. The next day, the sera were stored in a freezer at −20° C. for preservation.
x. The day before use, the sera were thawed and suitable aliquots removed. The corresponding dilutions of the different sera were arranged in 96 well plates. In this manner, the necessary amounts of sample were transferred to ELISA plates with multichannel pipettes in the corresponding step.

3.5.2. Preparation of the Soluble *Leishmania* Antigen (SLA)

i. A culture of *L. infantum* promastigotes was performed in RPMI medium supplemented with 10% inactivated fetal bovine serum and 100 μg/ml streptomycin-100 IU/ml penicillin. For example: 100 ml culture with 2×10$^6$ initial promastigotes.
ii. Once they reached the stationary phase, they were centrifuged at 2,000 g for 10 min and washed three times with PBS. Finally, they were resuspended in PBS.
iii. Three cycles of freezing and thawing (−20° C.—room temperature) were performed without accelerating freezing or thawing.
Note: this would be the CLA, which would be quantified directly by the Bradford method.
iv. Sonication was performed keeping the tube on ice (three cycles).
v. A centrifugation step at 16,000 g was performed for 3 min.

vi. The supernatant (SLA) was recovered and quantified by the Bradford method (see note in step iii).

3.5.3. ELISA for Detection and Relative Quantification of Total IgG, IgG1 and IgG2.

The experiment was performed in duplicate according to the following instructions:

i. Preparation of Solutions:
  i.1. SLA Working solution: 200 μg/ml.
  i.2. Carbonate-bicarbonate buffer. For 100 ml, 840 mg $NaHCO_3$ and 356 mg $Na_2CO_3$, pH 9.6.
  i.3. Blocking solution: 1% BSA in PBS.
  i.4. Washing solution: 0.1% BSA, 0.03% Tween-20 in PBS.
  i.5. Antibodies and protein A. Prepare dilution at the time of use.
  Dilution 1:15,000 in blocking solution for goat anti-Dog IgG1-HRP (Bethyl laboratories), 1:20,000 in blocking solution for sheep anti-Dog IgG2-HRP (Bethyl laboratories) and 1:8,000 (0.19 μg/ml) in washing solution for HRP-rec protein A (Life Technologies).
  i.6. Citrate buffer. 1 g of citric acid and 1.8 g of disodium phosphate ($Na_2HPO_4$) pH 5 in 100 ml.
  i.7. OPD Substrates (Invitrogen-Zymed) and $H_2O_2$. Prepare at the time of use. Dissolve 1 tablet of OPD in 12 ml of citrate buffer and add 15 μl $H_2O_2$ (35%).
ii. Plate wells were coated adding 100 μl SLA 10 μg/ml in carbonate-bicarbonate buffer pH 9.6 to each of them (100 ml SLA 10 μg/ml are prepared by adding 95 ml of the buffer to 5 ml of SLA 200 μg/ml).
iii. The plate was covered with parafilm and incubated overnight at 4° C.
iv. Then, the contents of the wells were discarded by inverting the plate with a vigorous movement and dried hitting on filter paper. This step was performed after each incubation until step x inclusive.
v. 200 μl/well of blocking solution were added and a 1 hr incubation step at room temperature was performed.
vi. 3 washes with 200 μl/well of washing solution were carried out.
vii. 100 μl of each sample were then added to the corresponding well by using the multichannel pipette (see 1.x.) and incubated for 30 min at room temperature.
viii. 3 washes with 200 μl/well of washing solution were performed.
ix. The primary antibodies were added at the suitable dilution to the corresponding wells (see i.5), which were then incubated for 2 hrs at room temperature.
x. Two washes with 200 μl/well of washing solution and one with the same volume of PBS were carried out.
xi. 100 μl/well of OPD and $H_2O_2$ (see i.7) substrates were added and the plates covered with foil and incubated in the dark for 20-30 min at room temperature.
xii. The reaction was stopped with 50 μl/well of 1% SDS.
xiii. Absorbance at 450 nm was read. For this purpose, the plate reader Microplate Reader Model 680 (BioRad) and the Microplate Manager 5.2.1. (BioRad) software were used and the data exported to a Microsoft Excel file clicking on File, Export to Excel.
xiv. An indirect ELISA assay of all experimental groups was performed for each time of the experiment following the procedure specified above, and the calculations detailed below. The individual values for each animal were represented on a time histogram and the mean values of the groups in a graph of optical density at 450 nm over time, so that, in the latter case the graph was completed as the experiment progressed.

i. The mean value of the blanks were substracted corresponding to each of the data.
ii. The arithmetic mean and the uncertainty (SD) of each sample (duplicates in different plate) were calculated.
iii. The corresponding time histogram was depicted.
iv. The arithmetic mean and the uncertainty (SD) within each group were calculated.
iv. The point on the graph of optical density at 450 nm ($OD_{450\ nm}$) over time (days) was depicted.

3.6. Evaluation of Cellular Immunity

The evaluation of cellular immunity against the LACK antigen was carried out at two levels. On the one hand the rate of proliferation was determined in peripheral blood mononuclear cells against different stimuli, total *Leishmania* antigen (CLA) and LACK protein. After five days of incubation, cell labeling with the $CD4^+$ and $CD8^+$ antibodies was performed, and they were analyzed by flow cytometry. On the other hand the level of IFN-γ and IL-10 cytokines was determined in supernatants from in vitro proliferation, mentioned above.

3.6.1. Lymphoblastic Transformation Test (LTT) or Lymphoproliferation in Peripheral Blood Mononuclear Cells (PBMC)

i. Extraction of 8 ml of blood in heparin-Li tubes under sterile conditions. Transport at room temperature. Storage overnight at room temperature.
ii. PBMC isolation by Ficoll gradient.
  a. 8 ml of blood were decanted in a tube containing 10 ml of PBS-EDTA in a 50 ml polypropylene tube.
  b. The diluted sample was deposited on 7 ml of Ficoll (Lymphoprep) very slowly with the 50 ml polypropylene tube in horizontal position and substantially perpendicular to the pipette.
  c. The gradient was centrifuged at 2,000 rpm in the Beckman centrifuge for 30 min at room temperature. The ring (buffy coat) was collected and taken to another equal tube.
iii. Wash and lysis of erythrocytes. One wash was performed with 50 ml of PBS-EDTA by centrifugation for 5 min at 2,000 rpm in the Beckman centrifuge. Cells were resuspended in 1 ml of erythrocyte lysis buffer, which was allowed to act for 10 min at room temperature, and all the volume brought to 1.5 ml to new sterile eppendorf tubes. The cells were harvested by centrifugation in the eppendorf 5415R or 5424R microcentrifuge at 2,500 g for 30 sec. at 25° C. and when the lysis was complete, the white pellet and the red supernatant was observed. If lysis was not complete, it was repeated. Two aliquots from two different samples were removed for the CFSE labeling negative controls (approximately 20% of samples having many cells). Samples were centrifuged at 2,500 g for 30 sec. at 25° C. in the Eppendorf 5415R or 5424R microcentrifuge.
iv. Labeling with CFSE (CellTrace™ CFSE Cell Proliferation Kit, for flow cytometry, Thermo Fisher Scientific) the pellet was resuspended in 100 μl of 2.5-10 μg/ml CFSE (3.75-15 μl of 1 mg/ml stock plus 1496.25-1485 μl of PBS). Incubation in the dark at room temperature for 20 min was carried out.
v. Two aliquots were removed from two different samples for the CFSE labeling positive controls (approximately 20% of samples having many cells).
vi. Two washes with 1 ml of washing medium were performed (supernatants were removed with sterile micropipette filter tips).
vii. Cells were resuspended in 200 μl of proliferation medium with the corresponding stimuli (in the case of the labeling negative and positive controls with CFSE, in 50 μl). 50 μl (¼ of each sample, to distribute between control without stimulus and three stimuli) were added to each 1 ml well of medium with stimulus and incubated at 37° C. under 5% $CO_2$ atmosphere for 3 days.

Note: cells were resuspended in 50 μl of medium without stimulus for each well of each sample to be organized and distributed 24 well plates to which 950 μl of medium with the corresponding stimulus has been previously added.

Stimuli Concentrations:

|  | Final conc. | Stock conc. |
|---|---|---|
| ConA (Concanavalin A, Sigma) | 1 μg/ml | 1 mg/ml |
| CLA | 10 μg/ml | 1 mg/ml |
| LACK | 5 μg/ml | 0.1-1 mg/ml |
| Neg. ctrl. (medium) | — | — |

3.6.2. Labeling Protocol for Cytometry

The whole procedure was performed with the plates on ice and the centrifuges refrigerated at 4° C.

i. The entire volume of the 24 well plates was transferred to deep-well 96 well plates (Eppendorf), so that four wells from the same column were used for the sample of each dog (one per each stimulus).
ii. Centrifugation at 2,300 rpm for 5 min at 4° C. in the Beckman centrifuge.
iii. The supernatants were stored in new deep-well plates and preserved at −20° C. for detecting the level of the aforementioned cytokines by ELISA.
iv. The deep-well plates containing the pellets were stirred with vortex and each one resuspended in 200 μl of PBS-1% BSA (in 300 ml in the CFSE+ and CFSE− controls).
v. The cells were passed to 96 well V-bottom plates by adding 100 μl per well, such that two wells of the 96 well plates corresponded to each stimulus for each sample (one for labeling with anti-CD4 and another one with anti-CD8). Therefore, we had 8 wells per dog. Three wells instead of two are used for the CFSE+ and CFSE− controls, as the first would be without antibody, the second with rat anti-dog CD4-RPE (Serotec) and the third with rat anti-dog CD8-RPE (Serotec). All the controls were made in duplicate.
vi. Centrifugation at 2,000 rpm for 5 min at 4° C. in the Beckman centrifuge. The supernatant was discarded rapidly and the plate strongly reversed and dried upside down on filter paper.
vii. The pellet was resuspended stirring the plate with vortex and quickly adding 200 μl of PBS-1% BSA with the multichannel pipette.
viii. The washing was repeated (steps 6 and 7), but resuspension was performed in 50 μl of PBS-1% BSA.
ix. Add 50 μl of 1/5 dilution of the corresponding RPE-labeled antibody (rat anti-dog CD4 or rat anti-dog CD8). Each of the two wells per stimulus indicated in step 5 was labeled with one of the antibodies. Thorough mixing was performed with multichannel pipette.
x. An incubation step in the dark was performed at 4° C. (on ice) for 1 hr.
xi. Two washes with 200 μl PBS-1% BSA per well.
xii. After the last centrifugation of the washing steps, samples were resuspended in 200 μl of PBS-0.5% BSA-0.003% sodium azide.
xiii. Analysis by flow cytometry (FC500 Beckman-Coulter, following the manufacturer instructions).

Note: when samples were not analyzed immediately, they were fixed with 1% paraformaldehyde by adding 150 μl per well, incubate for 1 hr at 4° C., centrifuge and resuspending as indicated in step 12. They were finally stored for up to 1 week at 4° C. in the dark once fixed.

3.6.3. Determination of the Level of IFN-γ and IL-10 Cytokines in the Supernatants of In Vitro Proliferations by ELISA i. The capture antibody (DuoSet Canine IL10 (R&D Systems, ref. DY735) or DuoSet Canine IFNg (R&D Systems, ref. DY781B)) was diluted to the working concentration of 2 μg/ml in PBS.
ii. 100 μl of diluted capture antibody were added to each well.
iii. An incubation step was performed at room temperature overnight.
iv. Contents were discarded.
v. Three washes with 400 μl of wash buffer (0.05% Tween 20 in PBS pH 7.2-7.4) were performed and the liquid removed well between washings.
vi. Blocking was performed by adding 300 μl of reagent diluent (1% BSA in PBS pH 7.2-7.4) and incubating (step vii).
vii. Incubation step: at least 1 h at room temperature.
viii. Washings were repeated as in point 5.
ix. Add 100 mcl of the sample at the suitable dilution or the standard, with which at least 7 1:2 serial dilutions are performed, the maximum being 2000 μg/ml.
x. Cover the plate and incubate at room temperature.
xi. Washings were repeated as inpoint 5.
xii. 100 μl of detection antibody (biotinylated mouse anti-canine IL-10) were added to the working concentration (20 ng/ml).
xiii. Incubation for 2 hrs at room temperature.
xiv. Washings were repeated as in point 5.
xv. 100 μl of streptavidin-HRP were added.
xvi. A 20 min incubation step was performed at room temperature preventing incidence of light.
xvii. Washings were repeated as in point 5.
xviii. 100 μl of substrate solution (OPD) were added.
xix. Incubation was performed at room temperature for 20 min preventing incidence of light.
xx. 50 μl of stop solution (1% SDS) were added and to samples, which were then mixed well.
xxi. Absorbance was read at 450 nm.

Figure 4:
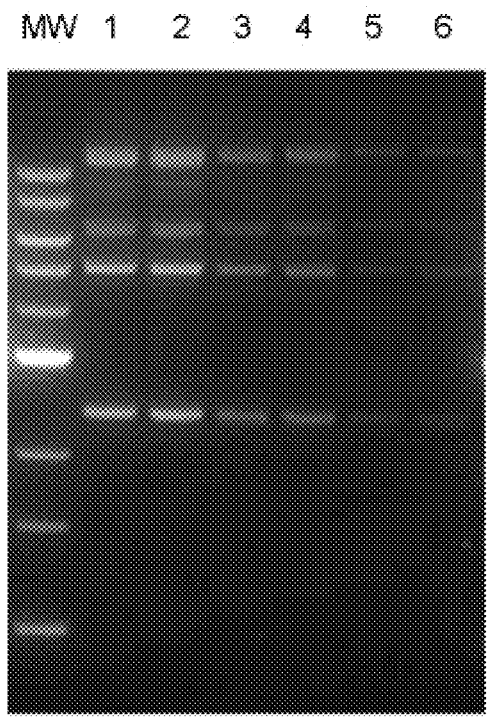
FIG. 4. A) Visualization of the construct pPAL-LACK in 1% agarose gel; MW 1 Kb 125 ng. pPAL-LACK 1 (318 ng/mcl) lanes 1 and 2 (1/6 dilution); lanes 3 and 4 (1/12 dilution) and lanes 5 and 6 (1/24 dilution). B) Expression of the LACK protein gene cloned into the vector pCIneo in cultures of HEK 293T cells transfected for 48 hours. Untransfected cells were used as negative control (MOCK).
Figure 4:
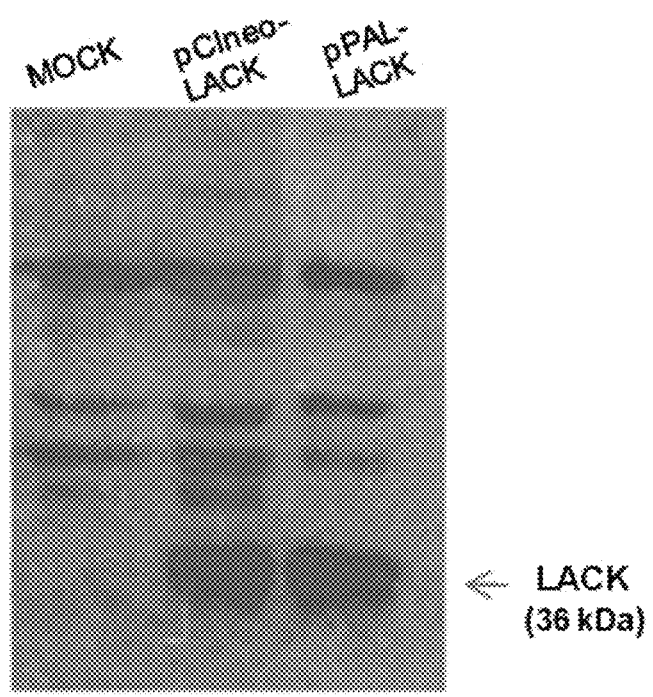

Example 2.—Generation of the pPaI-Lack Vector and Verification of the Lack Gene Expression in In Vitro Culture of HEK293T Cells The pPAL-LACK plasmid was generated as described in Example 1, section 1. A schematic representation of the plasmid is provided in FIG. 2. Furthermore, a photograph of the purified pPAL-LACK construct in 1% agarose gel, is shown in FIG. 4 A).

In vitro expression of the LACK gene in the human cell line HEK293T was carried out as detailed in Example 1, section 2, showing similar expression to that observed in the transfection performed with the plasmid pCIneo-LACK. The band of the LACK protein in an SDS-PAGE gel of HEK 293T cell extracts appears at the expected height of 36 kDa, as shown in FIG. 4B.

Example 3.—Assessment of the Protection Levels of pPaI-LACK Against Experimental Infection with *Leishmania infantum*

I. Assessment of the Symptomatology

Figure 5:
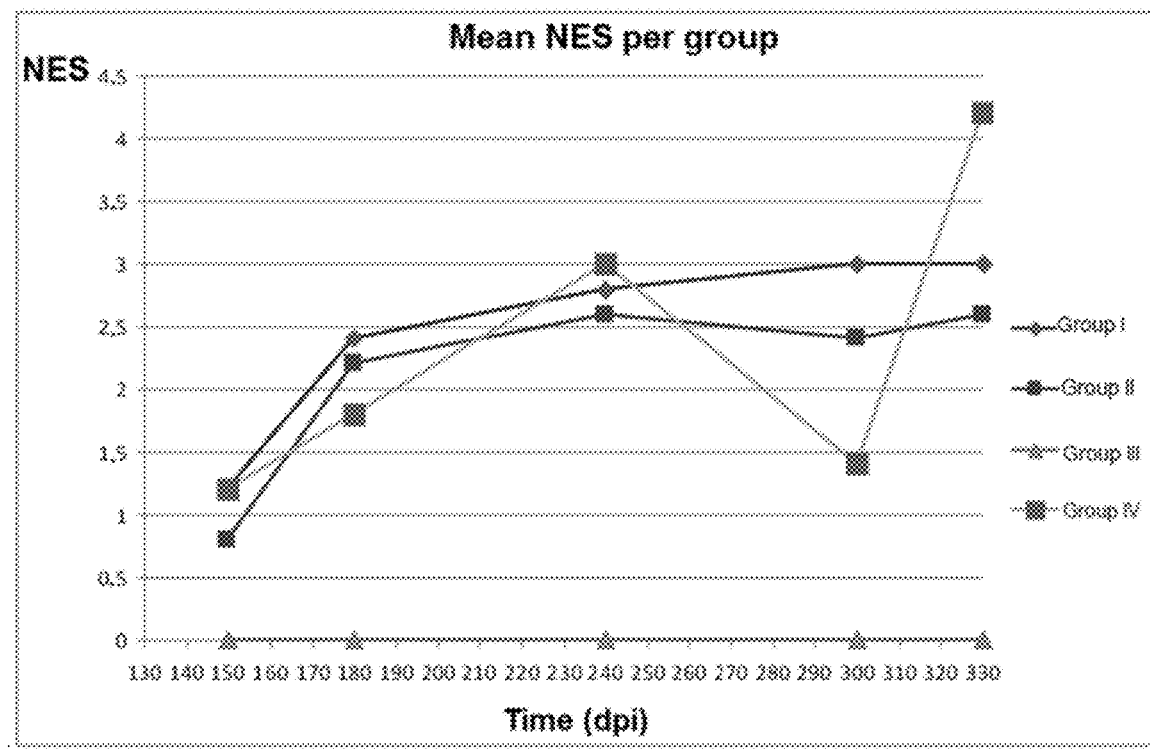
FIG. 5. Graphical representation showing the evolution of symptomatology after infection in experimental groups I to IV, using the "Numerical Evaluation of Symptoms" (NES) system.

As shown in FIG. 5, the vaccinated groups with lower leishmaniasis-compatible symptomatology (see section 3.3.) are I and II. The results observed at the 300 days post infection (dpi) have remained the same until slaughter of animals, since no change has been observed at the end time.

II. Determination of Parasite Load from Bone Marrow by Real Time Quantitative RT-PCR (qPCR)

Figure 6:
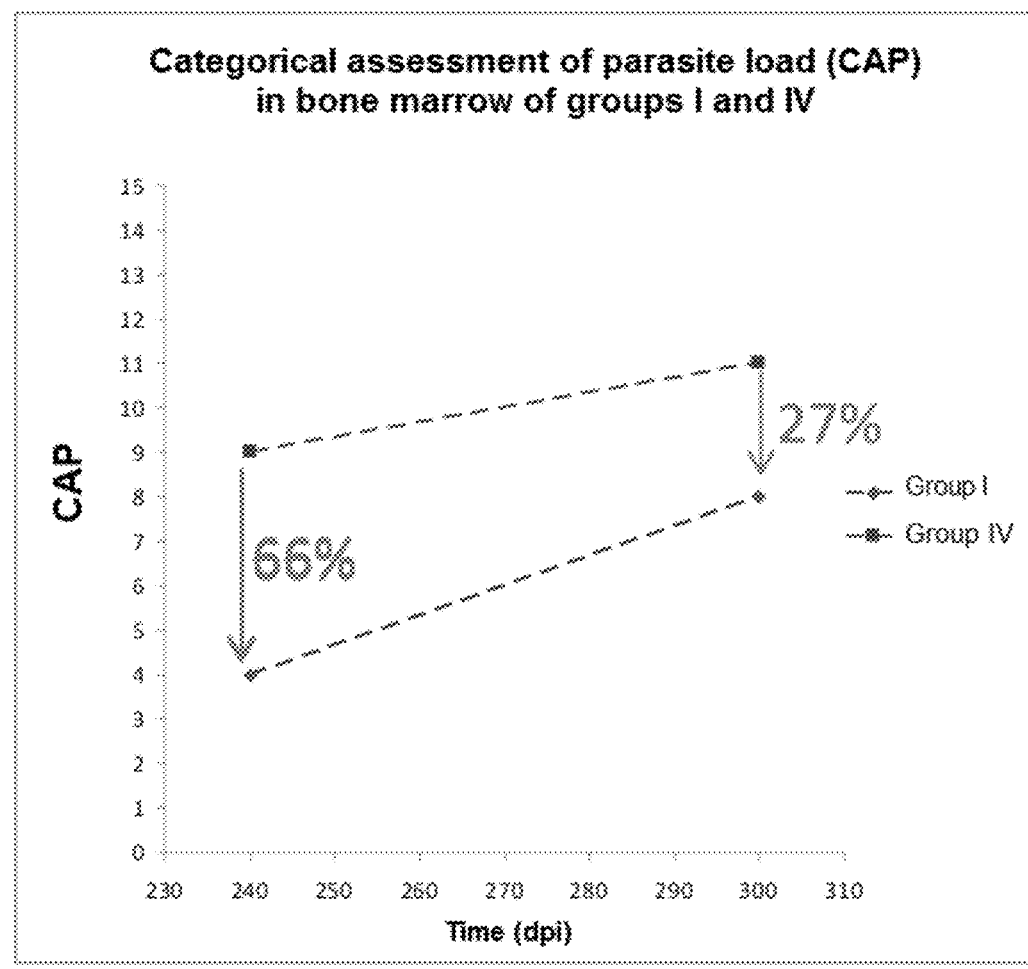
FIG. 6. Categorical assessment of parasite load (CAP) in bone marrow by real time quantitative RT-PCR (qPCR). The arrows show the reduction of parasite load in group I compared to IV.
Figure 7:
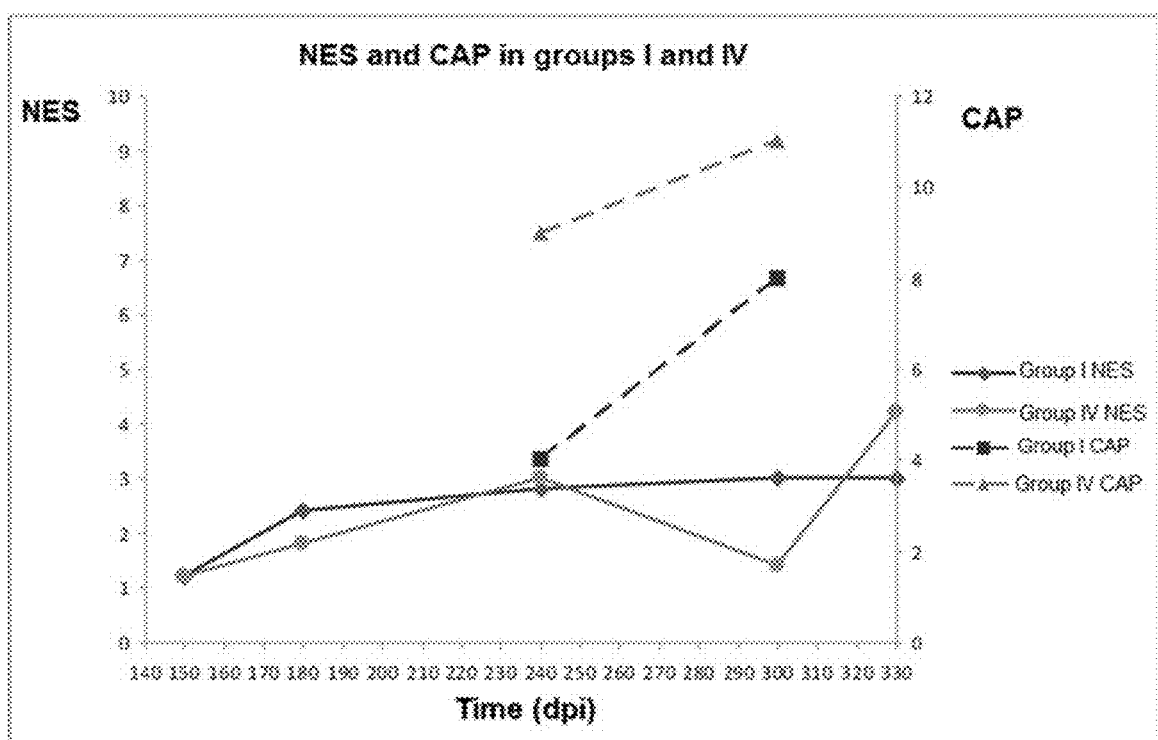
FIG. 7. Relationship between symptomatology and parasite load between groups I and IV.

Bone marrow. Over time, the parasite load has remained at a lower level in group I (FIG. 6). Group II has shown the same trend, except for the time interval around 240 dpi, where there was an increase in group II and a decrease in group IV. FIG. 7 relates symptomatology to parasite load in bone marrow.

The parasite load was also evaluated in blood and target organs as described below:

Blood. The parasite load was evaluated from 240 dpi, being lower in groups I and II.

Target organs. The parasite load was assessed after the necropsies.
 a) Spleen. The best results (lower parasite load) were obtained in group I.
 b) Lymph node. Lower parasite load in group II and then in group I. Group IV is highly parasitized in lymph node.
 c) Liver. Relative profile similar to lymph node, wherein group II has the lowest parasite load when compared to the other groups.

III. Evaluation of Humoral Immunity

Figure 8:
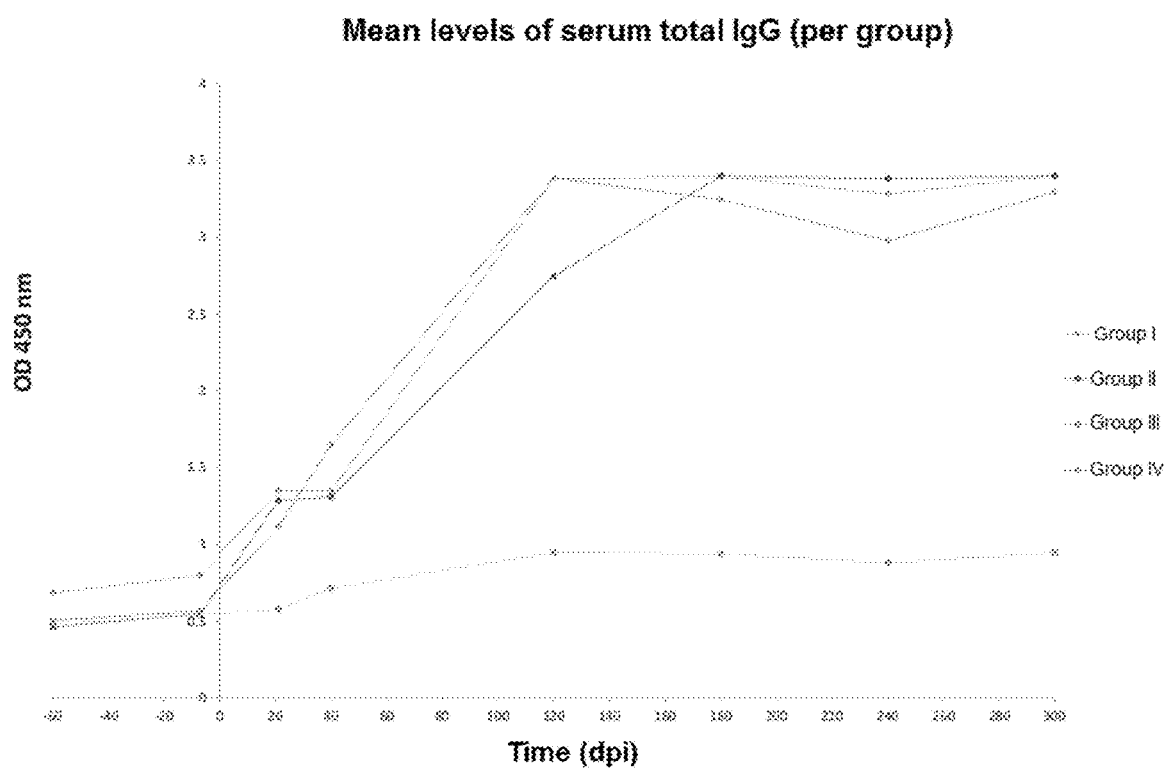
FIG. 8. Evaluation of total IgG levels in serum by ELISA.
Figure 9:
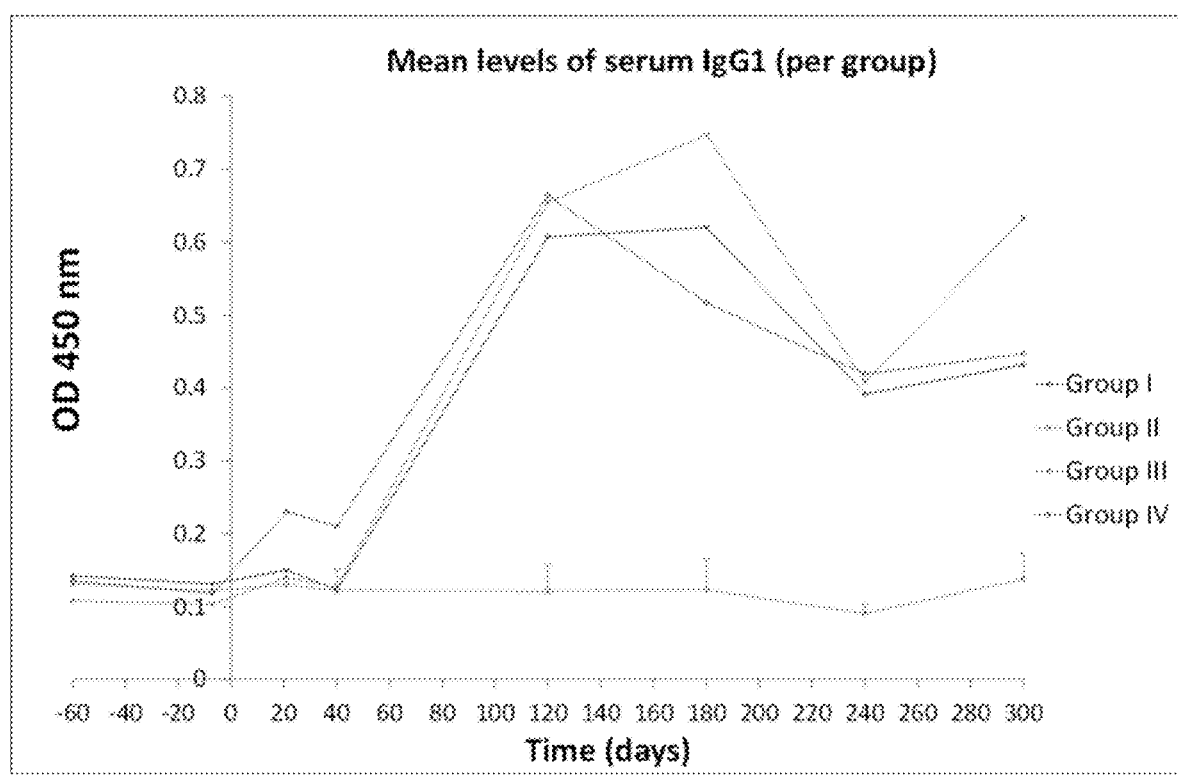
FIG. 9. Evaluation of IgG1 levels in serum by ELISA.
Figure 10:
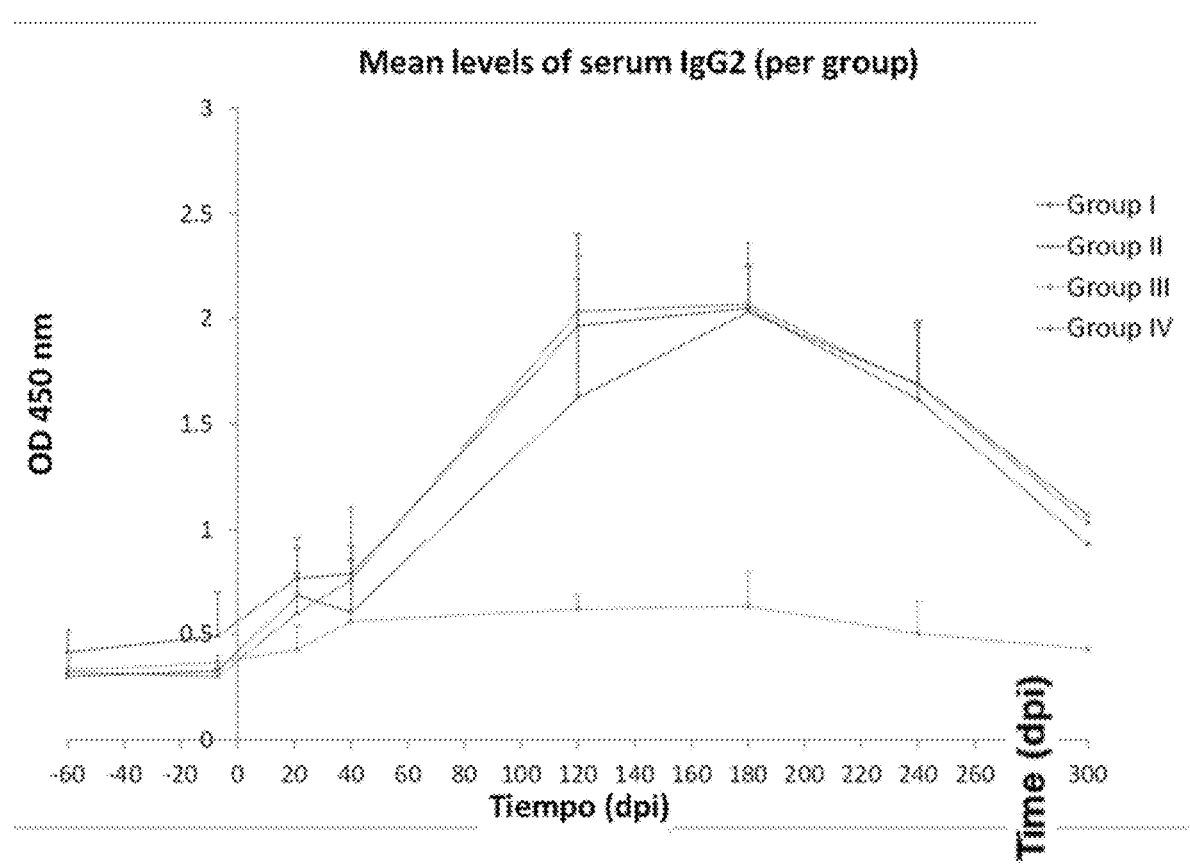
FIG. 10. Evaluation of IgG2 levels in serum by ELISA.

During the immunization period, the levels of total IgG, IgG1 and IgG2 against soluble *Leishmania* antigen (SLA) remained constant at baseline (FIGS. 8-10). The levels of total IgG and IgG2 began to increase in the early infection phase (21 and 40 dpi) in all experimental groups (GI and GII) and positive controls (GIV) and peaked at day 120 (FIGS. 8 and 10). However, IgG1 levels did not increase during the early infection phase and their elevation at 120 dpi was first detected in all groups except in group II, where there was a slight increase in the early infection phase (FIG. 9). Therefore, serology indicates that the experimental infection was carried out successfully in all the experimental groups and the positive control, while in the negative controls (GIII) the production of specific IgG against the parasite was not detected. No significant differences among the groups were detected, except with group III, as expected.

IV. Evaluation of Cellular Immunity

CD4+ T lymphocytes activation levels against CLA and LACK were measured by lymphoproliferation or lymphoblastic transformation assays. Supernatants from PBMC cultures allowed the evaluation of the levels of secreted IFNg and IL10 by ELISA.

Cell Activation.

Figure 11:
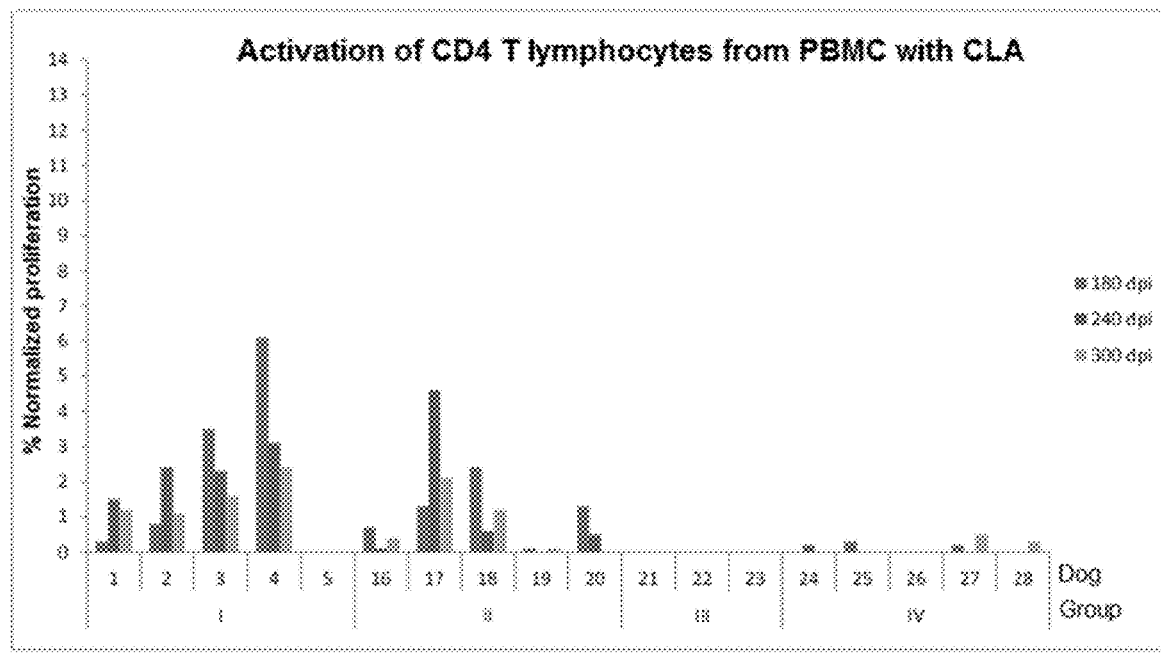
FIG. 11. Evaluation of CD4$^+$ T lymphocytes' activation against total *Leishmania* antigen (CLA) by lymphoblastic transformation test.
Figure 12:
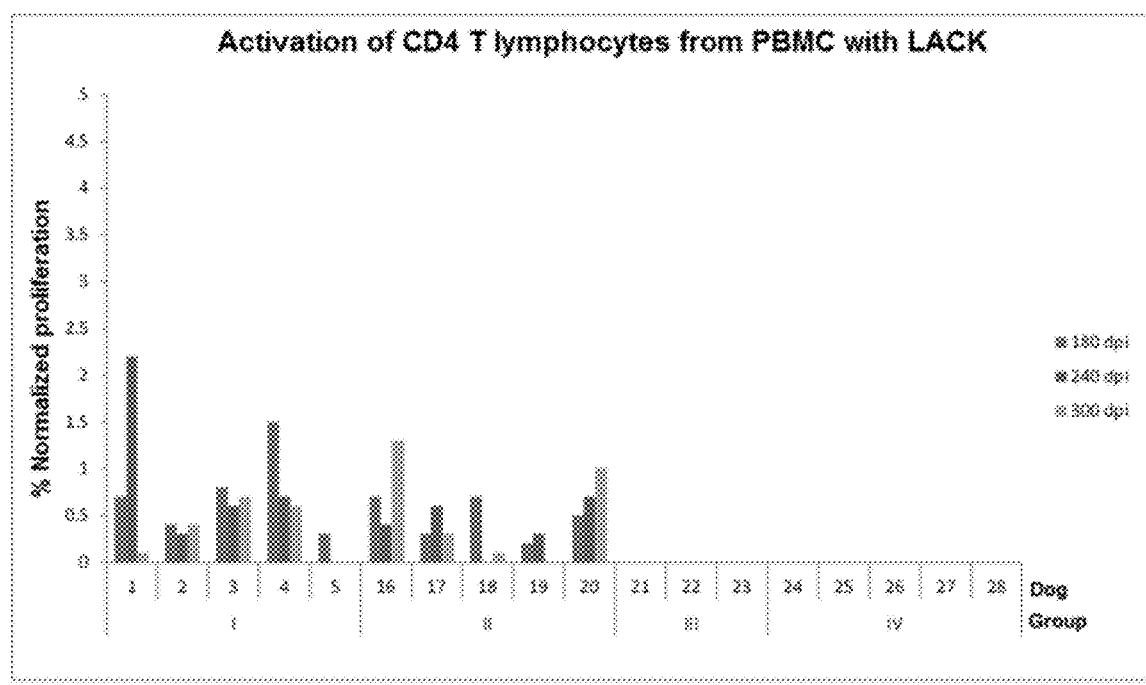
FIG. 12. Evaluation of CD4$^+$ T lymphocytes' activation against LACK antigen by lymphoblastic transformation test.

CD4+ T lymphocytes activation levels in PBMC against CLA and LACK were higher and more uniform in group I over time in general. In group II they were also higher than in group IV (FIGS. 11 and 12).

In target organs, we found:
 a) Spleen. It is found higher in group I, followed by II and IV. As it can be seen in group III, sometimes there is a background of nonspecific cell proliferation.
 b) Lymph node. Activation at similar levels in groups I and II, higher than in the rest.
 c) Liver. Nothing relevant was detected and the results are very irregular. It may be due to the high number of hepatocytes present.

Cytokine Levels in Supernatants of Lymphoproliferation Assays.

Figure 13:
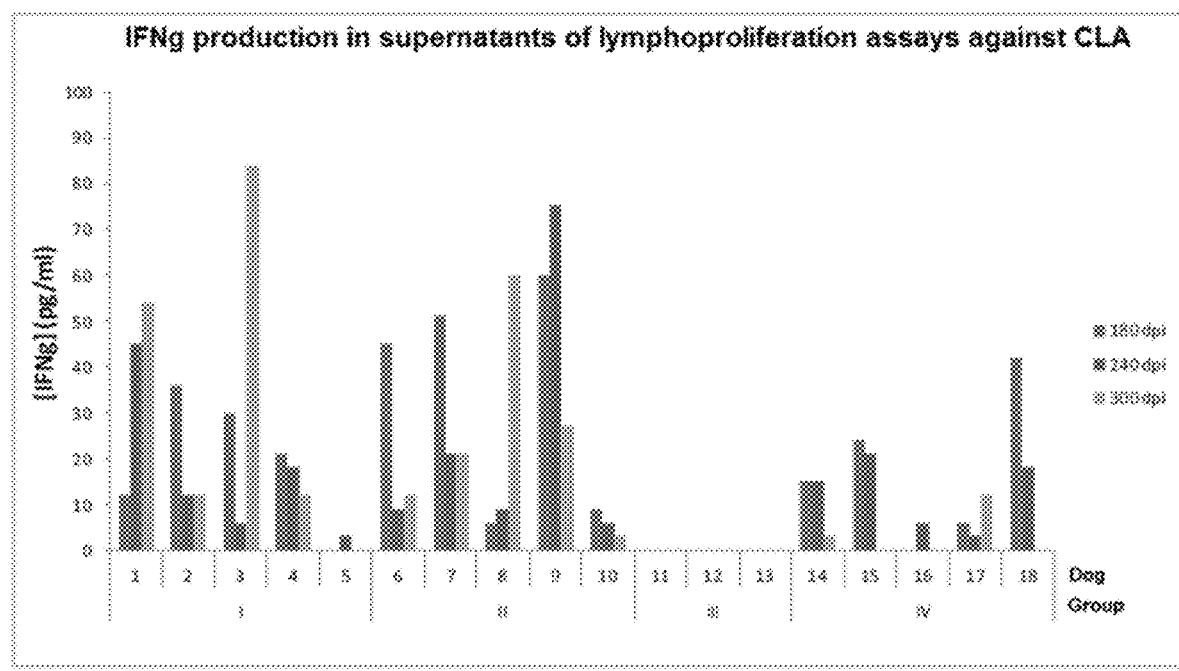
FIG. 13. Evaluation of IFN gamma production against total *Leishmania* antigen (CLA) in supernatants of lymphoproliferation assays by ELISA.
Figure 14:
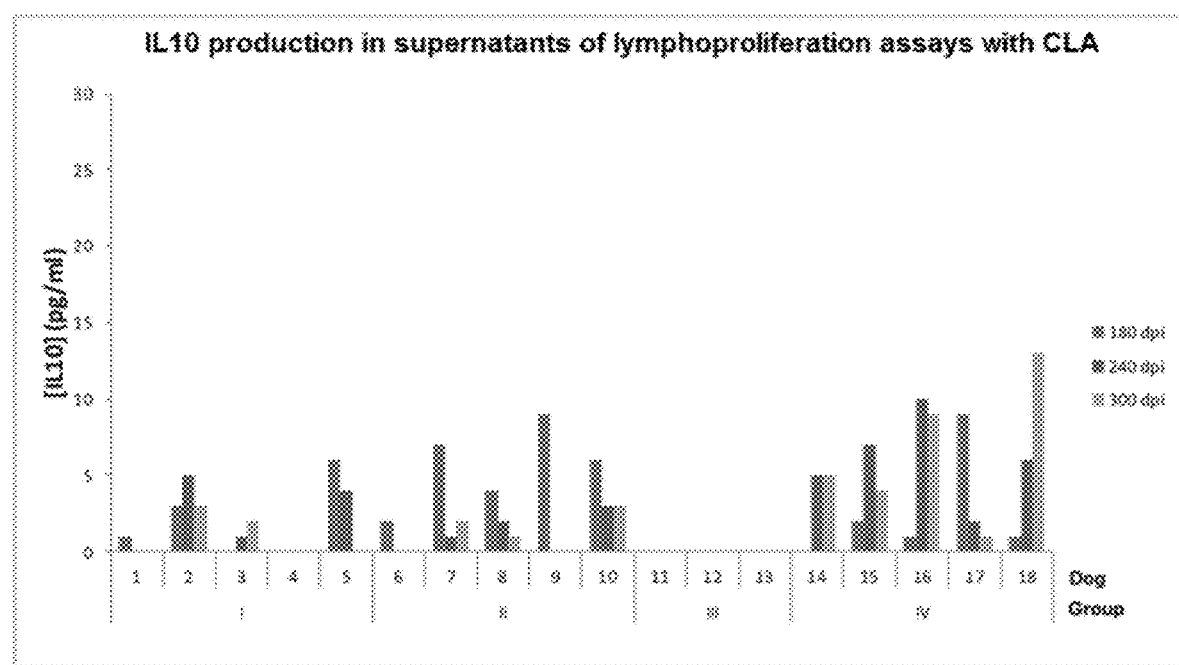
FIG. 14. Evaluation of IL10 production against total *Leishmania* antigen (CLA) in supernatants of lymphoproliferation assays by ELISA.

In peripheral blood mononuclear cells (PBMCs), IFNg production against CLA in groups I and II is higher than in group IV (FIG. 13), and those of IL10 are lower (FIG. 14).

Figure 15:
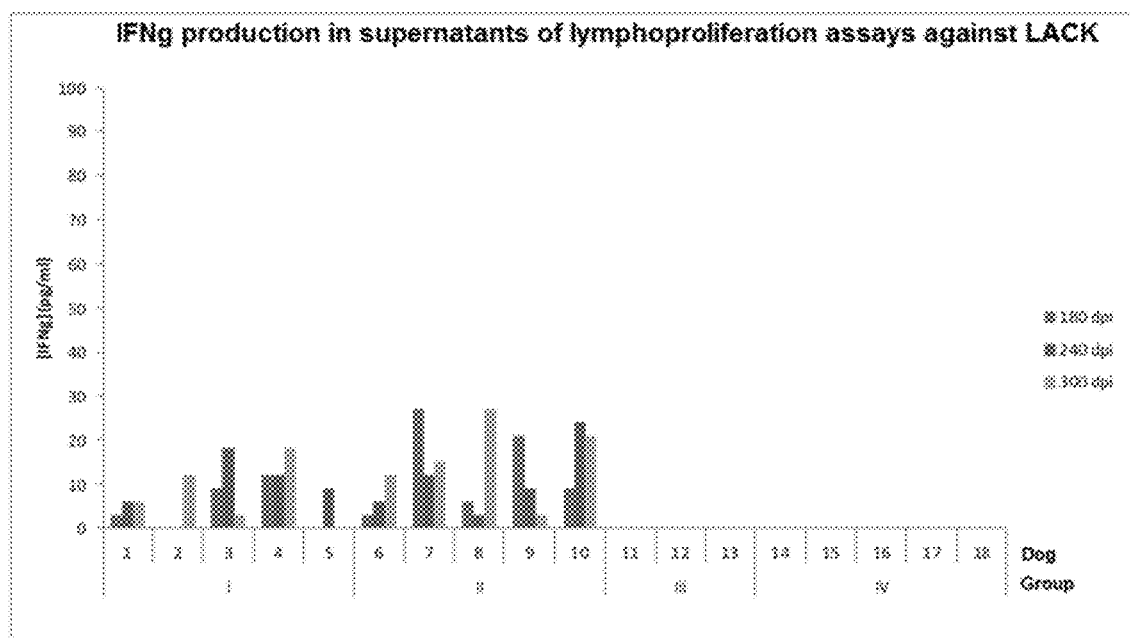
FIG. 15. Evaluation of IFN gamma production against LACK in supernatants of lymphoproliferation assays by ELISA.
Figure 16:
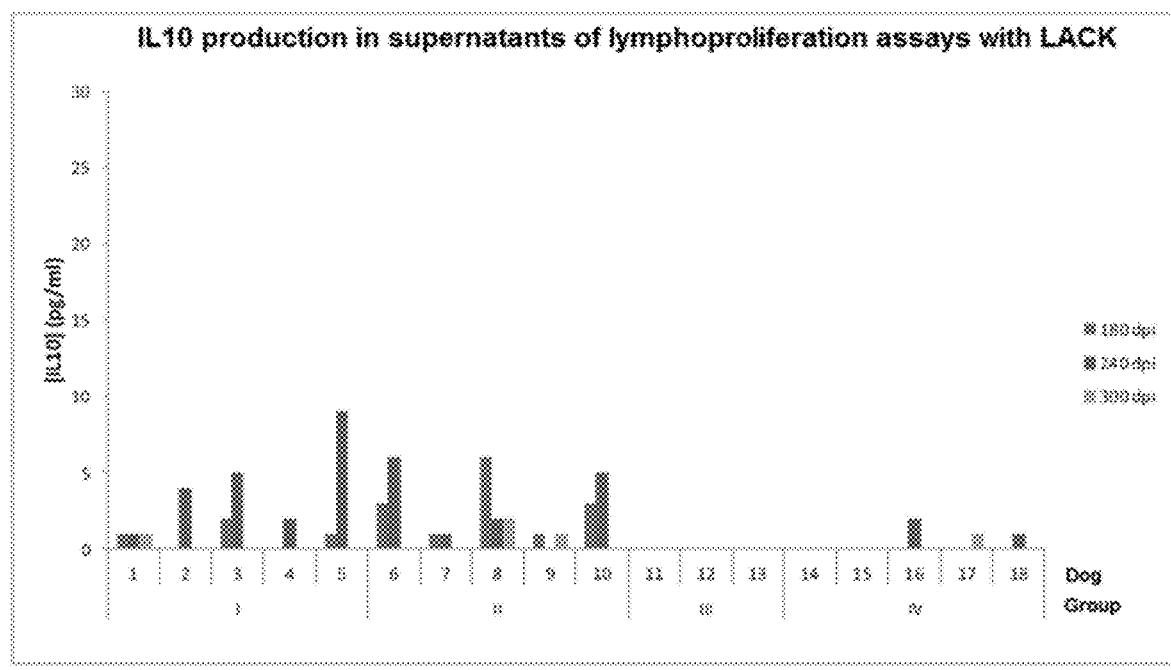
FIG. 16. Evaluation of IL10 production against LACK in supernatants of lymphoproliferation assays by ELISA.
Figure 17:
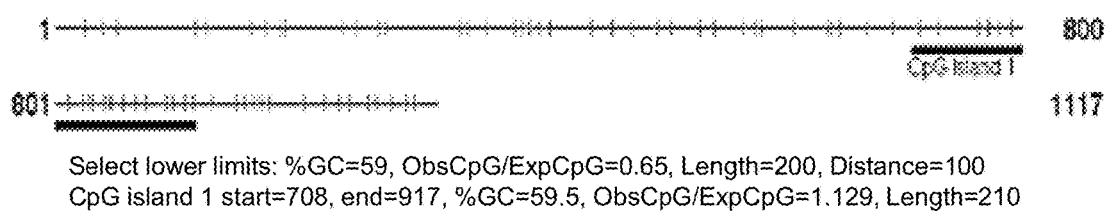
FIG. 17. Results of the CpG island prediction analysis within SEQ ID NO: 21

The same happens against LACK (FIGS. 15 and 16).

In view of these results, the use of the pPAL-LACK plasmid in homologous regime (group I), provides results of IFNg and IL10 production similar to group II, wherein a heterologous regimen (pCIneo-LACK plasmid/MVA-LACK) was used, thus eliminating the need to use a virus.

Example 4.—Determination of the Antigenic Sequence within fabI of *E. coli*

CpG island prediction was performed with CpG Island Searcher Software (Takai et al., 2002, PNAS 99(6):3740-5). First, the sequence of the *E. coli* fab I gene including its promoter (SEQ ID NO:21) was introduced in the software. default parameters (% GC=55; ObsCpG/ExpCpG=0.65; gap between adjacent islands=100 bp) were used except for the selected length (200 pb). As a result, a sequence containing 59% G+C was identified (SEQ ID NO: 1) between positions 700 and 909 of said sequence. This CpG island is postulated as being the immunostimmulatory DNA motif responsible for the observed increased protection levels (see Example 3).

Example 5.—Assessment of the Protection Levels of pPAL-LACK Against Canine Leishmaniasis in Comparison with the Commercial Vaccine CaniLeish® (Virbac)

Example 5.1 Material & Methods

I. Experimentation Animals.

Treatment groups: Group A—positive control (infected, non-immunized); Group E—2 doses of 200 μg pPAL-LACK; Group F—CaniLeish® (Virbac). Each group included 10 healthy one-year-old Beagle dogs (5 male and 5 female each).

II. Infectious Inoculum Preparation and Experimental Infection.

The procedure followed was exactly the same as detailed in 3.1 and 3.2 above.

III. Determination of Cytokines Levels by Reverse Transcription qPCR

1. RNA Extraction.

Fine needle aspiration (about 5 μl) of popliteal lymph node was resuspended in 1 ml TRIzol Reagent (Life Technologies) and RNA extraction was peformed following the instructions specified by the manufacturer.

2. Quantification and Assessment of RNA Quality.

The procedure described in 3.4.3. was followed but using Qubit RNA BR assay kit (Life Technologies) instead of the DNA kit. Run a 2% agarose gel at 5 V/cm until the dye front reaches the bottom of the gel. The comb, electrophoresis cell and tray should be pre-treated with commercial hydrogen peroxide for 30 min and the running buffer prepared with RNAse-free water. Examine the 18S and 28S bands.

3. Reverse Transcription.
 i. Mix 1 μg RNA resuspended in RNase-free water with 1.5 μl 5×SIII RT buffer (Life Technologies), 1 μl of 3

µg/µl random hexamer primers (Life Technologies), 1 µl of the inhibitor RNase out (Life Technologies) and RNase-free water until completion of a final volume of 16.8 µl.

ii. Heat the mixture at 70° C. 10 min and cool immediately to 4° C.

iii. Add the following to the reaction mix: 6 µl 5×SIII RT buffer (Life Technologies), 1.7 µl of 10 mM each dNTP, 1.5 µl of 0.1 M DTT, 3 µl of 200 U/µl SuperScript III reverse transcriptase (Life Technologies) and 1 µl RNase out.

iv. Incubate at 46° C. for 3 h.

v. Add 7 µl of 0.5 M NaOH.

vi. Incubate at 70° C. for 20 min.

vii. Add 7 µl 0.5 M HCl.

viii. Purify with QIAquick PCR Purification Kit (Qiagen) following the manufacturer's instructions.

4. Quantification of cDNA.

The procedure described in 3.4.3 was followed.

5. Real Time Quantitative RT-PCR by the Method of TaqMan Probes

Note: all the mixtures were prepared and reagents kept on ice during the process. The container was decontaminated of DNA and nuclease.

i. In the area of sample handling, 1/5 serial dilutions of cDNA were prepared starting from a solution at a concentration of 2.5 ng/µl.

ii. In the clean area for storage and handling of the reagents, the master reaction mix (master mix) was prepared for all the reactions that had to be performed including dilutions and biological and technical replicates plus a suitable remnant according to pipetting losses. Each reaction mix had a final volume of 10 µl and consisted of the following components, excluding the sample:

| | |
|---|---|
| TaqMan Fast Universal PCR Master Mix (2X) | 5.00 µl (1X) |
| TaqMan Gene Expression Assay (Probe and Primers, 20X) | 0.5 µl (1X) |
| Nuclease-free water (Life Technologies) | 2.5 µl |

The commercial references of the TaqMan Gene Expression Assays were:

| | | |
|---|---|---|
| Dog IFN gamma | Cat. no. #4448892 | Cf02622936_m1 |
| Dog IL10 | Cat. no. #4448892 | Cf02741697_g1 |
| Dog TNF alpha | Cat. no. #4448892 | Assay no. Cf02624261 |
| CAPZB (beta actin) | Cat. no. 4448893 | Assay no. Cf02635224 | iii. Using the multichannel pipette, 8.0 µl of reaction mix per well were added in a 384 well plate, which was prepared in the clean area for storage and handling of reagents.

iv. The plate was moved to the area of sample preparation and 2 µl of sample were added per well.

v. The qPCR reactions were run in a 7900HT Fast Real Time PCR system using the SDS 4.1. software (Life Technologies) following the procedure specified by the manufacturer. The thermal cycling conditions were: 95° C. for 5 min; 40×[95° C. for 30"; 60° C. for 1 min, data acquisition].

6. Analysis

Note: the whole process was performed with Microsoft Excel. There was a template available to do this, so the Ct values and, once the linear regression had been carried out, the value of the slope of the line was entered in the corresponding boxes, so that once this was done the results were automatically obtained.

i. Calculation of the arithmetic means of the replicates made from each dilution, the quasi-standard deviation or uncertainty (standard deviation, SD) and the coefficient of variation (CV).

$$CV (\%) = (SD_{dilution}/Ct_{dilution\ medium}) \times 100$$

ii. Elimination of the points whose CV is greater than 20% (they were considered as outliers).

iii. Calculation of the amplification efficiency independently for each biological sample and for each triad of primers and probe from the data of the corresponding technical replicates and serial dilutions. The Ct value versus log of the total template mass added to the reaction mixture (µg) was represented and linear regression performed. The value of the regression coefficient ($r^2$) should be as close as possible to 1. The efficiency was be determined by the value of the slope of the line.

iv. Calculation of the efficiency.

$$\text{Efficiency} = 10^{(-1/slope)}$$

v. Calculation of the amount corrected with the efficiency for each of the values.

$$\text{Amount} = \text{Efficiency}^{-Ct}$$

vi. Calculation of the mean and SD of the amount for the technical replicates of a given dilution and condition.

vii. Normalization (by condition and dilution). An amount of CAPZB (beta-actin) was considered.

a. The amount values for minicircles (mc) were divided by those of the reference gene (GOR).

b. Calculation of the $SD_{normalized\ amount}$:

$$SD_{normalized\ amount} = \text{Normalized amount} \cdot [(SD_{mc}/\text{Amount}_{mc})^2 + (SD_{GOR}/\text{Amount}_{GOR})^2]^{1/2}$$

IV. Determination of the Parasite Load and IgG Levels

It was performed as described in Example 1, 3.4.4 and 3.5.3.

Example 5.2 Results

I. Parasite Burden

Figure 18:
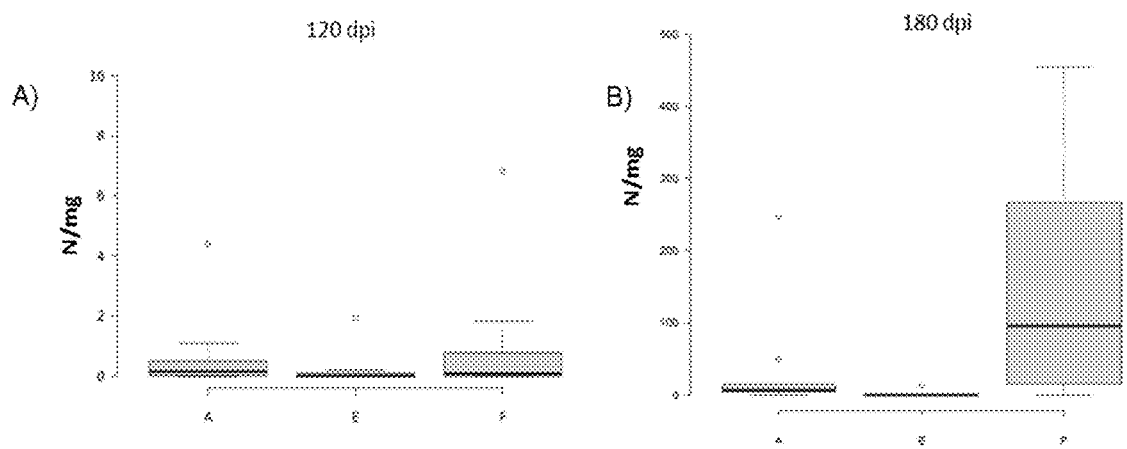
FIG. 18. Graphical representation of the parasite burden in beagle dogs determined by qPCR at different time points A) 120 dpi, B) 180 dpi, C) 240 dpi and D) 300 dpi for each treatment group (A, E and F). Treatment groups: Group A—positive control (infected, non-immunized); Group E—2 doses of 200 μg pPAL-LACK; Group F—CaniLeish® (Virbac). Abbreviations: days post-infection (dpi), N/mg: number of amastigotes per mg of bone marrow tissue.
Figure 18:
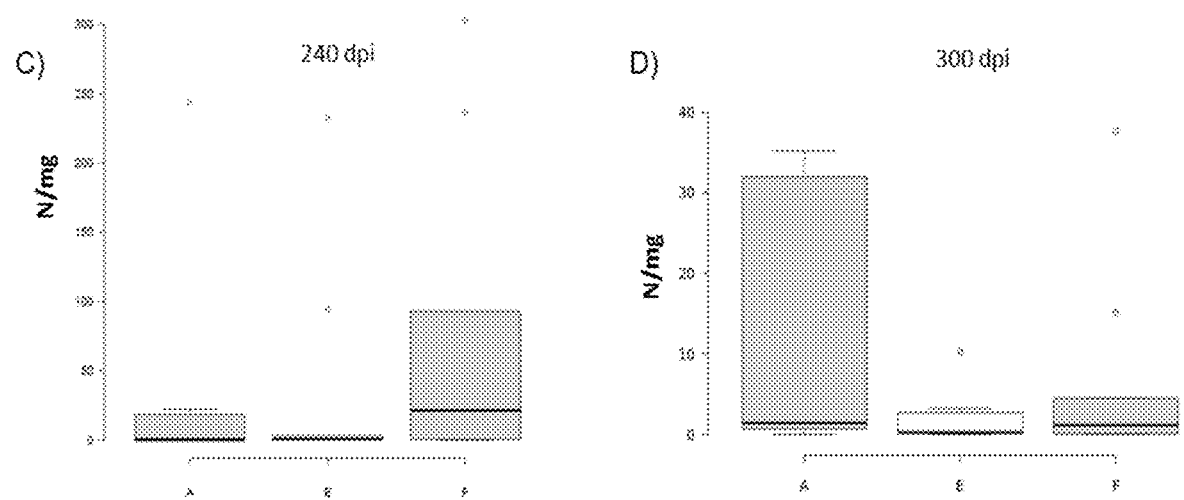
Figure 19:
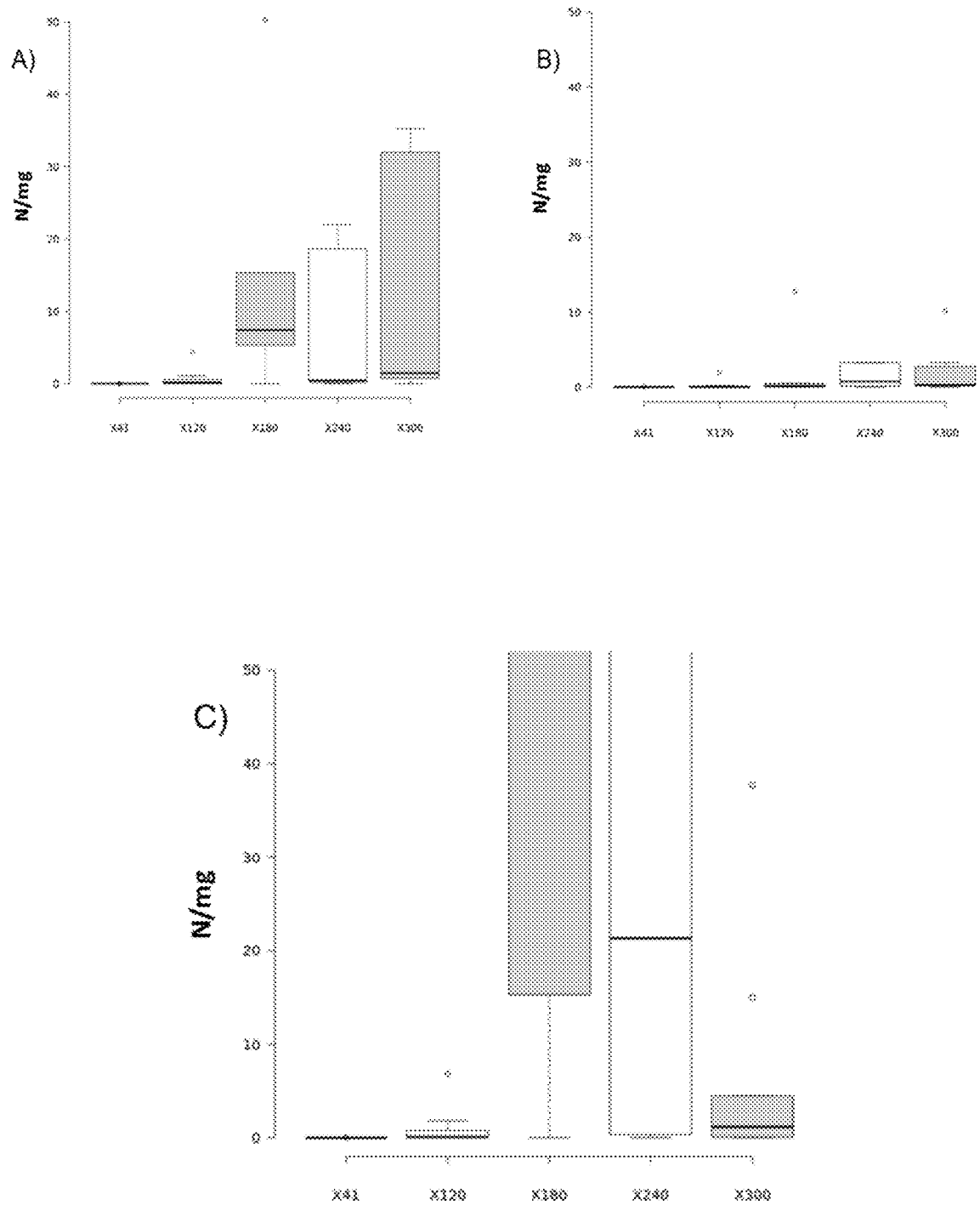
FIG. 19. Graphical representation showing the evolution though time (41 dpi, 120 dpi, 180 dpi, 240 dpi and 300 dpi) of the parasite burden in beagle dogs determined by qPCR for each treatment group A) Group A, B) Group E and C) Group F. Treatment groups: Group A—positive control (infected, non-immunized); Group E—2 doses of 200 μg pPAL-LACK; Group F—CaniLeish® (Virbac). N/mg: number of amastigotes per mg of bone marrow tissue.

This second experiment (blind), shows that the parasite burden is lower in dogs vaccinated with pPAL-LACK (group E, FIG. 18; FIG. 19B) than in the positive control group (group A, FIG. 18; FIG. 19A) and dogs vaccinated with CaniLeish® (group F, FIG. 18; FIG. 19C). This fact supports that protection against the parasite has been considerably improved compared to the commercial vaccine CaniLeish®.

II. Cytokines Expression Levels Determination

Figure 20:
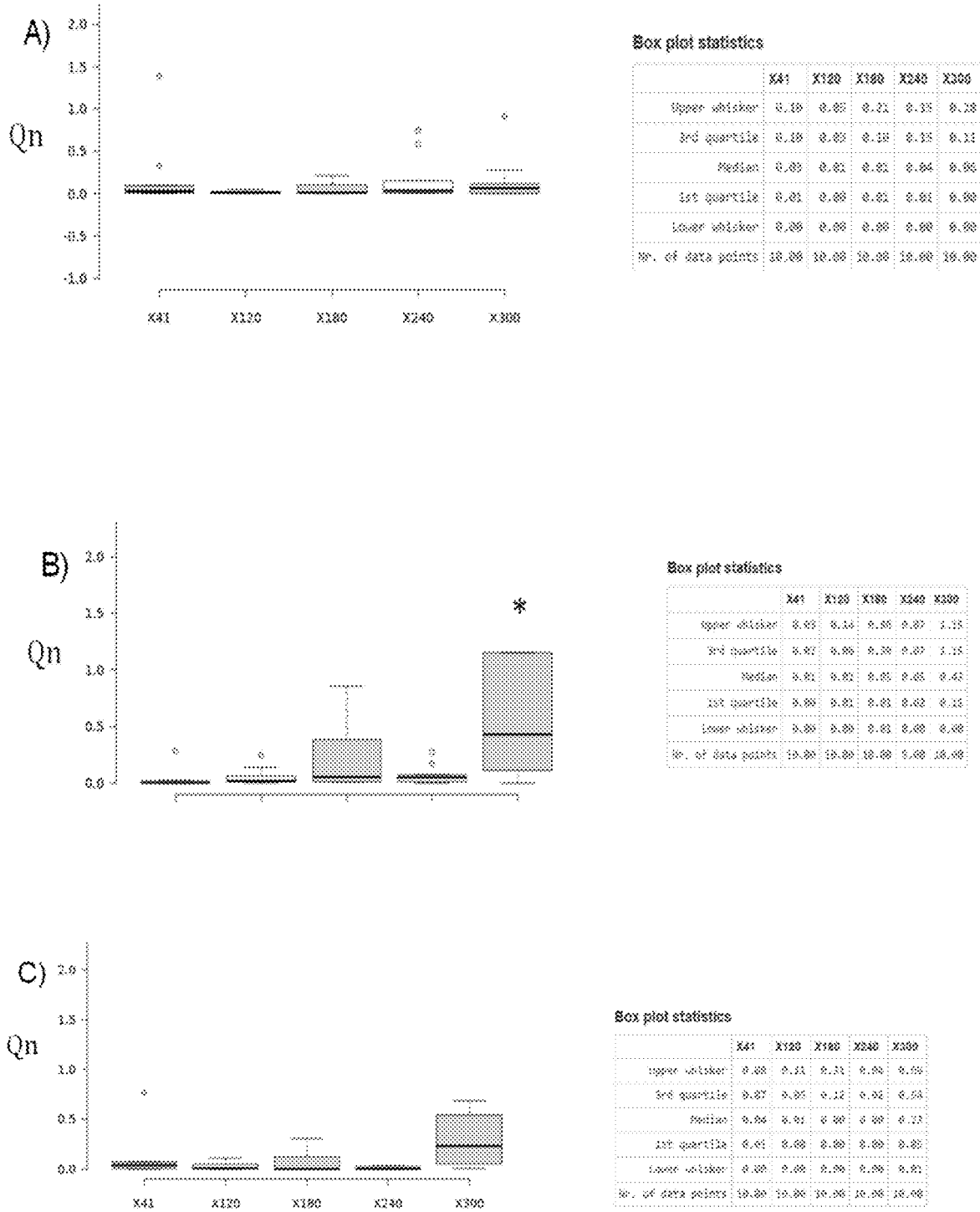
FIG. 20. IFN gamma levels in lymph node of beagle dogs by qPCR at 41 dpi, 120 dpi, 180 dpi, 240 dpi and 300 dpi for each treatment group A) Group A, B) Group E and C) Group F and associated statistic values. Treatment groups: Group A—positive control (infected, non-immunized); Group E—2 doses of 200 μg pPAL-LACK; Group F—CaniLeish® (Virbac). Abbreviations: days post-infection (dpi), Qn=normalized quantity (Bookout et al., 2006, High-throughput real-time quantitative reverse transcription PCR. Curr Protoc Mol Biol Chapter 15: Unit 15 18); * There are two outliers (much higher values).
Figure 21:
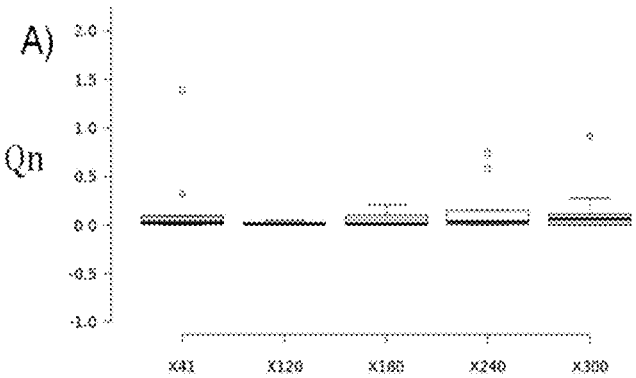
FIG. 21. IL10 levels in lymph node of beagle dogs by qPCR at 41 dpi, 120 dpi, 180 dpi, 240 dpi and 300 dpi for each treatment group A) Group A, B) Group E and C) Group F and associated statistic values. Treatment groups: Group A—positive control (infected, non-immunized); Group E—2 doses of 200 μg pPAL-LACK; Group F—CaniLeish® (Virbac). Abbreviations: days post-infection (dpi), Qn=normalized quantity (Bookout et al., 2006, High-throughput real-time quantitative reverse transcription PCR. Curr Protoc Mol Biol Chapter 15: Unit 15 18).
Figure 21:
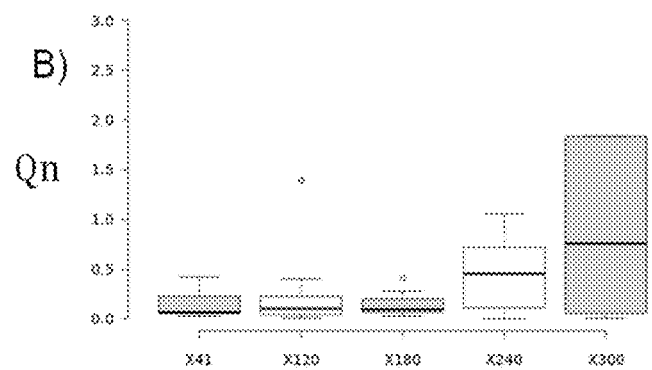
Figure 21:
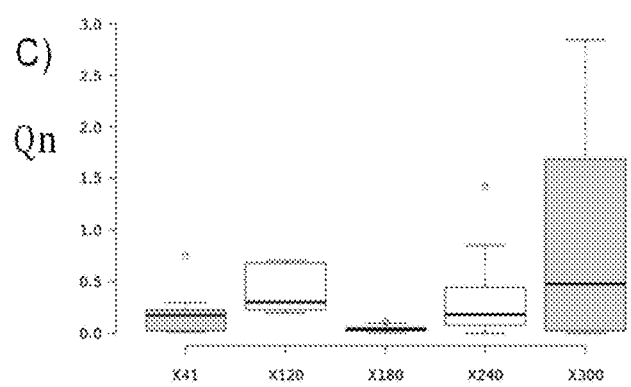
Figure 22:
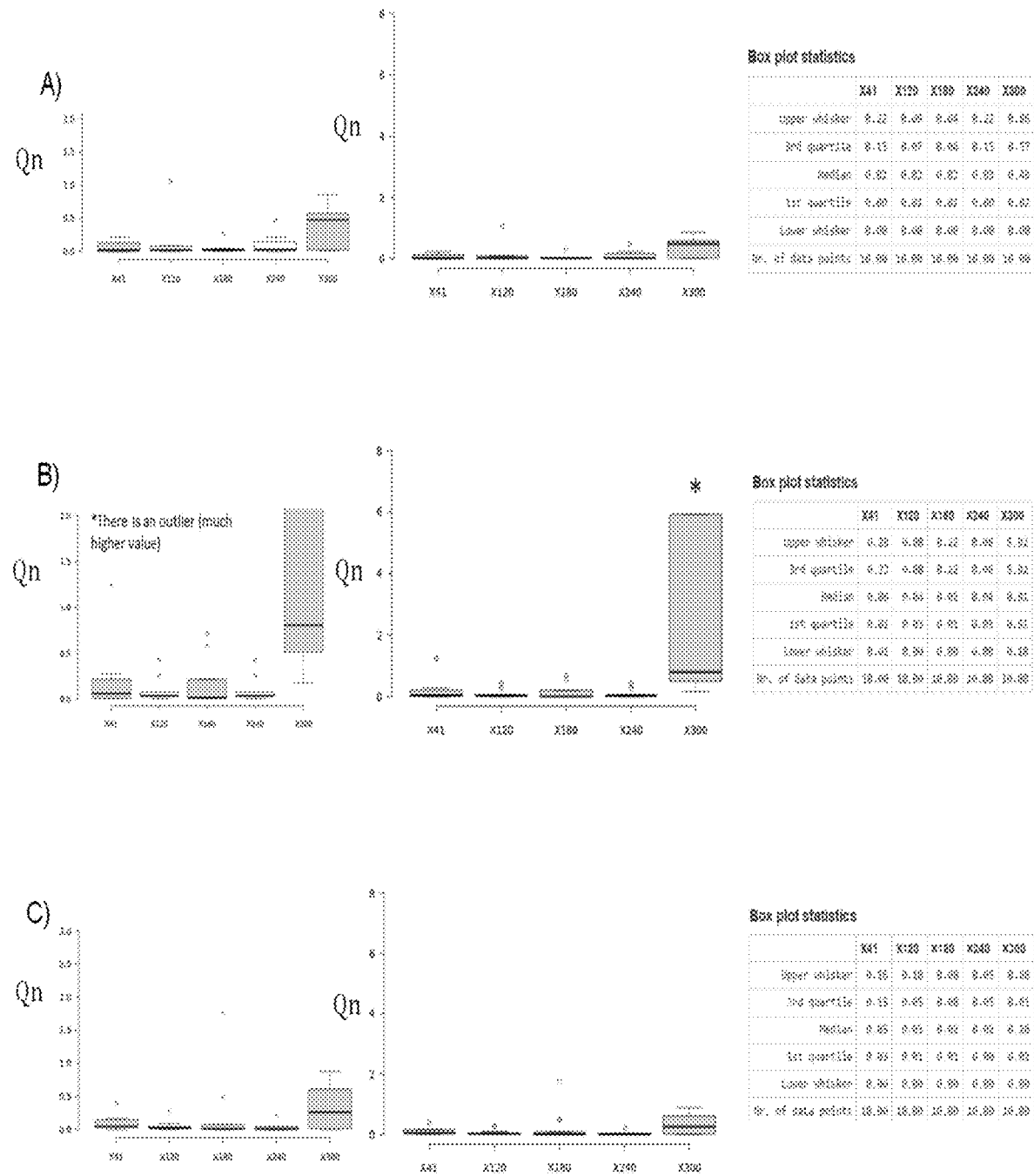
FIG. 22. TNF alpha levels in lymph node of beagle dogs by qPCR at 41 dpi, 120 dpi, 180 dpi, 240 dpi and 300 dpi for each treatment group A) Group A, B) Group E and C) Group F and associated statistic values (zoom values on the left) Treatment groups: Group A—positive control (infected, non-immunized); Group E—2 doses of 200 μg pPAL-LACK; Group F—CaniLeish® (Virbac). Abbreviations: days post-infection (dpi), Qn=normalized quantity (Bookout et al., 2006, High-throughput real-time quantitative reverse transcription PCR. Curr Protoc Mol Biol Chapter 15: Unit 15 18).

At the end of the experiment, the IFNg expression levels in lymph node are considerably higher in group E than in group F and group A (FIG. 20), which support a considerably higher Th1 protective response in the group vaccinated with pPAL-LACK (group E) than in the vaccinated with CaniLeish®. The IL10 increase is earlier in the case of the positive control group (group A) than in the vaccinated groups E•and F (FIG. 21). The relative TNF alpha levels are much higher in the case of the pPAL-LACK vaccinated group E, which is additional evidence for the increase of the Th1 response unlike in the positive control group and the group vaccinated with CaniLeish®.

III. Total IgG, IgG1 and IgG2 Levels Determination

Figure 23:
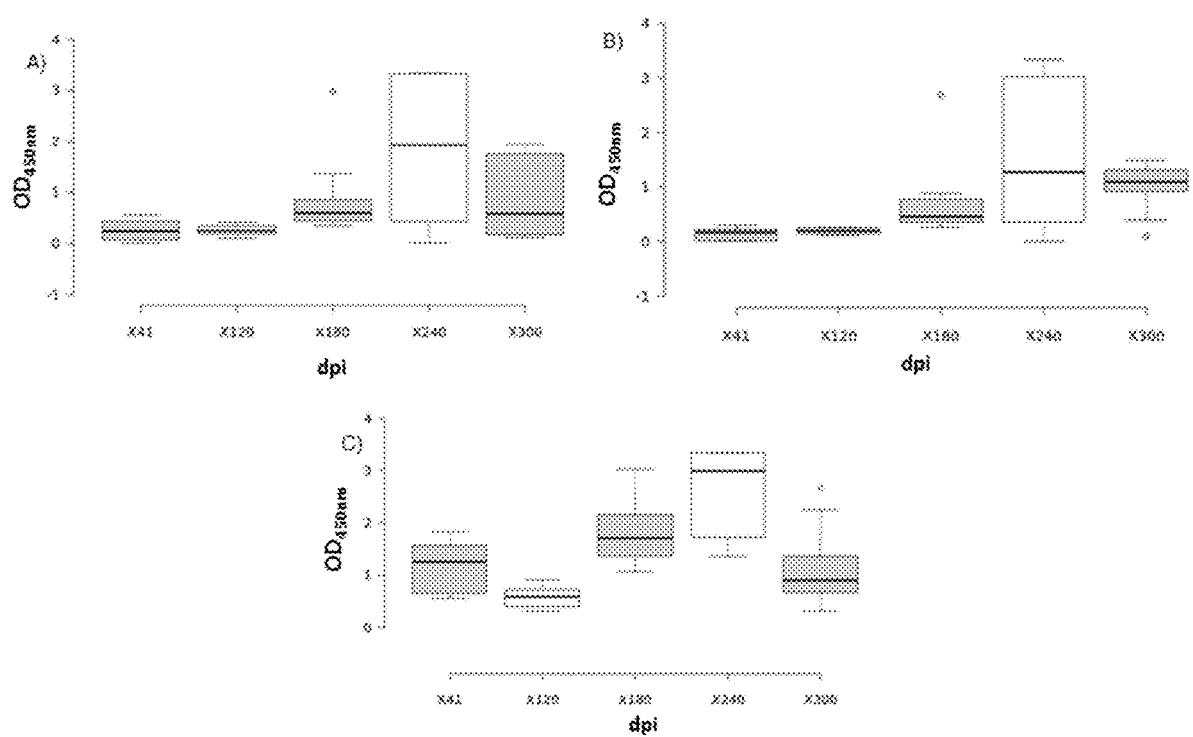
FIG. 23. Total IgG levels in serum of beagle dogs by ELISA at 41 dpi, 120 dpi, 180 dpi, 240 dpi and 300 dpi for each treatment group A) Group A, B) Group E and C) Group F. Treatment groups: Group A—positive control (infected, non-immunized); Group E—2 doses of 200 μg pPAL-LACK; Group F—CaniLeish® (Virbac). Abbreviations: days post-infection (dpi), optical density at 450 nm $OD_{450\ nm}$.
Figure 24:
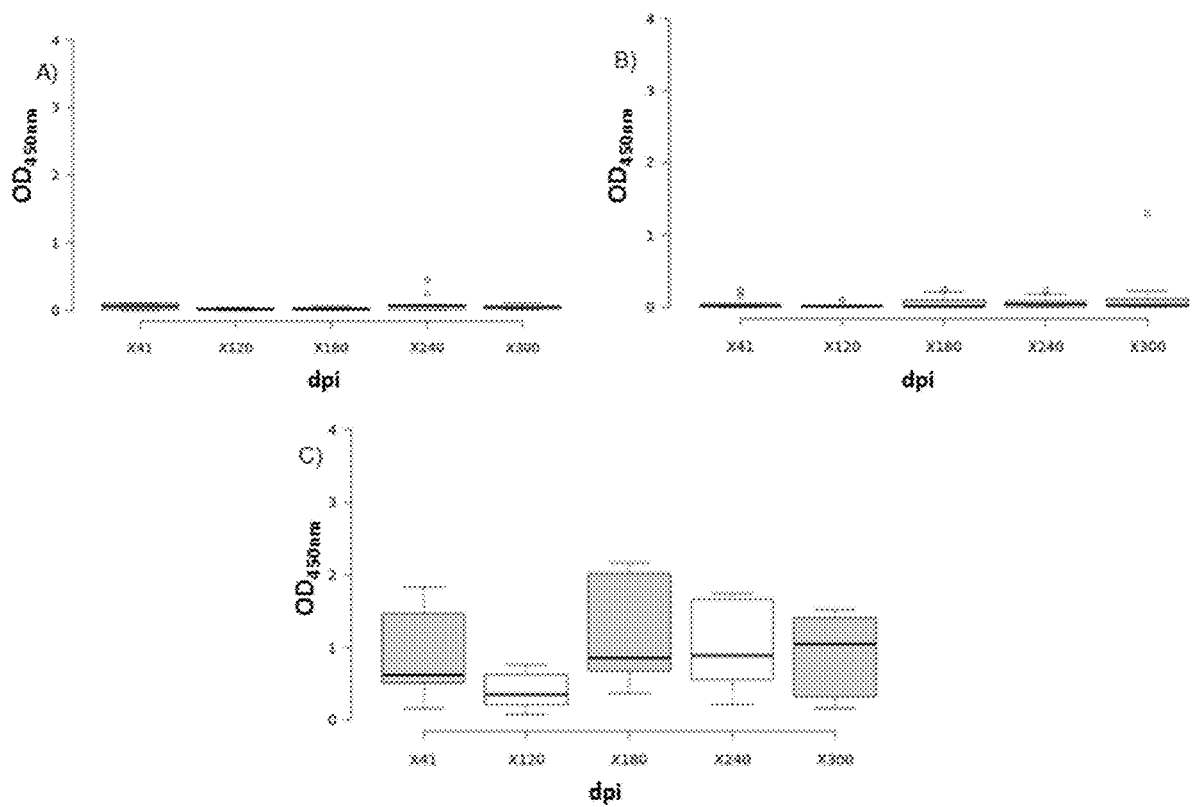
FIG. 24. IgG1 levels in serum of beagle dogs by ELISA at 41 dpi, 120 dpi, 180 dpi, 240 dpi and 300 dpi for each treatment group A) Group A, B) Group E and C) Group F. Treatment groups: Group A—positive control (infected, non-immunized); Group E—2 doses of 200 μg pPAL- LACK; Group F—CaniLeish® (Virbac). Abbreviations: days post-infection (dpi), optical density at 450 nm $OD_{450\ nm}$.
Figure 25:
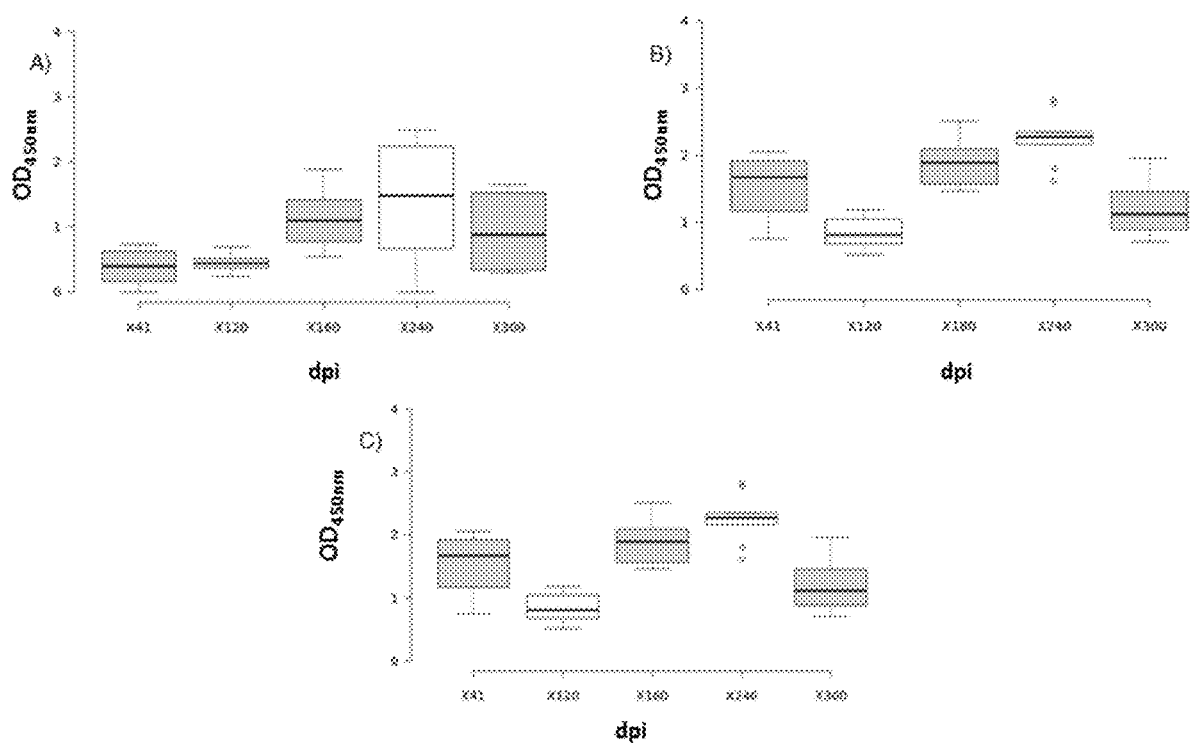
FIG. 25. IgG2 levels in serum of beagle dogs by ELISA at 41 dpi, 120 dpi, 180 dpi, 240 dpi and 300 dpi for each treatment group A) Group A, B) Group E and C) Group F. Treatment groups: Group A—positive control (infected, non-immunized); Group E—2 doses of 200 µg pPAL-LACK; Group F—CaniLeish® (Virbac). Abbreviations: days post-infection (dpi), optical density at 450 nm $OD_{450\ nm}$.

All groups were correctly infected with the parasite according to the parasite burden analysis mentioned above and the analysis of the humoral response (FIG. 23-25). Interestingly, the levels of IgG1 are much higher in the case of the CaniLeish® vaccine than in the positive control group and the experimental group vaccinated with pPAL-LACK. This finding supports that CaniLeish® triggers a humoral response rather than a cellular response unlike pPAL-LACK. An increased humoral response is a marker of susceptibility to the disease.

The invention claimed is:

1. A vaccine for protecting a canine or human subject from leishmaniasis, the vaccine comprising a polynucleotide sequence and further comprising a pharmaceutically acceptable carrier, additive or excipient, wherein said polynucleotide sequence comprises:
   a) a nucleic acid sequence consisting of SEQ ID NO: 3 or
   b) a nucleic acid sequence encoding an amino acid sequence consisting of SEQ ID NO: 4; and
   c) a nucleic acid sequence encoding one or more leishmaniasis antigens.

2. The vaccine of claim 1, wherein the polynucleotide is the pPAL-LACK plasmid of SEQ ID NO: 23.

3. A method for protecting a canine or human subject from leishmaniasis, the method comprising administering to the subject a vaccine comprising a polynucleotide sequence, and further comprising a pharmaceutically acceptable carrier, additive or excipient, wherein said polynucleotide sequence comprises:
   a) a nucleic acid sequence consisting of SEQ ID NO: 3 or
   b) a nucleic acid sequence encoding an amino acid sequence consisting of SEQ ID NO: 4; and
   c) a nucleic acid sequence encoding one or more leishmaniasis antigens.

4. The method of claim 3, wherein one or more nucleic acid sequences are operably linked to control sequences.

5. The method of claim 3, wherein the polynucleotide is a plasmid.

6. The method of claim 5, wherein said plasmid is a circular or linear bacterial DNA.

7. The method of claim 3, wherein the polynucleotide is characterized by the absence of antibiotic resistance genes.

8. The method of claim 3, wherein said nucleic acid sequence encoding one or more leishmaniasis antigens in c) comprises:
   i) a nucleic acid sequence consisting of SEQ ID NO: 5 or
   ii) a nucleic acid sequence encoding an amino acid sequence consisting of SEQ ID NO: 6.

9. The method of claim 3, wherein the polynucleotide is the pPAL-LACK plasmid of SEQ ID NO: 23.

10. The method of claim 3, wherein said leishmaniasis is canine leishmaniasis.

11. The method of claim 3, wherein the administering comprises a homologous prime-boost regime.

12. The method of claim 3, wherein said subject is a human subject.

13. The method of claim 12, wherein said leishmaniasis is visceral leishmaniasis.

14. A method for producing antibodies, comprising immunizing a mammal with the polynucleotide of claim 1, or a pharmaceutical composition comprising the same.

15. The method of claim 14, wherein the polynucleotide is the pPAL-LACK plasmid of SEQ ID NO: 23.

* * * * *

SEQUENCE LISTING

```
<160> NUMBER OF SEQ ID NOS: 27

<210> SEQ ID NO 1
<211> LENGTH: 210
<212> TYPE: DNA
<213> ORGANISM: Artificial Sequence
<220> FEATURE:
<223> OTHER INFORMATION: positions 700 to 909 of the fabI gene of EColi
      BL21 (DE3) strain
<220> FEATURE:
<221> NAME/KEY: misc_feature
<222> LOCATION: (1)..(210)

<400> SEQUENCE: 1
aaaagcttgc cgctccatgc tgaatccggg ttctgccctg ctgacccttt cctaccttgg      60
cgctgagcgc gctatcccga actacaacgt tatgggtctg gcaaaagcgt ctctggaagc     120
gaacgtgcgc tatatggcga acgcgatggg tccggaaggt gtgcgtgtta acgccatctc     180
tgctggtccg atccgtactc tggcggcttc                                      210

<210> SEQ ID NO 2
<211> LENGTH: 69
<212> TYPE: PRT
<213> ORGANISM: Artificial Sequence
<220> FEATURE:
<223> OTHER INFORMATION: polypeptide encoded within SEQ ID NO: 1
<220> FEATURE:
<221> NAME/KEY: MISC_FEATURE
<222> LOCATION: (1)..(69)

<400> SEQUENCE: 2

Lys Ala Cys Arg Ser Met Leu Asn Pro Gly Ser Ala Leu Leu Thr Leu
1               5                   10                  15

Ser Tyr Leu Gly Ala Glu Arg Ala Ile Pro Asn Tyr Asn Val Met Gly
            20                  25                  30

Leu Ala Lys Ala Ser Leu Glu Ala Asn Val Arg Tyr Met Ala Asn Ala
        35                  40                  45

Met Gly Pro Glu Gly Val Arg Val Asn Ala Ile Ser Ala Gly Pro Ile
    50                  55                  60

Arg Thr Leu Ala Ala
65

<210> SEQ ID NO 3
<211> LENGTH: 780
<212> TYPE: DNA
<213> ORGANISM: Artificial Sequence
<220> FEATURE:
<223> OTHER INFORMATION: fabI gene of EColi BL21 (DE3) strain
<220> FEATURE:
<221> NAME/KEY: misc_feature
<222> LOCATION: (1)..(780)

<400> SEQUENCE: 3
atgggttttc tttccggtaa gcgcattctg gtaaccggtg ttgccagcaa actatccatc      60
gcctacggta tcgctcaggc gatgcaccgc gaaggagctg aactggcatt cacctaccag     120
aacgacaaac tgaaaggccg cgtagaagaa tttgccgctc aattgggttc tgacatcgtt     180
ctgcagtgcg atgttgcaga agatgccagc atcgacacca tgttcgctga actggggaaa     240
gtttggccga aatttgacgg tttcgtacac tctattggtt ttgcacctgg cgatcagctg     300
```

```
gatggtgact atgttaacgc cgttacccgt gaaggcttca aaattgccca cgacatcagc    360
tcctacagct tcgttgcaat ggcaaaagct tgccgctcca tgctgaatcc gggttctgcc    420
ctgctgaccc tttcctacct tggcgctgag cgcgctatcc cgaactacaa cgttatgggt    480
ctggcaaaag cgtctctgga agcgaacgtg cgctatatgg cgaacgcgat gggtccggaa    540
ggtgtgcgtg ttaacgccat ctctgctggt ccgatccgta ctctggcggc ttccggtatc    600
aaagacttcc gcaaaatgct ggctcattgc gaagccgtta ccccgattcg ccgtaccgtt    660
actattgaag atgtgggtaa ctctgcggca ttcctgtgct ccgatctctc tgccggtatc    720
tccggtgaaa tagtccacgt tgacggcggt ttcagcatcg ctgcaatgaa cgaactcgaa    780
```

<210> SEQ ID NO 4
<211> LENGTH: 262
<212> TYPE: PRT
<213> ORGANISM: Artificial Sequence
<220> FEATURE:
<223> OTHER INFORMATION: polypeptide encoded by the fabI gene of EColi
      BL21 (DE3) strain
<220> FEATURE:
<221> NAME/KEY: MISC_FEATURE
<222> LOCATION: (1)..(262)

<400> SEQUENCE: 4

```
Met Gly Phe Leu Ser Gly Lys Arg Ile Leu Val Thr Gly Val Ala Ser
1               5                   10                  15

Lys Leu Ser Ile Ala Tyr Gly Ile Ala Gln Ala Met His Arg Glu Gly
            20                  25                  30

Ala Glu Leu Ala Phe Thr Tyr Gln Asn Asp Lys Leu Lys Gly Arg Val
        35                  40                  45

Glu Glu Phe Ala Ala Gln Leu Gly Ser Asp Ile Val Leu Gln Cys Asp
    50                  55                  60

Val Ala Glu Asp Ala Ser Ile Asp Thr Met Phe Ala Glu Leu Gly Lys
65                  70                  75                  80

Val Trp Pro Lys Phe Asp Gly Phe Val His Ser Ile Gly Phe Ala Pro
                85                  90                  95

Gly Asp Gln Leu Asp Gly Asp Tyr Val Asn Ala Val Thr Arg Glu Gly
            100                 105                 110

Phe Lys Ile Ala His Asp Ile Ser Ser Tyr Ser Phe Val Ala Met Ala
        115                 120                 125

Lys Ala Cys Arg Ser Met Leu Asn Pro Gly Ser Ala Leu Leu Thr Leu
    130                 135                 140

Ser Tyr Leu Gly Ala Glu Arg Ala Ile Pro Asn Tyr Asn Val Met Gly
145                 150                 155                 160

Leu Ala Lys Ala Ser Leu Glu Ala Asn Val Arg Tyr Met Ala Asn Ala
                165                 170                 175

Met Gly Pro Glu Gly Val Arg Val Asn Ala Ile Ser Ala Gly Pro Ile
            180                 185                 190

Arg Thr Leu Ala Ala Ser Gly Ile Lys Asp Phe Arg Lys Met Leu Ala
        195                 200                 205

His Cys Glu Ala Val Thr Pro Ile Arg Arg Thr Val Thr Ile Glu Asp
    210                 215                 220

Val Gly Asn Ser Ala Ala Phe Leu Cys Ser Asp Leu Ser Ala Gly Ile
225                 230                 235                 240

Ser Gly Glu Val Val His Val Asp Gly Gly Phe Ser Ile Ala Ala Met
                245                 250                 255
```

Asn Glu Leu Glu Leu Lys
        260

<210> SEQ ID NO 5
<211> LENGTH: 942
<212> TYPE: DNA
<213> ORGANISM: Artificial Sequence
<220> FEATURE:
<223> OTHER INFORMATION: GenBank: U49695.1
<220> FEATURE:
<221> NAME/KEY: misc_feature
<222> LOCATION: (1)..(942)
<220> FEATURE:
<221> NAME/KEY: misc_feature
<222> LOCATION: (1)..(942)
<223> OTHER INFORMATION: LACK gene

<400> SEQUENCE: 5

```
accatgaact acgagggtca cctgaagggc caccgcggat gggtcacctc cctggcctgc      60
ccgcagcagg cggggtcgta catcaaggtg gtgtcgacgt cgcgcgatgg cacggccatc     120
tcgtggaaag ccaaccccga ccgccacagc gtggacagcg actacggtct gccgagccac     180
cgcctcgagg gccacaccgg cttcgtgtcg tgtgtgtcgc tggcccacgc caccgactac     240
gcgctgaccg cgtcctggga ccgctccatc cgcatgtggg acctgcgcaa tggccagtgc     300
cagcgcaagt cctgaagca caccaaggac gtgctcgccg tcgccttctc gccggacgac     360
cgcctgatcg tgtccgcggg ccgcgacaac gtgatccgcg tgtggaacgt ggcgggcgag     420
tgcatgcacg agttcctgcg cgacggccac gaggactggg tgagcagcat ctgtttctcg     480
ccgtcgctgg agcatccgat cgtggtgtcc ggcagctggg acaacaccat caaggtatgg     540
aacgtgaacg ggggcaagtg tgagcgcacg ctcaagggcc acagcaacta cgtgtccacg     600
gtgacggtgt cgccagacgg gtcgctgtgc gcgtccggcg gcaaggacgg cgcggcgctg     660
ctgtgggacc tgagcaccgg cgagcagctg ttcaagatca acgtggagtc gcccatcaac     720
cagatcgcct tctcgcccaa ccgcttctgg atgtgcgtcg cgacggagag gtctctgtcc     780
gtgtacgacc tggagagcaa ggctgtgatt gcggagctga cgccggacgg cgcgaagccg     840
tccgagtgca tctccattgc ctggtccgcc gacggcaaca ctctgtactc cggtcacaag     900
gacaacctga tccgcgtgtg gtccatctcc gacgccgagt aa                        942
```

<210> SEQ ID NO 6
<211> LENGTH: 312
<212> TYPE: PRT
<213> ORGANISM: Artificial Sequence
<220> FEATURE:
<223> OTHER INFORMATION: LACK antigen
<220> FEATURE:
<221> NAME/KEY: MISC_FEATURE
<222> LOCATION: (1)..(312)

<400> SEQUENCE: 6

Met Asn Tyr Glu Gly His Leu Lys Gly His Arg Gly Trp Val Thr Ser
1               5                   10                  15

Leu Ala Cys Pro Gln Gln Ala Gly Ser Tyr Ile Lys Val Val Ser Thr
            20                  25                  30

Ser Arg Asp Gly Thr Ala Ile Ser Trp Lys Ala Asn Pro Asp Arg His
        35                  40                  45

Ser Val Asp Ser Asp Tyr Gly Leu Pro Ser His Arg Leu Glu Gly His
    50                  55                  60

Thr Gly Phe Val Ser Cys Val Ser Leu Ala His Ala Thr Asp Tyr Ala
65                  70                  75                  80

Leu Thr Ala Ser Trp Asp Arg Ser Ile Arg Met Trp Asp Leu Arg Asn
                85                  90                  95

Gly Gln Cys Gln Arg Lys Phe Leu Lys His Thr Lys Asp Val Leu Ala
            100                 105                 110

Val Ala Phe Ser Pro Asp Asp Arg Leu Ile Val Ser Ala Gly Arg Asp
        115                 120                 125

Asn Val Ile Arg Val Trp Asn Val Ala Gly Glu Cys Met His Glu Phe
    130                 135                 140

Leu Arg Asp Gly His Glu Asp Trp Val Ser Ser Ile Cys Phe Ser Pro
145                 150                 155                 160

Ser Leu Glu His Pro Ile Val Val Ser Gly Ser Trp Asp Asn Thr Ile
                165                 170                 175

Lys Val Trp Asn Val Asn Gly Gly Lys Cys Glu Arg Thr Leu Lys Gly
            180                 185                 190

His Ser Asn Tyr Val Ser Thr Val Thr Val Ser Pro Asp Gly Ser Leu
        195                 200                 205

Cys Ala Ser Gly Gly Lys Asp Gly Ala Ala Leu Leu Trp Asp Leu Ser
    210                 215                 220

Thr Gly Glu Gln Leu Phe Lys Ile Asn Val Glu Ser Pro Ile Asn Gln
225                 230                 235                 240

Ile Ala Phe Ser Pro Asn Arg Phe Trp Met Cys Val Ala Thr Glu Arg
                245                 250                 255

Ser Leu Ser Val Tyr Asp Leu Glu Ser Lys Ala Val Ile Ala Glu Leu
            260                 265                 270

Thr Pro Asp Gly Ala Lys Pro Ser Glu Cys Ile Ser Ile Ala Trp Ser
        275                 280                 285

Ala Asp Gly Asn Thr Leu Tyr Ser Gly His Lys Asp Asn Leu Ile Arg
    290                 295                 300

Val Trp Ser Ile Ser Asp Ala Glu
305                 310

<210> SEQ ID NO 7
<211> LENGTH: 312
<212> TYPE: DNA
<213> ORGANISM: Artificial Sequence
<220> FEATURE:
<223> OTHER INFORMATION: promoter of the FabI gene
<220> FEATURE:
<221> NAME/KEY: misc_feature
<222> LOCATION: (1)..(312)

<400> SEQUENCE: 7
gtgctggaga atattcggca aggtctgaac cgtcccagcc atcgccatga aagggttagg      60
ggctgtatga gcctgtttgt tgctggggta acaatatttg cacaatacgg tcccctcgcc     120
cctctgggga gagggttagg gtgagggaa aagcgccccc cctgccgcag cctgctccgg      180
tcggacctgg caactatagc tactcacagc caggttgatt ataataaccg tttatctgtt     240
cgtactgttt actaaaacga cgaatcgcct gattttcagg cacaacaagc atcaacaata     300
aggattaaag ct                                                         312

<210> SEQ ID NO 8
<211> LENGTH: 32
<212> TYPE: DNA
<213> ORGANISM: Artificial Sequence
<220> FEATURE:
<223> OTHER INFORMATION: PacI-fabI-promoter-Fw
<220> FEATURE:

<221> NAME/KEY: misc_feature
<222> LOCATION: (1)..(32)

<400> SEQUENCE: 8
tactggatta attaagtgct ggagaatatt cg                                32

<210> SEQ ID NO 9
<211> LENGTH: 37
<212> TYPE: DNA
<213> ORGANISM: Artificial Sequence
<220> FEATURE:
<223> OTHER INFORMATION: PacI-fabI-Rv
<220> FEATURE:
<221> NAME/KEY: misc_feature
<222> LOCATION: (1)..(37)

<400> SEQUENCE: 9
tactggatta attaattatt tcagttcgag ttcgttc                           37

<210> SEQ ID NO 10
<211> LENGTH: 35
<212> TYPE: DNA
<213> ORGANISM: Artificial Sequence
<220> FEATURE:
<223> OTHER INFORMATION: PacI-pCIbla-1
<220> FEATURE:
<221> NAME/KEY: misc_feature
<222> LOCATION: (1)..(35)

<400> SEQUENCE: 10
tactggatta attaaccgcg tatggtgcac tctca                             35

<210> SEQ ID NO 11
<211> LENGTH: 34
<212> TYPE: DNA
<213> ORGANISM: Artificial Sequence
<220> FEATURE:
<223> OTHER INFORMATION: PacI-pCIbla-2
<220> FEATURE:
<221> NAME/KEY: misc_feature
<222> LOCATION: (1)..(34)

<400> SEQUENCE: 11
tactggatta attaacgctg gcaagtgtag cggt                              34

<210> SEQ ID NO 12
<211> LENGTH: 31
<212> TYPE: DNA
<213> ORGANISM: Artificial Sequence
<220> FEATURE:
<223> OTHER INFORMATION: BamHI-pCI- bla-1
<220> FEATURE:
<221> NAME/KEY: misc_feature
<222> LOCATION: (1)..(31)

<400> SEQUENCE: 12
gtacaggatc ccatgtgtca gaggttttca c                                 31

<210> SEQ ID NO 13
<211> LENGTH: 32
<212> TYPE: DNA
<213> ORGANISM: Artificial Sequence
<220> FEATURE:
<223> OTHER INFORMATION: BamHI-pCI- bla-2
<220> FEATURE:
<221> NAME/KEY: misc_feature
<222> LOCATION: (1)..(32)

<400> SEQUENCE: 13

```
gtacaggatc cgcagaagtg gtcctgcaac tt                                        32

<210> SEQ ID NO 14
<211> LENGTH: 21
<212> TYPE: DNA
<213> ORGANISM: Artificial Sequence
<220> FEATURE:
<223> OTHER INFORMATION: pCIseq1
<220> FEATURE:
<221> NAME/KEY: misc_feature
<222> LOCATION: (1)..(21)

<400> SEQUENCE: 14
tcaatattgg ccattagcca t                                                    21

<210> SEQ ID NO 15
<211> LENGTH: 21
<212> TYPE: DNA
<213> ORGANISM: Artificial Sequence
<220> FEATURE:
<223> OTHER INFORMATION: 106-LACK-pCIseq
<220> FEATURE:
<221> NAME/KEY: misc_feature
<222> LOCATION: (1)..(21)

<400> SEQUENCE: 15
ccacgagatg gccgtgccat c                                                    21

<210> SEQ ID NO 16
<211> LENGTH: 20
<212> TYPE: DNA
<213> ORGANISM: Artificial Sequence
<220> FEATURE:
<223> OTHER INFORMATION: LACK-Fw
<220> FEATURE:
<221> NAME/KEY: misc_feature
<222> LOCATION: (1)..(20)

<400> SEQUENCE: 16
atgaactacg agggtcacct                                                      20

<210> SEQ ID NO 17
<211> LENGTH: 19
<212> TYPE: DNA
<213> ORGANISM: Artificial Sequence
<220> FEATURE:
<223> OTHER INFORMATION: LACK-Rv
<220> FEATURE:
<221> NAME/KEY: misc_feature
<222> LOCATION: (1)..(19)

<400> SEQUENCE: 17
ttactcggcg tcggagatg                                                       19

<210> SEQ ID NO 18
<211> LENGTH: 21
<212> TYPE: DNA
<213> ORGANISM: Artificial Sequence
<220> FEATURE:
<223> OTHER INFORMATION: pCIseq2
<220> FEATURE:
<221> NAME/KEY: misc_feature
<222> LOCATION: (1)..(21)

<400> SEQUENCE: 18
gttaagggat tttggtcatg a                                                    21
```

<210> SEQ ID NO 19
<211> LENGTH: 21
<212> TYPE: DNA
<213> ORGANISM: Artificial Sequence
<220> FEATURE:
<223> OTHER INFORMATION: pCIseq3
<220> FEATURE:
<221> NAME/KEY: misc_feature
<222> LOCATION: (1)..(21)

<400> SEQUENCE: 19
tcatgaccaa atcccttaa c                                        21

<210> SEQ ID NO 20
<211> LENGTH: 18
<212> TYPE: DNA
<213> ORGANISM: Artificial Sequence
<220> FEATURE:
<223> OTHER INFORMATION: XbaI-pCIseq4
<220> FEATURE:
<221> NAME/KEY: misc_feature
<222> LOCATION: (1)..(18)

<400> SEQUENCE: 20
tctagagtcg acccgggc                                           18

<210> SEQ ID NO 21
<211> LENGTH: 1101
<212> TYPE: DNA
<213> ORGANISM: Artificial Sequence
<220> FEATURE:
<223> OTHER INFORMATION: fabI gene and its promoter
<220> FEATURE:
<221> NAME/KEY: misc_feature
<222> LOCATION: (1)..(1101)

<400> SEQUENCE: 21
gtgctggaga atattcggca aggtctgaac cgtcccagcc atcgccatga aagggttagg    60
ggctgtatga gcctgtttgt tgctggggta acaatatttg cacaatacgg tcccctcgcc   120
cctctgggga gagggttagg gtgaggggaa aagcgccccc cctgccgcag cctgctccgg   180
tcggacctgg caactatagc tactcacagc caggttgatt ataataaccg tttatctgtt   240
cgtactgttt actaaaacga cgaatcgcct gattttcagg cacaacaagc atcaacaata   300
aggattaaag ctatgggttt tctttccggt aagcgcattc tggtaaccgg tgttgccagc   360
aaactatcca tcgcctacgg tatcgctcag gcgatgcacc gcgaaggagc tgaactggca   420
ttcacctacc agaacgacaa actgaaaggc gcgtagaag aatttgccgc tcaattgggt   480
tctgacatcg ttctgcagtg cgatgttgca gaagatgcca gcatcgacac catgttcgct   540
gaactgggga agtttggcc gaaatttgac ggtttcgtac actctattgg ttttgcacct   600
ggcgatcagc tggatggtga ctatgttaac gccgttaccc gtgaaggctt caaaattgcc   660
cacgacatca gctcctacag cttcgttgca atggcaaaag cttgccgctc catgctgaat   720
ccgggttctg ccctgctgac ccttttcctac cttggcgctg agcgcgctat cccgaactac   780
aacgttatgg gtctggcaaa agcgtctctg gaagcgaacg tgcgctatat ggcgaacgcg   840
atgggtccgg aaggtgtgcg tgttaacgcc atctctgctg gtccgatccg tactctggcg   900
gcttccggta tcaaagactt ccgcaaaatg ctggctcatt gcgaagccgt taccccgatt   960
cgccgtaccg ttactattga agatgtgggt aactctgcgg cattcctgtg ctccgatctc  1020
tctgccggta tctccggtga agtagtccac gttgacggcg gtttcagcat cgctgcaatg  1080
aacgaactcg aactgaaata a                                            1101

```
<210> SEQ ID NO 22
<211> LENGTH: 5694
<212> TYPE: DNA
<213> ORGANISM: Artificial Sequence
<220> FEATURE:
<223> OTHER INFORMATION: pCI-bla-fabI-LACK
<220> FEATURE:
<221> NAME/KEY: misc_feature
<222> LOCATION: (1)..(5694)

<400> SEQUENCE: 22
```

| | | | | | |
|---|---|---|---|---|---|
| tcaatattgg | ccattagcca | tattattcat | tggttatata | gcataaatca | atattggcta | 60 |
| ttggccattg | catacgttgt | atctatatca | taatatgtac | atttatattg | gctcatgtcc | 120 |
| aatatgaccg | ccatgttggc | attgattatt | gactagttat | taatagtaat | caattacggg | 180 |
| gtcattagtt | catagcccat | atatggagtt | ccgcgttaca | taacttacgg | taaatggccc | 240 |
| gcctggctga | ccgcccaacg | acccccgccc | attgacgtca | ataatgacgt | atgttcccat | 300 |
| agtaacgcca | atagggactt | tccattgacg | tcaatgggtg | gagtatttac | ggtaaactgc | 360 |
| ccacttggca | gtacatcaag | tgtatcatat | gccaagtccg | cccctattg | acgtcaatga | 420 |
| cggtaaatgg | cccgcctggc | attatgccca | gtacatgacc | ttacgggact | ttcctacttg | 480 |
| gcagtacatc | tacgtattag | tcatcgctat | taccatggtg | atgcggtttt | ggcagtacac | 540 |
| caatgggcgt | ggatagcggt | ttgactcacg | ggatttcca | agtctccacc | ccattgacgt | 600 |
| caatgggagt | ttgttttggc | accaaaatca | acgggacttt | ccaaaatgtc | gtaacaactg | 660 |
| cgatcgcccg | ccccgttgac | gcaaatgggc | ggtaggcgtg | tacggtggga | ggtctatata | 720 |
| agcagagctc | gtttagtgaa | ccgtcagatc | actagaagct | ttattgcggt | agtttatcac | 780 |
| agttaaattg | ctaacgcagt | cagtgcttct | gacacaacag | tctcgaactt | aagctgcagt | 840 |
| gactctctta | aggtagcctt | gcagaagttg | gtcgtgaggc | actgggcagg | taagtatcaa | 900 |
| ggttacaaga | caggtttaag | gagaccaata | gaaactgggc | ttgtcgagac | agagaagact | 960 |
| cttgcgtttc | tgataggcac | ctattggtct | tactgacatc | cactttgcct | ttctctccac | 1020 |
| aggtgtccac | tcccagttca | attacagctc | ttaaggctag | agtacttaat | acgactcact | 1080 |
| ataggctagc | ctcgagaatt | caccatgaac | tacgagggtc | acctgaaggg | ccaccgcgga | 1140 |
| tgggtcacct | ccctggcctg | cccgcagcag | gcggggtcgt | acatcaaggt | ggtgtcgacg | 1200 |
| tcgcgcgatg | gcacggccat | ctcgtggaaa | gccaaccccg | accgccacag | cgtggacagc | 1260 |
| gactacggtc | tgccgagcca | ccgcctcgag | ggccacaccg | gcttcgtgtc | gtgtgtgtcg | 1320 |
| ctggcccacg | ccaccgacta | cgcgctgacc | gcgtcctggg | accgctccat | ccgcatgtgg | 1380 |
| gacctgcgca | atggccagtg | ccagcgcaag | ttcctgaagc | acaccaagga | cgtgctcgcc | 1440 |
| gtcgccttct | cgccggacga | ccgcctgatc | gtgtccgcgg | gccgcgacaa | cgtgatccgc | 1500 |
| gtgtggaacg | tggcgggcga | gtgcatgcac | gagttcctgc | gcgacggcca | cgaggactgg | 1560 |
| gtgagcagca | tctgtttctc | gccgtcgctg | gagcatccga | tcgtggtgtc | cggcagctgg | 1620 |
| gacaacacca | tcaaggtatg | aacgtgaac | gggggcaagt | gtgagcgcac | gctcaagggc | 1680 |
| cacagcaact | acgtgtccac | ggtgacggtg | tcgccagacg | ggtcgctgtg | cgcgtccggc | 1740 |
| ggcaaggacg | gcgcggcgct | gctgtgggac | ctgagcaccg | gcgagcagct | gttcaagatc | 1800 |
| aacgtggagt | cgcccatcaa | ccagatcgcc | ttctcgccca | accgcttctg | gatgtgcgtc | 1860 |
| gcgacggaga | ggtctctgtc | cgtgtacgac | ctggagagca | aggctgtgat | tgcggagctg | 1920 |
| acgccggacg | gcgcgaagcc | gtccgagtgc | atctccattg | cctggtccgc | cgacggcaac | 1980 |

```
actctgtact ccggtcacaa ggacaacctg atccgcgtgt ggtccatctc cgacgccgag    2040
taactagagt cgacccgggc ggccgcttcc ctttagtgag ggttaatgct tcgagcagac    2100
atgataagat acattgatga gtttggacaa accacaacta gaatgcagtg aaaaaaatgc    2160
tttatttgtg aaatttgtga tgctattgct ttatttgtaa ccattataag ctgcaataaa    2220
caagttaaca acaacaattg cattcatttt atgtttcagg ttcaggggga gatgtgggag    2280
gttttttaaa gcaagtaaaa cctctacaaa tgtggtaaaa tccgataagg atcgatccgg    2340
gctggcgtaa tagcgaagag gcccgcaccg atcgcccttc ccaacagttg cgcagcctga    2400
atggcgaatg gacgcgccct gtagcggcgc attaagcgcg gcgggtgtgg tggttacgcg    2460
cagcgtgacc gctacacttg ccagcgttaa ttaagtgctg agaatattc ggcaaggtct    2520 gaaccgtccc agccatcgcc atgaaagggt taggggctgt atgagcctgt tgttgctgg    2580 ggtaacaata tttgcacaat acggtcccct cgcccctctg gggagagggt tagggtgagg    2640
ggaaaagcgc cccccctgcc gcagcctgct ccggtcggac ctggcaacta tagctactca    2700
cagccaggtt gattataata accgtttatc tgttcgtact gtttactaaa cgacgaatc    2760 gcctgatttt caggcacaac aagcatcaac aataaggatt aaagctatgg gttttctttc    2820
cggtaagcgc attctggtaa ccggtgttgc cagcaaacta tccatcgcct acggtatcgc    2880
tcaggcgatg caccgcgaag gagctgaact ggcattcacc taccgaacg acaaactgaa    2940 aggccgcgta gaagaatttg ccgctcaatt gggttctgac atcgttctgc agtgcgatgt    3000
tgcagaagat gccagcatcg acaccatgtt cgctgaactg gggaaagttt ggccgaaatt    3060
tgacggtttc gtacactcta ttggttttgc acctggcgat cagctggatg gtgactatgt    3120
taacgccgtt acccgtgaag gcttcaaaat tgcccacgac atcagctcct acagcttcgt    3180
tgcaatggca aaagcttgcc gctccatgct gaatccgggt tctgccctgc tgacccttc    3240 ctaccttggc gctgagcgcg ctatcccgaa ctacaacgtt atgggtctgg caaaagcgtc    3300
tctggaagcg aacgtgcgct atatggcgaa gcgatgggt ccggaaggtg tgcgtgttaa    3360
cgccatctct gctggtccga tccgtactct ggcggcttcc ggtatcaaag acttccgcaa    3420
aatgctggct cattgcgaag ccgttaccc gattcgccgt accgttacta ttgaagatgt    3480
gggtaactct gcggcattcc tgtgctccga tctctctgcc ggtatctccg gtgaagtagt    3540
ccacgttgac ggcggtttca gcatcgctgc aatgaacgaa ctcgaactga ataattaat    3600 taaccgcgta ccgcgtatgg tgcactctca gtacaatctg ctctgatgcc gcatagttaa    3660
gccagccccg acacccgcca acacccgctg acgcgccctg acgggcttgt ctgctcccgg    3720
catccgctta cagacaagct gtgaccgtct ccgggagctg catgtgtcag aggttttcac    3780
cgtcatcacc gaaacgcgcg agacgaaagg gcctcgtgat acgcctattt ttataggtta    3840
atgtcatgat aataatggtt tcttagacgt caggtggcac ttttcgggga atgtgcgcg    3900 gaacccctat ttgtttattt ttctaaatac attcaaatat gtatccgctc atgagacaat    3960
aaccctgata aatgcttcaa taatattgaa aaaggaagag tatgagtatt caacatttcc    4020
gtgtcgccct tattcccttt tttgcggcat tttgccttcc tgtttttgct cacccagaaa    4080
cgctggtgaa agtaaaagat gctgaagatc agttgggtgc acgagtgggt tacatcgaac    4140
tggatctcaa cagcggtaag atccttgaga gttttcgccc cgaagaacgt tttccaatga    4200
tgagcacttt taaagttctg ctatgtggcg cggtattatc ccgtattgac gccgggcaag    4260
agcaactcgg tcgccgcata cactattctc agaatgactt ggttgagtac tcaccagtca    4320
```

| | |
|---|---|
| cagaaaagca tcttacggat ggcatgacag taagagaatt atgcagtgct gccataacca | 4380 |
| tgagtgataa cactgcggcc aacttacttc tgacaacgat cggaggaccg aaggagctaa | 4440 |
| ccgcttttt gcacaacatg ggggatcatg taactcgcct tgatcgttgg aaccggagc | 4500 |
| tgaatgaagc cataccaaac gacgagcgtg acaccacgat gcctgtagca atggcaacaa | 4560 |
| cgttgcgcaa actattaact ggcgaactac ttactctagc ttcccggcaa caattaatag | 4620 |
| actggatgga ggcggataaa gttgcaggac cacttctgcg ctcggccctt ccggctggct | 4680 |
| ggtttattgc tgataaatct ggagccggtg agcgtgggtc tcgcggtatc attgcagcac | 4740 |
| tggggccaga tggtaagccc tcccgtatcg tagttatcta cacgacgggg agtcaggcaa | 4800 |
| ctatggatga acgaaataga cagatcgctg agataggtgc ctcactgatt aagcattggt | 4860 |
| aactgtcaga ccaagtttac tcatatatac tttagattga tttaaaactt cattttaat | 4920 |
| ttaaaaggat ctaggtgaag atccttttg ataatctcat gaccaaaatc ccttaacgtg | 4980 |
| agttttcgtt ccactgagcg tcagaccccg tagaaaagat caaaggatct tcttgagatc | 5040 |
| cttttttct gcgcgtaatc tgctgcttgc aaacaaaaaa accaccgcta ccagcggtgg | 5100 |
| tttgtttgcc ggatcaagag ctaccaactc tttttccgaa ggtaactggc ttcagcagag | 5160 |
| cgcagatacc aaatactgtc cttctagtgt agccgtagtt aggccaccac ttcaagaact | 5220 |
| ctgtagcacc gcctacatac ctcgctctgc taatcctgtt accagtggct gctgccagtg | 5280 |
| gcgataagtc gtgtcttacc gggttggact caagacgata gttaccggat aaggcgcagc | 5340 |
| ggtcgggctg aacggggggt tcgtgcacac agcccagctt ggagcgaacg acctacaccg | 5400 |
| aactgagata cctacagcgt gagctatgag aaagcgccac gcttcccgaa gggagaaagg | 5460 |
| cggacaggta tccggtaagc ggcagggtcg gaacaggaga gcgcacgagg gagcttccag | 5520 |
| ggggaaacgc ctggtatctt tatagtcctg tcgggtttcg ccacctctga cttgagcgtc | 5580 |
| gatttttgtg atgctcgtca ggggggcgga gcctatggaa aaacgccagc aacgcggcct | 5640 |
| ttttacggtt cctggccttt tgctggcctt ttgctcacat ggctcgacag atct | 5694 |

<210> SEQ ID NO 23
<211> LENGTH: 4828
<212> TYPE: DNA
<213> ORGANISM: Artificial Sequence
<220> FEATURE:
<223> OTHER INFORMATION: pPAL-LACK
<220> FEATURE:
<221> NAME/KEY: misc_feature
<222> LOCATION: (1)..(4828)

<400> SEQUENCE: 23

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg acccccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg ccccctattg acgtcaatga | 420 |
| cggtaaatgg cccgcctggc attatgccca gtacatgacc ttacgggact ttcctacttg | 480 |
| gcagtacatc tacgtattag tcatcgctat taccatggtg atgcggtttt ggcagtacac | 540 |
| caatgggcgt ggatagcggt ttgactcacg gggatttcca agtctccacc ccattgacgt | 600 |

```
caatgggagt tgttttggc accaaaatca acgggacttt ccaaaatgtc gtaacaactg    660
cgatcgcccg ccccgttgac gcaaatgggc ggtaggcgtg tacggtggga ggtctatata   720
agcagagctc gtttagtgaa ccgtcagatc actagaagct ttattgcggt agtttatcac   780
agttaaattg ctaacgcagt cagtgcttct gacacaacag tctcgaactt aagctgcagt   840
gactctctta aggtagcctt gcagaagttg gtcgtgaggc actgggcagg taagtatcaa   900
ggttacaaga caggtttaag gagaccaata gaaactgggc ttgtcgagac agaagagact   960
cttgcgtttc tgataggcac ctattggtct tactgacatc cactttgcct ttctctccac  1020
aggtgtccac tcccagttca attacagctc ttaaggctag agtacttaat acgactcact  1080
ataggctagc ctcgagaatt caccatgaac tacgagggtc acctgaaggg ccaccgcgga  1140
tgggtcacct ccctggcctg cccgcagcag gcggggtcgt acatcaaggt ggtgtcgacg  1200
tcgcgcgatg gcacggccat ctcgtggaaa gccaaccccg accgccacag cgtggacagc  1260
gactacggtc tgccgagcca ccgcctcgag ggccacaccg gcttcgtgtc gtgtgtgtcg  1320
ctggcccacg ccaccgacta cgcgctgacc gcgtcctggg accgctccat ccgcatgtgg  1380
gacctgcgca atggccagtg ccagcgcaag ttcctgaagc acaccaagga cgtgctcgcc  1440
gtcgccttct cgccggacga ccgcctgatc gtgtccgcgg gccgcgacaa cgtgatccgc  1500
gtgtggaacg tggcgggcga gtgcatgcac gagttcctgc gcgacggcca cgaggactgg  1560
gtgagcagca tctgtttctc gccgtcgctg agcatccga tcgtggtgtc cggcagctgg  1620
gacaacacca tcaaggtatg gaacgtgaac ggggggcaagt gtgagcgcac gctcaagggc  1680
cacagcaact acgtgtccac ggtgacggtg tcgccagacg ggtcgctgtg cgcgtccggc  1740
ggcaaggacg gcgcggcgct gctgtgggac ctgagcaccg gcgagcagct gttcaagatc  1800
aacgtggagt cgcccatcaa ccagatcgcc ttctcgccca accgcttctg gatgtgcgtc  1860
gcgacggaga ggtctctgtc cgtgtacgac ctggagagca aggctgtgat tgcggagctg  1920
acgccggacg gcgcgaagcc gtccgagtgc atctccattg cctggtccgc cgacggcaac  1980
actctgtact ccggtcacaa ggacaacctg atccgcgtgt ggtccatctc cgacgccgag  2040
taactagagt cgacccgggc ggccgcttcc ctttagtgag ggttaatgct tcgagcagac  2100
atgataagat acattgatga gtttggacaa accacaacta gaatgcagtg aaaaaaatgc  2160
tttatttgtg aaatttgtga tgctattgct ttatttgtaa ccattataag ctgcaataaa  2220
caagttaaca acaacaattg cattcatttt atgtttcagg ttcagggggga gatgtgggag  2280 gttttttaaa gcaagtaaaa cctctacaaa tgtggtaaaa tccgataagg atcgatccgg  2340
gctggcgtaa tagcgaagag gcccgcaccg atcgcccttc ccaacagttg cgcagcctga  2400
atggcgaatg gacgcgccct gtagcggcgc attaagcgcg gcgggtgtgg tggttacgcg  2460
cagcgtgacc gctacacttg ccagcgttaa ttaagtgctg gagaatattc ggcaaggtct  2520
gaaccgtccc agccatcgcc atgaaagggt taggggctgt atgagcctgt ttgttgctgg  2580
ggtaacaata tttgcacaat acggtcccct cgccctctg ggagagggt tagggtgagg  2640 ggaaaagcgc ccccctgcc gcagcctgct ccggtcggac ctggcaacta gctactca   2700 cagccaggtt gattataata accgtttatc tgttcgtact gtttactaaa acgacgaatc  2760
gcctgatttt caggcacaac aagcatcaac aataaggatt aaagctatgg ttttctttc   2820 cggtaagcgc attctggtaa ccggtgttgc cagcaaacta tccatcgcct acggtatcgc  2880
tcaggcgatg caccgcgaag gagctgaact ggcattcacc taccagaacg acaaactgaa  2940
aggccgcgta gaagaatttg ccgctcaatt gggttctgac atcgttctgc agtgcgatgt  3000
```

```
tgcagaagat gccagcatcg acaccatgtt cgctgaactg gggaaagttt ggccgaaatt      3060
tgacggtttc gtacactcta ttggttttgc acctggcgat cagctggatg gtgactatgt      3120
taacgccgtt acccgtgaag gcttcaaaat tgcccacgac atcagctcct acagcttcgt      3180
tgcaatggca aaagcttgcc gctccatgct gaatccgggt tctgccctgc tgacccttc       3240 ctaccttggc gctgagcgcg ctatcccgaa ctacaacgtt atgggtctgg caaaagcgtc      3300
tctggaagcg aacgtgcgct atatggcgaa cgcgatgggc ccggaaggtg tgcgtgttaa      3360
cgccatctct gctggtccga tccgtactct ggcggcttcc ggtatcaaag acttccgcaa      3420
aatgctggct cattgcgaag ccgttacccc gattcgccgt accgttacta ttgaagatgt      3480
gggtaactct gcggcattcc tgtgctccga tctctctgcc ggtatctccg gtgaagtagt      3540
ccacgttgac ggcggtttca gcatcgctgc aatgaacgaa ctcgaactga ataattaat       3600 taaccgcgta tggtgcactc tcagtacaat ctgctctgat gccgcatagt taagccagcc      3660
ccgacacccg ccaacacccg ctgacgcgcc ctgacgggct gtctgctcc cggcatccgc       3720 ttacagacaa gctgtgaccg tctccgggag ctcatgtgtc agaggttttc acaagttgca      3780
ggaccacttc tgcgctcggc ccttccggct ggctggttta ttgctgataa atctggagcc      3840
ggtgagcgtg gtctcgcgg tatcattgca gcactggggc cagatggtaa gccctcccgt       3900
atcgtagtta tctacacgac ggggagtcag gcaactatgg atgaacgaaa tagacagatc      3960
gctgagatag gtgcctcact gattaagcat tggtaactgt cagaccaagt ttactcatat      4020
atactttaga ttgatttaaa acttcatttt taatttaaaa ggatctaggt gaagatcctt      4080
tttgataatc tcatgaccaa aatccctaa cgtgagtttt cgttccactg agcgtcagac        4140
cccgtagaaa agatcaaagg atcttcttga tccttttt ttctgcgcgt aatctgctgc         4200
ttgcaaacaa aaaaaccacc gctaccagcg gtggtttgtt tgccggatca agagctacca      4260 actcttttc cgaaggtaac tggcttcagc agagcgcaga taccaaatac tgtccttcta       4320
gtgtagccgt agttaggcca ccacttcaag aactctgtag caccgcctac atacctcgct      4380
ctgctaatcc tgttaccagt ggctgctgcc agtggcgata gtcgtgtct taccgggttg       4440 gactcaagac gatagttacc ggataaggcg cagcggtcgg gctgaacggg gggttcgtgc      4500
acacagccca gcttggagcg aacgacctac accgaactga gatacctaca gcgtgagcta      4560
tgagaaagcg ccacgcttcc cgaagggaga aaggcggaca ggtatccggt aagcggcagg      4620
gtcggaacag gagagcgcac gagggagctt ccaggggaa acgcctggta tctttatagt       4680
cctgtcgggt ttcgccacct ctgacttgag cgtcgatttt tgtgatgctc gtcaggggg        4740 cggagcctat ggaaaaacgc cagcaacgcg gccttttac ggttcctggc cttttgctgg       4800
ccttttgctc acatggctcg acagatct                                         4828
```

<210> SEQ ID NO 24
<211> LENGTH: 3899
<212> TYPE: DNA
<213> ORGANISM: Artificial Sequence
<220> FEATURE:
<223> OTHER INFORMATION: pPAL
<220> FEATURE:
<221> NAME/KEY: misc_feature
<222> LOCATION: (1)..(3899)

<400> SEQUENCE: 24

```
tcaatatttgg ccattagcca tattattcat tggttatata gcataaatca atattggcta      60
ttggccattg catacgttgt atctatatca taatatgtac atttatattg gctcatgtcc      120
```

```
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg accccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg cccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca gtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc ctcgagaatt cacgcgtggt acctctagag tcgacccggg cggccgcttc   1140
cctttagtga gggttaatgc ttcgagcaga catgataaga tacattgatg agtttggaca   1200
aaccacaact agaatgcagt gaaaaaaatg ctttatttgt gaaatttgtg atgctattgc   1260
tttatttgta accattataa gctgcaataa acaagttaac aacaacaatt gcattcattt   1320
tatgtttcag gttcaggggg agatgtggga ggttttttaa agcaagtaaa acctctacaa   1380
atgtggtaaa atccgataag gatcgatccg ggctggcgta atagcgaaga ggcccgcacc   1440
gatcgccctt cccaacagtt gcgcagcctg aatggcgaat ggacgcgccc tgtagcggcg   1500
cattaagcgc ggcgggtgtg gtggttacgc gcagcgtgac cgctacactt gccagcgtta   1560
attaagtgct ggagaatatt cggcaaggtc tgaaccgtcc cagccatcgc catgaaaggg   1620
ttaggggctg tatgagcctg tttgttgctg gggtaacaat atttgcacaa tacggtcccc   1680
tcgcccctct ggggagaggg ttagggtgag gggaaaagcg ccccccctgc cgcagcctgc   1740
tccggtcgga cctggcaact atagctactc acagccaggt tgattataat aaccgtttat   1800
ctgttcgtac tgtttactaa aacgacgaat cgcctgattt tcaggcacaa caagcatcaa   1860
caataaggat taaagctatg ggttttcttt ccggtaagcg cattctggta accggtgttg   1920
ccagcaaact atccatcgcc tacggtatcg ctcaggcgat gcaccgcgaa ggagctgaac   1980
tggcattcac ctaccagaac gacaaactga aaggccgcgt agaagaattt gccgctcaat   2040
tgggttctga catcgttctg cagtgcgatg ttgcagaaga tgccagcatc gacaccatgt   2100
tcgctgaact ggggaaagtt tggccgaaat tgacggtttt cgtacactct attggttttg   2160
cacctggcga tcagctggat ggtgactatg ttaacgccgt tacccgtgaa ggcttcaaaa   2220
ttgcccacga catcagctcc tacagcttcg ttgcaatggc aaaagcttgc cgctccatgc   2280
tgaatccggg ttctgccctg ctgacccttt cctaccttgg cgctgagcgc gctatcccga   2340
actacaacgt tatgggtctg gcaaaagcgt ctctggaagc gaacgtgcgc tatatggcga   2400
acgcgatggg tccggaaggt gtgcgtgtta acgccatctc tgctggtccg atccgtactc   2460
```

-continued

| | |
|---|---|
| tggcggcttc cggtatcaaa gacttccgca aaatgctggc tcattgcgaa gccgttaccc | 2520 |
| cgattcgccg taccgttact attgaagatg tgggtaactc tgcggcattc ctgtgctccg | 2580 |
| atctctctgc cggtatctcc ggtgaagtag tccacgttga cggcggtttc agcatcgctg | 2640 |
| caatgaacga actcgaactg aaataattaa ttaaccgcgt atggtgcact ctcagtacaa | 2700 |
| tctgctctga tgccgcatag ttaagccagc cccgacaccc gccaacaccc gctgacgcgc | 2760 |
| cctgacgggc ttgtctgctc ccggcatccg cttacagaca agctgtgacc gtctccggga | 2820 |
| gctcatgtgt cagaggtttt cacaagttgc aggaccactt ctgcgctcgg ccttccggc | 2880 |
| tggctggttt attgctgata atctggagc cggtgagcgt gggtctcgcg gtatcattgc | 2940 |
| agcactgggg ccagatggta agccctcccg tatcgtagtt atctacacga cggggagtca | 3000 |
| ggcaactatg gatgaacgaa atagacagat cgctgagata ggtgcctcac tgattaagca | 3060 |
| ttggtaactg tcagaccaag tttactcata tatactttag attgatttaa aacttcattt | 3120 |
| ttaatttaaa aggatctagg tgaagatcct ttttgataat ctcatgacca aaatccctta | 3180 |
| acgtgagttt tcgttccact gagcgtcaga ccccgtagaa aagatcaaag gatcttcttg | 3240 |
| agatcctttt tttctgcgcg taatctgctg cttgcaaaca aaaaaaccac cgctaccagc | 3300 |
| ggtggtttgt ttgccggatc aagagctacc aactcttttt ccgaaggtaa ctggcttcag | 3360 |
| cagagcgcag ataccaaata ctgtccttct agtgtagccg tagttaggcc accacttcaa | 3420 |
| gaactctgta gcaccgccta catacctcgc tctgctaatc ctgttaccag tggctgctgc | 3480 |
| cagtggcgat aagtcgtgtc ttaccgggtt ggactcaaga cgatagttac cggataaggc | 3540 |
| gcagcggtcg ggctgaacgg ggggttcgtg cacacagccc agcttggagc gaacgaccta | 3600 |
| caccgaactg agatacctac agcgtgagct atgagaaagc gccacgcttc ccgaagggag | 3660 |
| aaaggcggac aggtatccgg taagcggcag ggtcggaaca ggagagcgca cgagggagct | 3720 |
| tccaggggga aacgcctggt atctttatag tcctgtcggg tttcgccacc tctgacttga | 3780 |
| gcgtcgattt tgtgatgct cgtcaggggg cggagccta tggaaaaacg ccagcaacgc | 3840 |
| ggcctttta cggttcctgg ccttttgctg gccttttgct cacatggctc gacagatct | 3899 |

<210> SEQ ID NO 25
<211> LENGTH: 23
<212> TYPE: DNA
<213> ORGANISM: Artificial Sequence
<220> FEATURE:
<223> OTHER INFORMATION: Leish-1 Forward primer
<220> FEATURE:
<221> NAME/KEY: misc_feature
<222> LOCATION: (1)..(23)

<400> SEQUENCE: 25

| | |
|---|---|
| aacttttctg gtcctccggg tag | 23 |

<210> SEQ ID NO 26
<211> LENGTH: 17
<212> TYPE: DNA
<213> ORGANISM: Artificial Sequence
<220> FEATURE:
<223> OTHER INFORMATION: Leish-2 Reverse Primer
<220> FEATURE:
<221> NAME/KEY: misc_feature
<222> LOCATION: (1)..(17)

<400> SEQUENCE: 26

| | |
|---|---|
| acccccagtt tcccgcc | 17 |

```
<210> SEQ ID NO 27
<211> LENGTH: 18
<212> TYPE: DNA
<213> ORGANISM: Artificial Sequence
<220> FEATURE:
<223> OTHER INFORMATION: Leish-P Probe
<220> FEATURE:
<221> NAME/KEY: misc_feature
<222> LOCATION: (1)..(18)

<400> SEQUENCE: 27
aaaaatgggt gcagaaat                                                 18
```